(12) United States Patent
Ma et al.

(10) Patent No.: US 8,221,988 B2
(45) Date of Patent: *Jul. 17, 2012

(54) METHODS AND COMPOSITIONS RELATING TO CCR5 ANTAGONIST, IFN-γ AND IL-13 INDUCED INFLAMMATION

(75) Inventors: Bing Ma, Branford, CT (US); Jack Elias, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/084,239

(22) Filed: Apr. 11, 2011

(65) Prior Publication Data

US 2011/0311560 A1 Dec. 22, 2011

Related U.S. Application Data

(63) Continuation-in-part of application No. 10/582,610, filed as application No. PCT/US2004/041374 on Dec. 13, 2004, now Pat. No. 7,943,130.

(60) Provisional application No. 60/528,892, filed on Dec. 11, 2003.

(51) Int. Cl.
*G01N 33/53* (2006.01)
*A61K 39/395* (2006.01)

(52) U.S. Cl. ...................... 435/7.1; 424/130.1

(58) Field of Classification Search ............... None
See application file for complete search history.

(56) References Cited

U.S. PATENT DOCUMENTS

| | | | |
|---|---|---|---|
| 6,100,087 A | 8/2000 | Rossi | |
| 6,476,028 B1 | 11/2002 | Bondinell | |
| 6,528,625 B1 | 3/2003 | Wu | |
| 7,282,568 B2 | 10/2007 | Teeling | |
| 7,943,130 B2* | 5/2011 | Ma et al. | 424/130.1 |
| 2003/0017979 A1 | 1/2003 | Mack | |
| 2007/0010509 A1 | 1/2007 | Shiota | |

FOREIGN PATENT DOCUMENTS

| | | |
|---|---|---|
| EP | 1623721 | 2/2006 |
| EP | 1661889 | 5/2006 |
| WO | 01/51077 | 7/2001 |
| WO | 01/64213 | 9/2001 |
| WO | 2004/056809 | 7/2004 |

OTHER PUBLICATIONS

Algood et al. "CCR5-deficient mice control *Mycobacterium tuberculosis* infection despite increased pulmonary lymphocytic infiltration." J. Immunol. 173:3287-3296 (2004).
Cartier et al. "Chemokine-induced cell death in CCR5-expressing neuroblastoma cells." J. Neuroimmunol. 145:27-39 (2003).
Fraziano et al. "Expression of CCR5 is increased in human monocyte-derived macrophages and alveolar macrophages in the course of in vivo and in vitro *Mycobacterium tuberculosis* infection." AIDS Res. Hum. Retroviruses. 15:869-74 (1999).
Huffilagle et al. "Cutting edge: Role of C-C chemokine receptor 5 in organ-specific and innate immunity to *Cryptococcus neoformans*." J. Immunol. 163:4642-4646 (1999).
Johnston et al. "Radiation-induced pulmonary fibrosis: examination of chemokine and chemokine receptor families." Radiat. Res. 157:256-265 (2002).
Katchar et al. "Expression of Th1 markers by lung accumulated T cells in pulmonary sarcoidosis." J. Intern. Med. 254:564-571 (2003).
Kunkel et al. "Expression of the chemokine receptors CCR4, CCR5, and CXCR3 by human tissue-infiltrating lymphocytes." Am. J. Pathol. 160:347-355 (2002).
Luckow et al. "Reduced intragraft mRNA expression of matrix metalloproteinases Mmp3, Mmpl2, Mmpl3 and Adam8, and diminished transplant arteriosclerosis in CCR5-deficient mice." Eur. J. Immunol. 34:2568-2578 (2004).
Nissinen et al. "CCR3, CCR5, interleukin 4, and interferon-gamma expression on synovial and peripheral T cells and monocytes in patients with rheumatoid arthritis." J. Rheumatol. 30:1928-1934 (2003).
Santucci et al. "Expansion of CCR5+ CD4+ T-lymphocytes in the course of active pulmonary tuberculosis." Eur. Respir. J. 24:638-643 (2004).
Wu et al. "Interaction of chemokine receptor CCR5 with its ligands: multiple domains for HIV-1 gp120 binding and a single domain for chemokine binding." J. Exp. Med. 186:1373-1381 (1997).

* cited by examiner

*Primary Examiner* — Ilia Ouspenski
(74) *Attorney, Agent, or Firm* — Morgan, Lewis & Bockius LLP

(57) ABSTRACT

The present invention includes compositions and methods for the treatment of Th1 and/or Th2 mediated inflammatory diseases, relating to inhibiting CCR5. This is because the present invention demonstrates, for the first time, that expression of IFN-γ, IL-13, and CCR5, mediates and/or is associated with Th1 and/or Th2 inflammatory diseases and that inhibiting CCR5 treats, and even prevents, the diseases. Thus, the invention relates to the novel discovery that inhibiting CCR5 treats and prevents Th1 and/or Th2 mediated inflammatory disease.

9 Claims, 38 Drawing Sheets

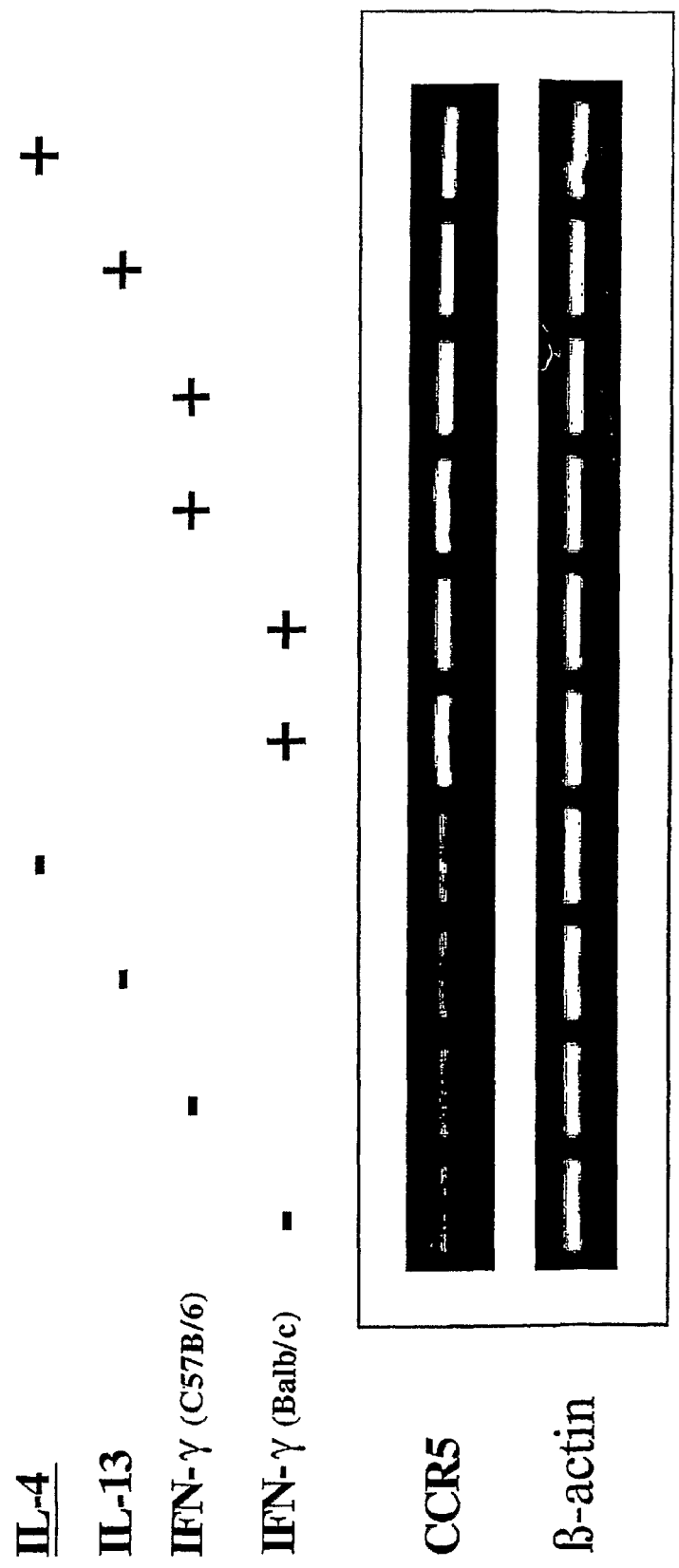

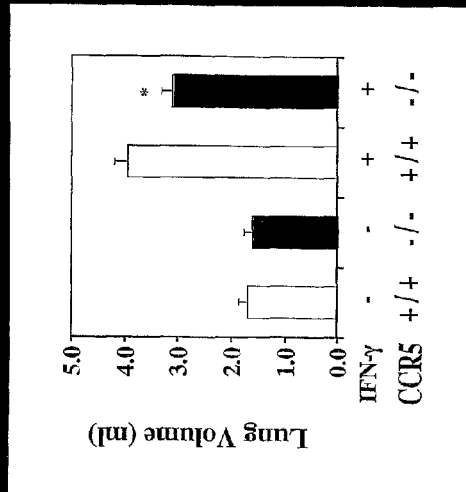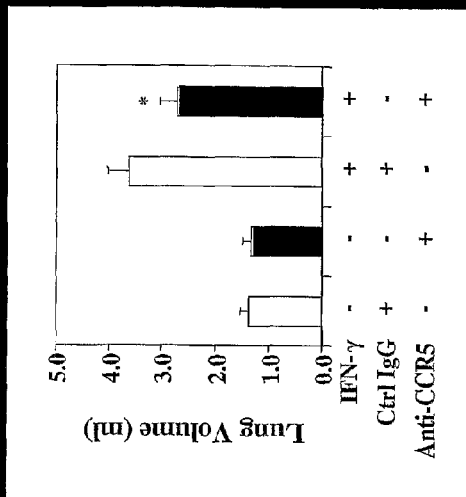

Blocking and Null Mutation of CCR5 In CC10-IFN-γ Mouse Lung
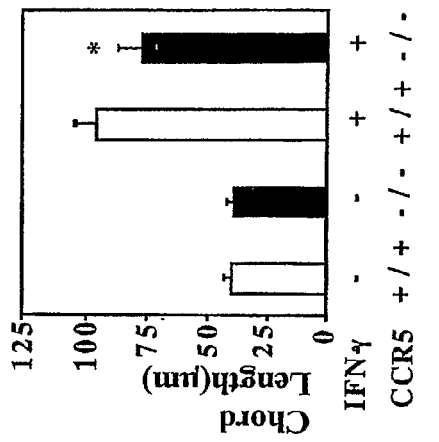
FIG. 4C
FIG. 4D
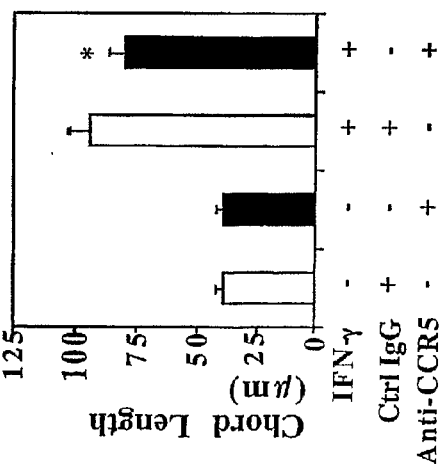
FIG. 4E
FIG. 4F

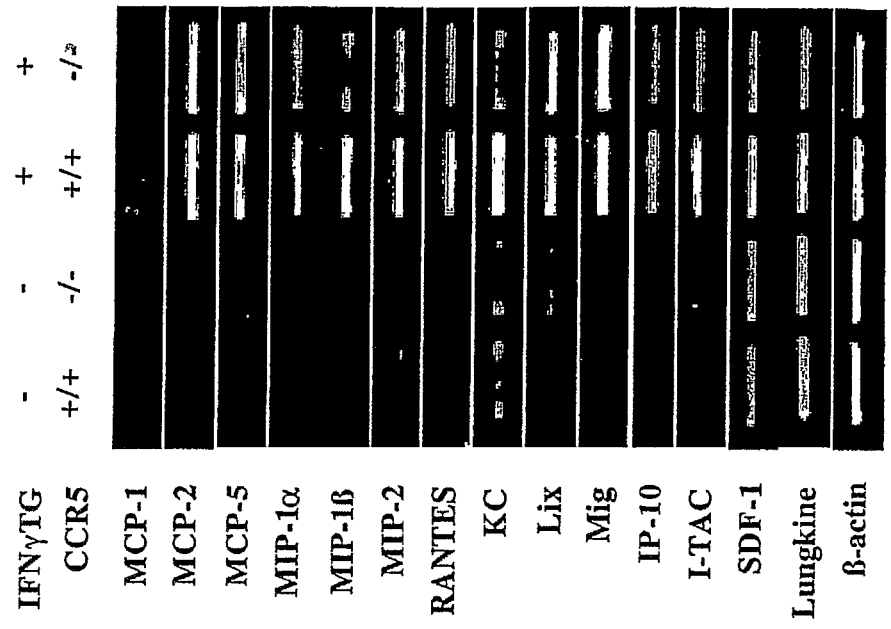
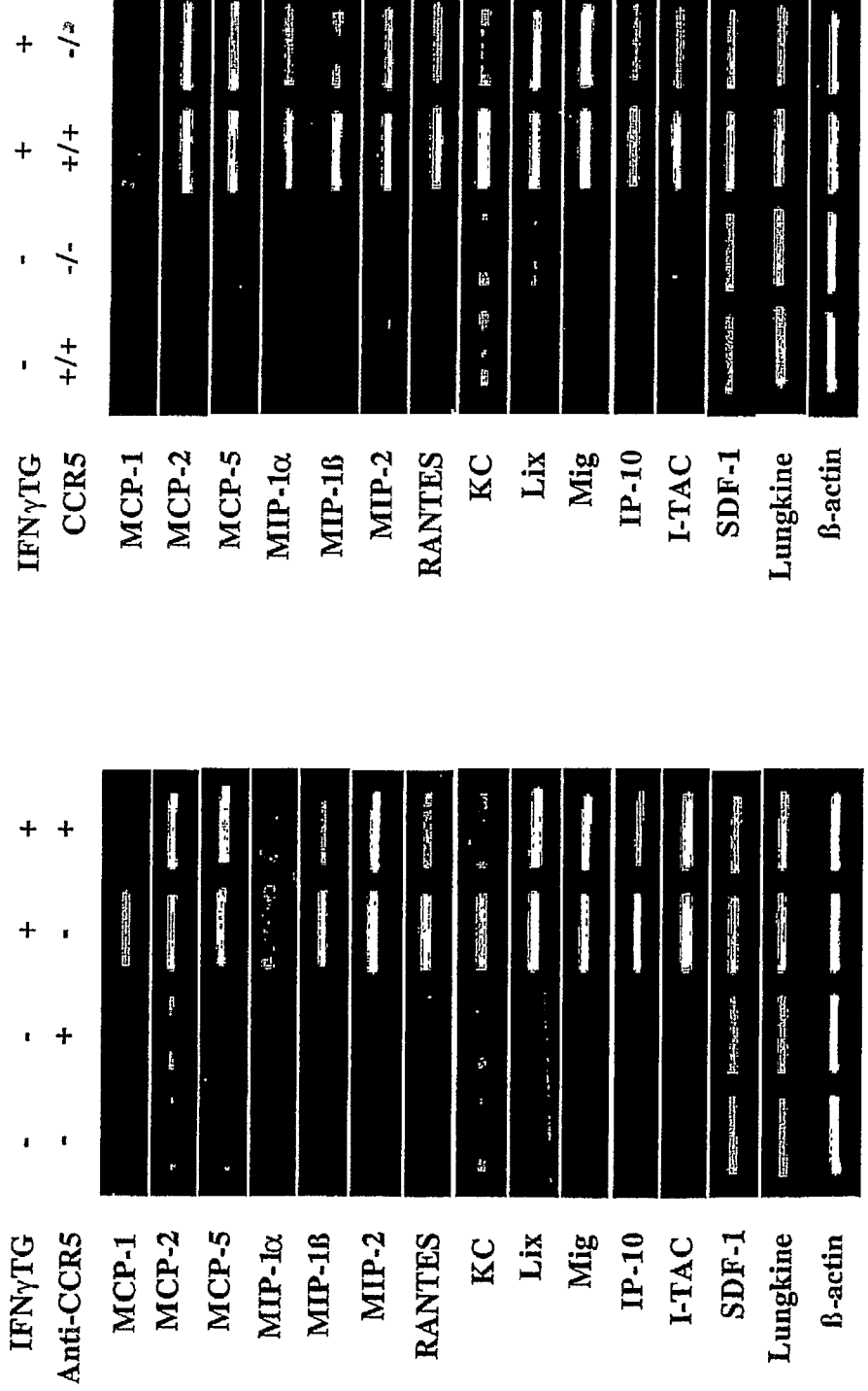

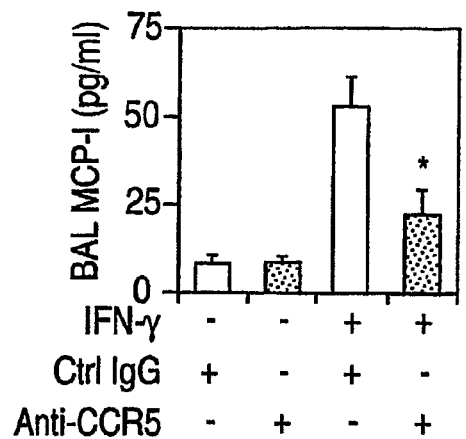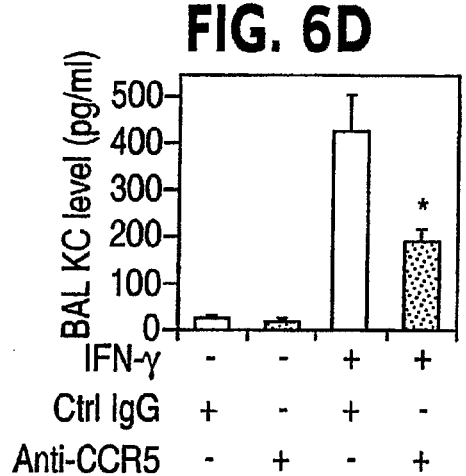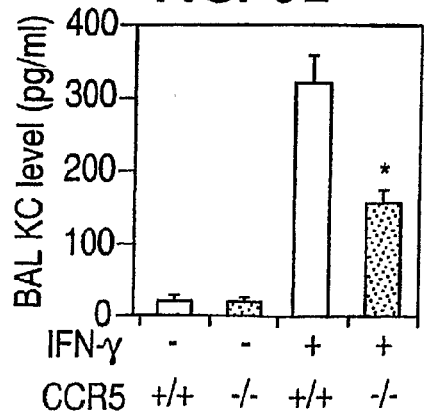

Proteinase and anti-proteinase after blocking and null mutation of CCR5 in IFN-γ mice

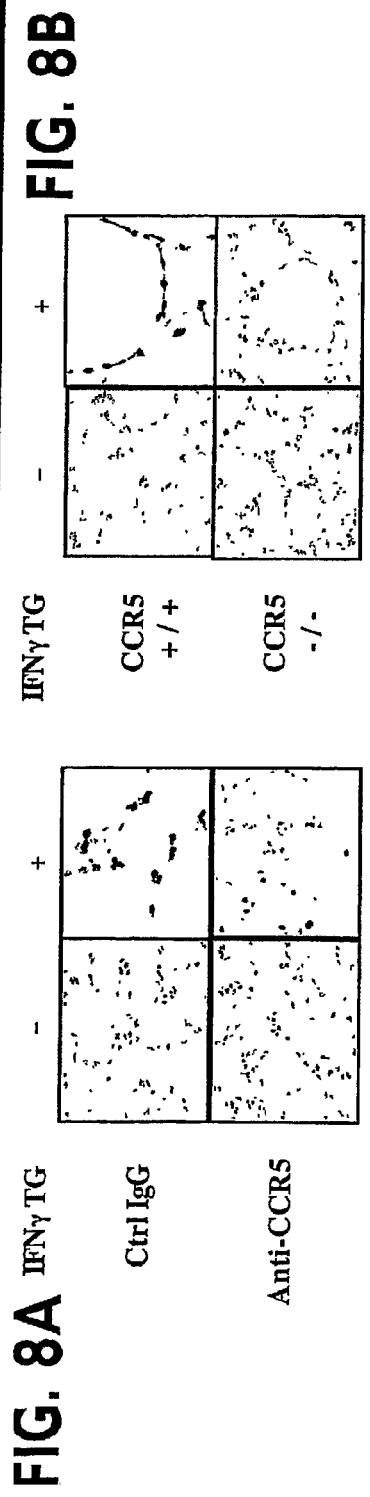
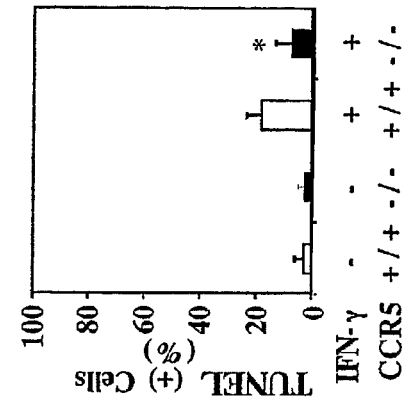
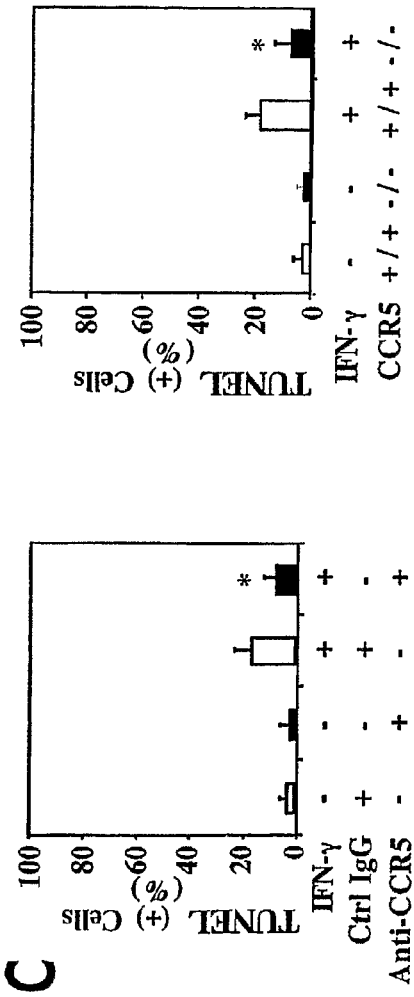
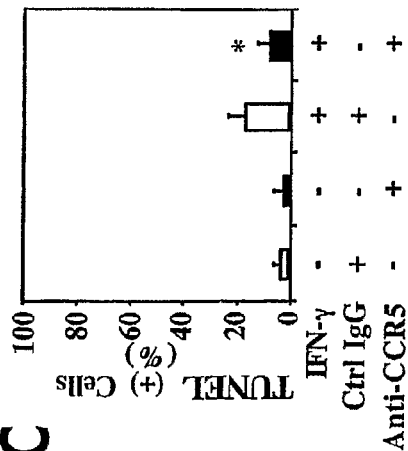

| QUAD | EVENTS | % GAINED | TOTAL |
|---|---|---|---|
| UL | 0 | 0.00 | 0.00 |
| UR | 202 | 2.15 | 2.02 |
| LL | 0666 | 95.08 | 60.65 |
| LR | 109 | 2.14 | 1.99 |

| QUAD | EVENTS | % GAINED | % TOTAL |
|---|---|---|---|
| UL | 0 | 0.00 | 0.00 |
| UR | 540 | 25.59 | 5.45 |
| LL | 923 | 45.97 | 9.23 |
| LR | 545 | 27.14 | 5.45 |

| QUAD | EVENTS | % GAINED | % TOTAL |
|---|---|---|---|
| UL | 7 | 0.12 | 0.07 |
| UR | 541 | 9.47 | 5.41 |
| LL | 41.96 | 73.45 | 41.98 |
| LR | 960 | 18.96 | 9.69 |

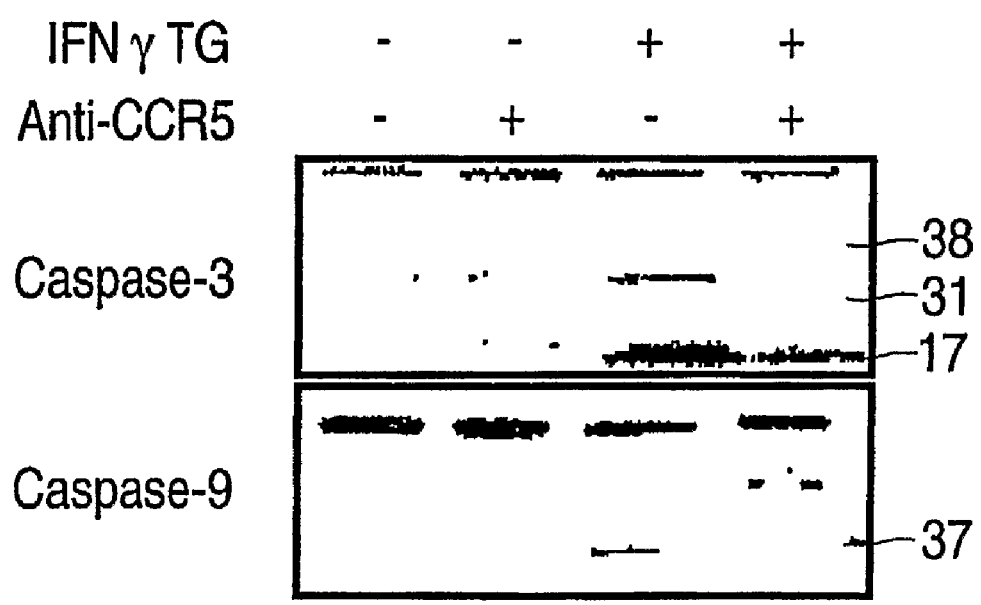

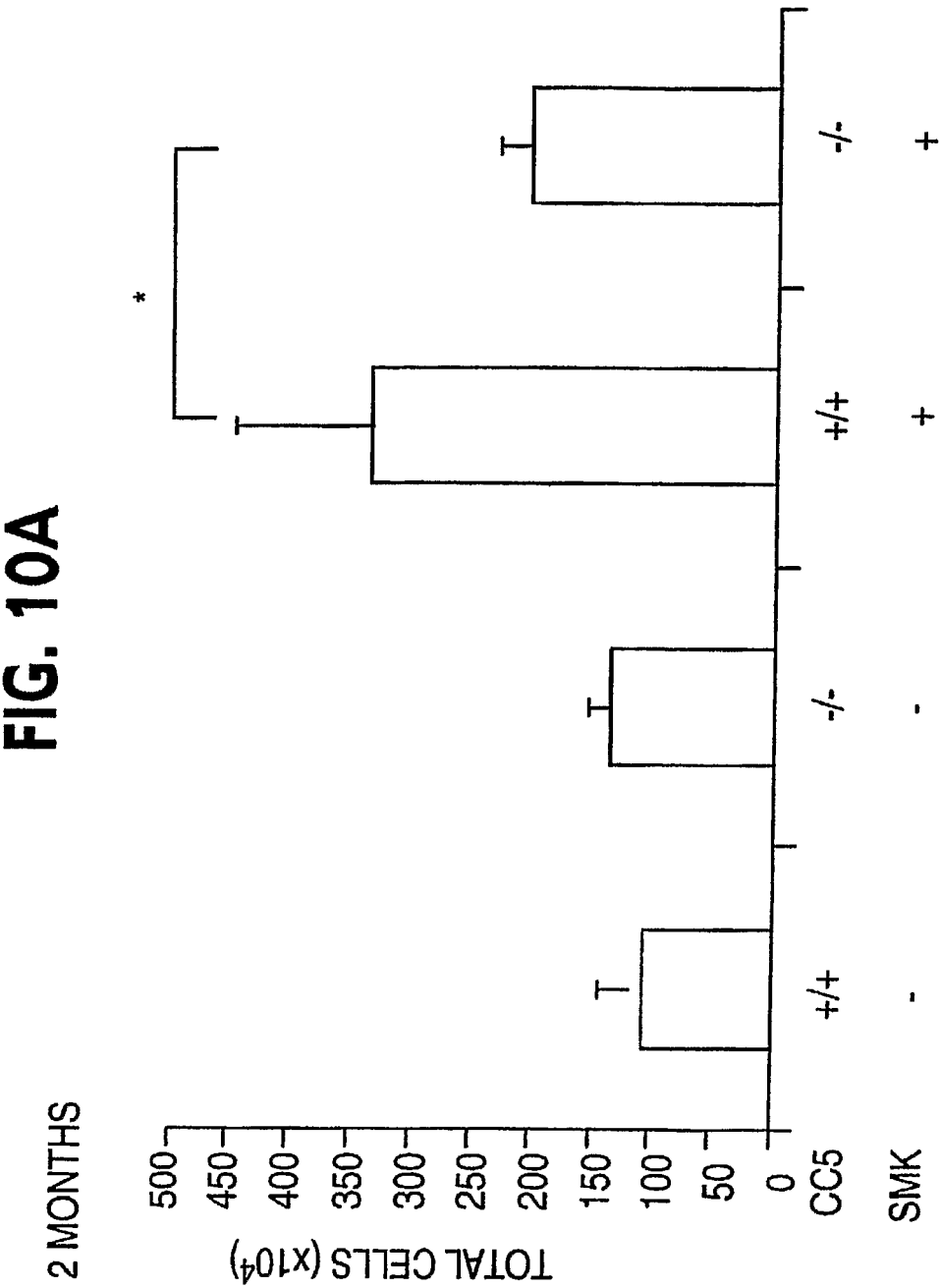

FIG. 10B
HISTOLOGY (HE) AFTER TWO MONTHS SMOKING EXPOSURE
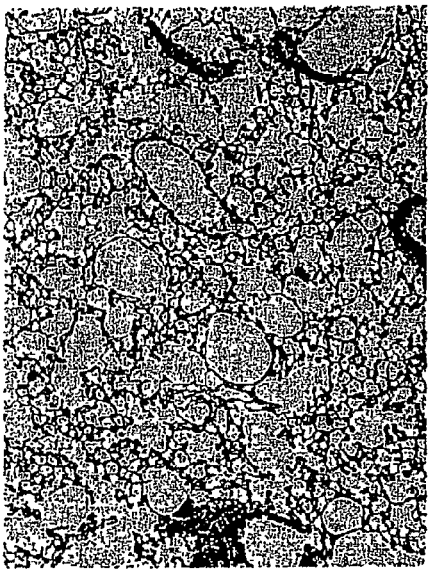
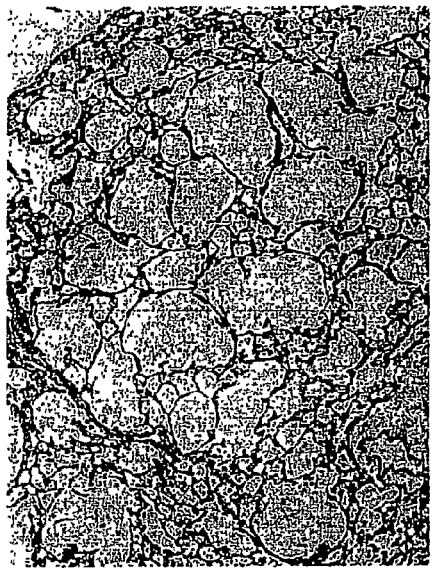
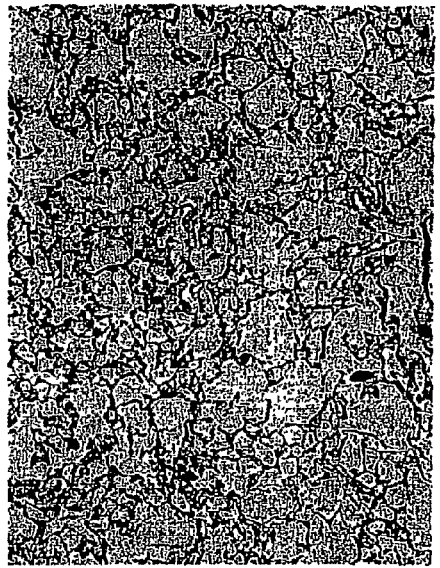

FIG. 10C
TUNEL STAINING FOR APOPTOSIS AFTER TWO MONTHS SMOKING EXPOSURE
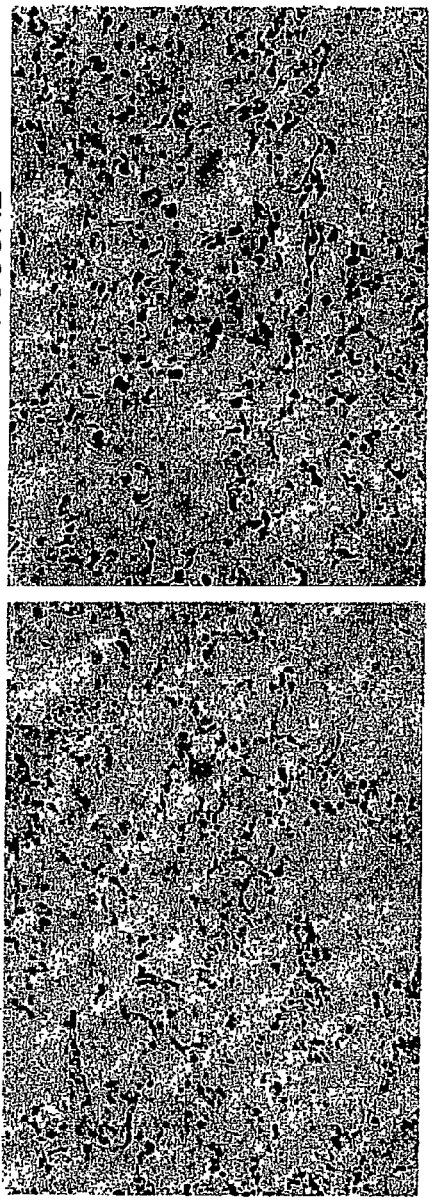
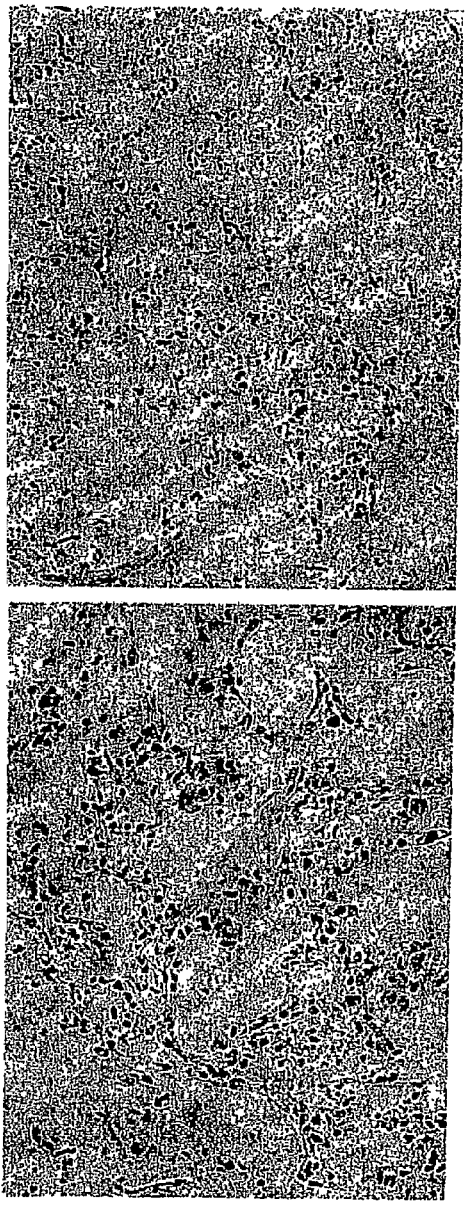

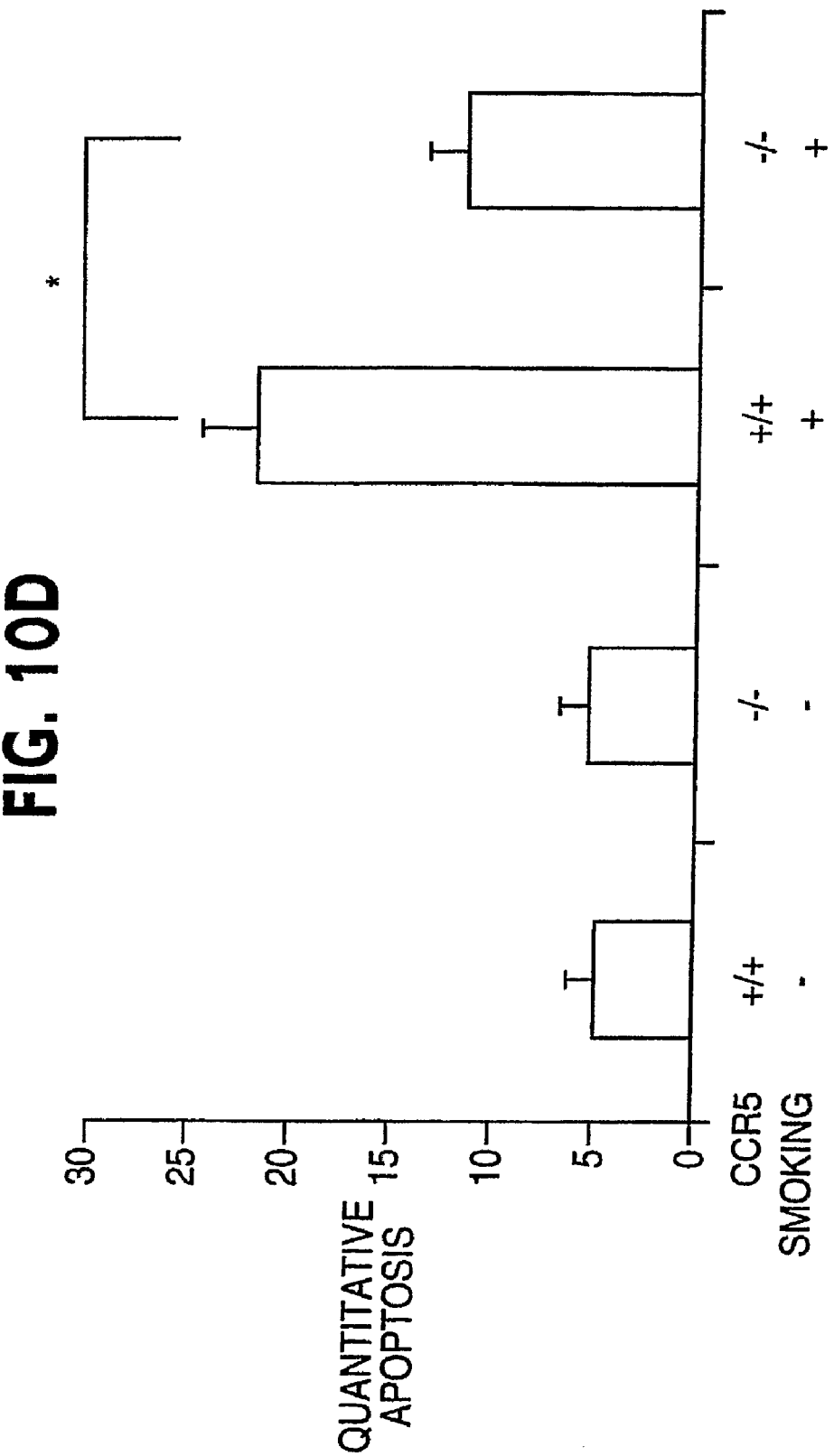

CCR5 ISH in CC10-IL-13 Mouse Lung

CCR5 IHC in CC10-IL-13 Mouse Lung

FIG. 13
Lung Volume of IL-13 Mice After block and null mutation of CCR5
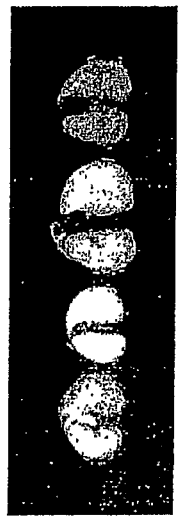
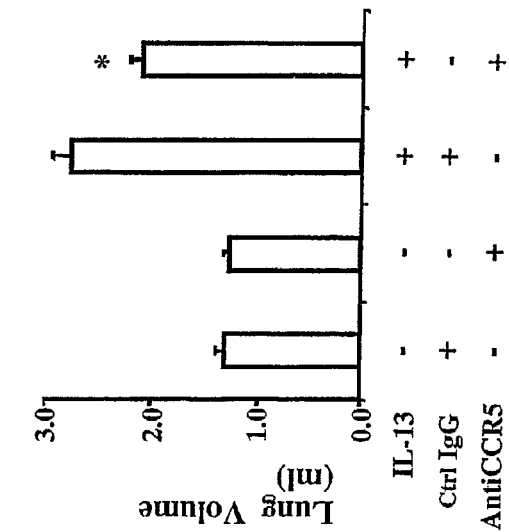
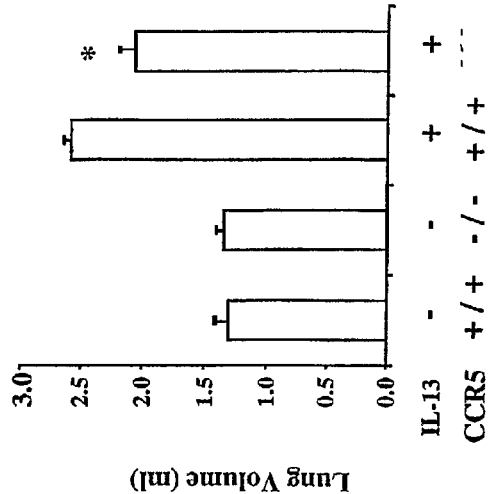

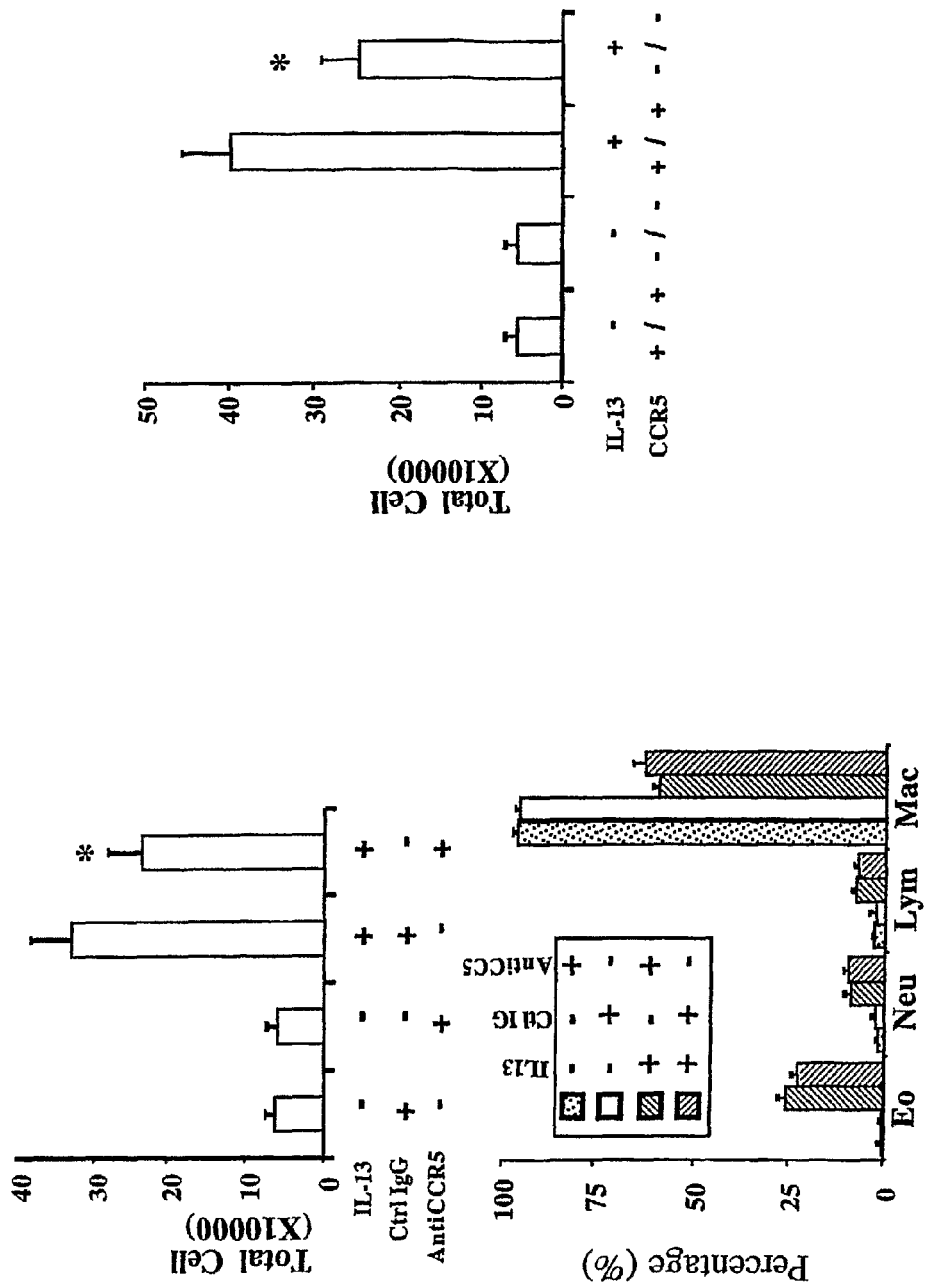
FIG. 14A  BAL total cell and differential of iIL-13 mice after block and null mutation of CCR5

BAL IL-13 Level of iIL-13 mice treated with Anti-CCR5 antibody

TUNEL Staining in iIL-13 Mouse Lung

Western Blot Detecting Apoptotic Factors in IL-13 Transgenic Mouse Lungs

FIG. 22
CCR5 IHC in CC10-IL-13 Mouse Lung
Control IgG         Anti-CCR5

IL-13 (−)
IL-13 (+)

Caspase Activities of CCR5ko/IL-13

CD8+ Cells in CC10-IFN-γ Mouse Lung

NK Cells in CC10-IFN-γ Mouse Lung

FIG. 27
DC Cells in CC10-IFN-γ Mouse Lung
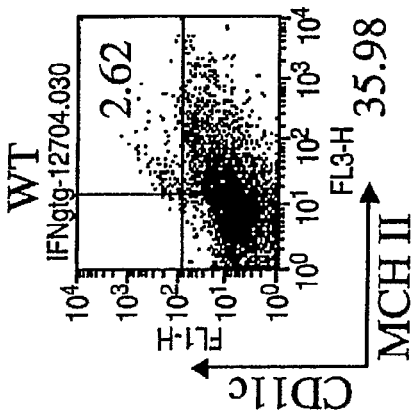
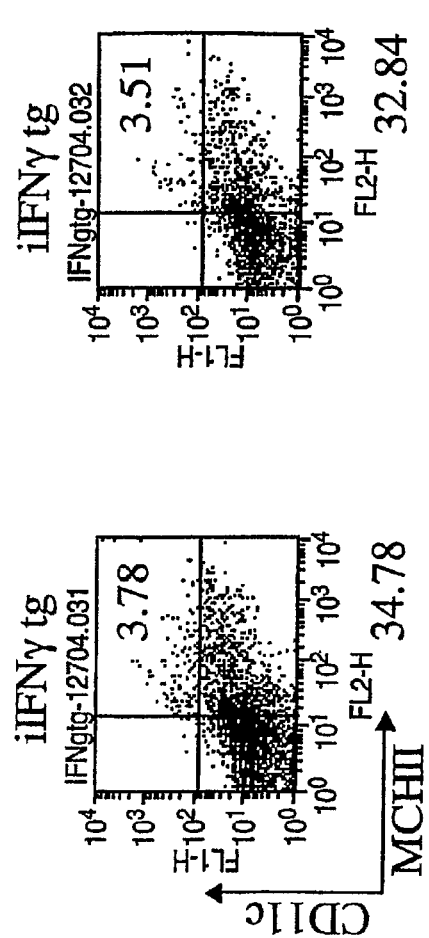

METHODS AND COMPOSITIONS RELATING TO CCR5 ANTAGONIST, IFN-γ AND IL-13 INDUCED INFLAMMATION

CROSS REFERENCE TO RELATED APPLICATIONS

This application is a continuation-in-part of U.S. patent application Ser. No. 10/582,610 (filed Sep. 20, 2007), now U.S. Pat. No. 7,943,130 which is a U.S. National Phase Application of International Application PCT/US2004/041374 (filed Dec. 13, 2004), which claims the benefit of entitled to priority pursuant to 35 U.S.C. §199(e) to U.S. provisional patent application No. 60/528,892, which was filed on Dec. 11, 2003, all of which are incorporated herein by reference in their entirety.

STATEMENT REGARDING FEDERALLY SUPPORTED RESEARCH OR DEVELOPMENT

This invention was supported in part by funds obtained from the U.S. Government (National Institutes of Health Grant Numbers HL-64242, HL-78744, HL-66571, and HL-56389) and the U.S. Government may therefore have certain rights in the invention.

BACKGROUND OF THE INVENTION

Chronic obstructive pulmonary disease (COPD) is a major cause of morbidity and mortality, ranking fourth as the leading cause of death in the United States. COPD is characterized by reduced maximum expiratory flow, which does not change over several months and which persists for 2 or more consecutive years. Patients with the most severe form of COPD generally have with a significant degree of emphysema. Emphysema is defined anatomically by permanent airspace enlargement distal to the terminal bronchioles. It is characterized by gradual loss of lung recoil, alveolar destruction, decreased alveolar surface area and gas exchange. These two features, impaired gas exchange and reduction in expiratory flow, are characteristic physiological abnormalities from which patients with emphysema suffer. The main symptom of patients with severe emphysema is shortness of breath during minimal physical activity.

The most common cause of emphysema is cigarette smoking although other potential environmental toxins may also contribute. These various toxins activate destructive processes in the lung including release of active proteases and free radical oxidants in excess of protective mechanisms. The imbalance in protease/anti-protease levels leads to destruction of the elastin matrix, loss of elastic recoil, tissue damage and continuous decline in lung function. Removing the injurious agents (i.e. quit smoking) slows the rate of damage, however, the damaged alveolar structures do not repair and lung function is not regained.

COPD is now characterized as a complex inflammatory disease attributed to the inappropriate stimulation of the immune system, especially the activation of T lymphocytes ("T-cells"). Mature T cells can be divided broadly into two functional categories by the presence of two mutually exclusive antigens on their cell surface, CD4 and CD8. While CD8+ T cells are associated with cytotoxicity functions, CD4+ T cells are associated with helper function and secrete various cytokines that regulate and modulate immune responses. CD4+ T cells can be further subdivided into T helper 1 (Th1) and T helper 2 (Th2) subsets, according to the profile of cytokines they secrete. While Th1 cells produce predominantly cytokines such as IL-2, TNF-α and IFN-γ, Th2 cells produce such cytokines as IL-4, IL-5, IL-10, and IL-13. In sum, COPD is a disease that involves various Inflammatory cells, cytokine, chemokine, and other mediators (Jaffery et al. 2001).

Studies of lung tissues of patients with COPD have found an increased number of CD8+ lymphocytes. It has also been suggested that T cells in COPD are predominately type I T cytotoxic (Tc1) cells that produce cytokines like IFN-γ (O'Shaunessey et al.; Corsio et al. 1999; Bouchet et al. 1999). Such findings are further supported by the reports that an increased number of CD3+, CD8+, and CXCR3 (+) cells producing IFN-γ and increased levels of the IFN-γ target gene, IP-10/CXC10, are found in biopsies from patients with COPD (Panzer et al., 2003; Sietta et al. 2002). In addition, studies from the inventors' laboratory demonstrated that transgenic overexpression of IFN-γ in the adult murine lung causes pulmonary emphysema.

IFN-γ is an important component of the inflammatory response and resultant pathology of those diseases exhibiting an inflammatory response. IFN-γ was originally defined based on its anti-viral capacities (Schroeder et al.). It is now, however, appreciated to be an essential immune regulator and the proteotypic Th1 cytokine that plays a key role in diverse biologic responses including pathogen recognition, antigen processing and presentation, regulation of cellular proliferation, induction of apoptosis, activation of microbicidal effector functions, immunomodulation and leukocyte trafficking (Schroeder et al.). In keeping with its important biologic effector functions and key role in Th1 immunity, dysregulated induction of IFN-γ has been implicated in a number of diseases including atherosclerosis, autoimmune disorders (Gagliardo et al.), Chron's Disease (Abreu et al.; Bouma et al.), sarcoidosis (Moeller et al.), microbacterial disease (Winn papers), celiac disease (Lund et al., 2003), rheumatoid arthritis (Chae et al., 2004; Vervoordeldunk et al., 2002), periodontal disease, Baechet's Disease (Ben Ahmed et al., 2004), apthous ulcers (Borra et al.), autoimmune gastritis (Katakai et al., 2003), glemoleftridis (Matsutoni et al., 2003) and uveoritinitis (Foxman et al.). An interesting feature of many of these responses is the close approximation of Th1 inflammation and tissue remodeling characterized by tissue atrophy and/or destruction. This is readily appreciated in the joint erosions in rheumatoid arthritis, ulcerations in Baechet's and apthous ulcers (Borra et al.; Ben Ahmed et al.), tissue remodeling in periodontal disease, ocular destruction and scarring in uveoritinitis (Foxman et al.), clarification and purification in Chron's Disease (Lund et al.; Bouma et al.), myocardial injury in myocarditis (Song et al., 2003) and renal injury in ANCA-associated glemerolinfridis (Masutani et al., 2003). In keeping with the importance of IFN-γ as an immune regulator, an impressive body of work has been dedicated to understanding the mechanisms of regulation of IFN-γ production and its immune effector functions (see review by Schroeder et al.). Surprisingly, even though it is now appreciated that Th1 responses induce tissue injury with minimal healing (Sandler et al.), the mechanisms of this injury and tissue remodeling have not been adequately investigated.

While IFN-γ is thought to be one of the major mediators in the Th1 inflammation, two prominent cytokines, IL-4 and IL-13, are believed to play an important role in the inflammation and airway remodeling of COPD through Th2 inflammatory pathway. IL-4 and IL-13 are similar in that they are both produced by the same subset of Th2 helper T cells, have overlapping effector profiles, and share a receptor component and signaling pathways. However, the critical role of IL-13 over IL-4 in AHR, eosinophil recruitment, mucus overproduction, and other symptoms of asthma has been conclusively demonstrated (Wills-Karp, 1998, Science 282:2258-2260, Grunig et al. 1998, Science 282:2261-2263). Overexpression of IL-13 in the murine lung results in eosinophil, lymphocyte, and macrophage rich inflammation, mucus metaplasia, airway fibrosis, and AHR after methacholine challenge (Zheng et al., 1999 J. Clin. Invest. 103:779-788). Further, polymorphisms in both the IL-13 promoter and the coding region have been associated with the asthmatic phenotype (Heinzmann et al., 2000, Hum. Mol. Genet. 9:549-559). These results suggest that abnormal IL-13 production is a critical component of asthmatic inflammation and airway remodeling.

The role of IL-13 in inflammatory pulmonary diseases is not limited to asthma. COPD has long been thought of as a distinct disease from asthma. However, the similarities between the two diseases have been noted and have resulted in the formulation of the "Dutch Hypothesis", that was first proposed in 1961. The most recent revision of the Dutch Hypothesis proposes that asthma and COPD, in some individuals, are not distinct processes, and that common pathogenic mechanism underlie these disorders. The hypothesis further states that a genetic predisposition to develop atopy, asthma, AHR and/or increased levels of IgE predispose cigarette smokers to develop COPD (Vestbo and Prescott, 1997, Lancet 350:1431-1434). Further, overexpression of IL-13 in the murine lung causes emphysema and COPD-like mucus metaplasia, IL-13 is overexpressed in biopsy and autopsy lung tissue from patients with COPD, and polymorphisms of IL-13 have been described that correlate with the presence of COPD. When these results are viewed in light of the Dutch Hypothesis, not only are asthma and COPD more closely related than previously thought, but the central role of IL-13 dysregulation in these pulmonary inflammatory disorders becomes more prominent.

In addition to cytokines, another class of inflammatory mediators, chemokines, are believed to also play an important role in Th1 and TH2 mediated immune and inflammatory responses. The chemokine superfamily can be divided into two main groups exhibiting characteristic structural motifs, the Cys-X-Cys (C-X-C) and Cys-Cys (C-C) families. The C-X-C chemokines include several potent chemoattractants and activators of neutrophils such as interleukin-8 (IL-8) and neutrophil-activating peptide 2 (NAP-2). The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR3, CCR4, CCR5, CCR6, CCR7, CCR8, CCR9, CCR10, CXCR1, CXCR2, CXCR3 and CXCR4. CCR5 is a receptor that binds MIP-1α/CCL3. and MIP-1β/CCL4 and RANTES/CCL5 (Allgood et al.). It is expressed on granulocytes, dendritic cells, macrophages, CD8+ cells, memory CD4+ cells and at high levels on Th1 lymphocytes (Kunkel et al., 2002; Allgood et al.). CCR5 is predominantly expressed in lymphocytes and macrophages (Wu et al., 1997; Bleul et al., 1997). CCR5 plays a critical role in Th1 inflammation and immunity where it is required for successful irradication/control of a variety of infectious agents such as tuberculosis, *Cryptococcus* and *toxoplasma* (Santucci et al.; Hoffnagle et al., 1999; Fraziano et al., 1999; Allgood et al.) and is expressed in exaggerated quantities in Th1-dominated responses including those in tuberculosis, sarcoidosis, Wegner's granulomatosis, rheumatoid arthritis, periodontitis and acute and chronic allograft rejection (Santucci et al.; Frasiano et al.; Katcher et al.; Zhu et al.; Johnston et al.; Nissin et al.; Garulet et al.; Luckow et al.). In these responses, CCR5 plays an important role in the pathogenesis of tissue inflammation and in allograft rejection. It also plays a critical role in the regulation of protease production and tissue remodeling (Luckow et al.). CCR5 may also be involved in local cell death responses and CCR5 serves as a death receptor in neural tissues (Cartier et al. 2003). Despite its frequent co-expression with IFN-γ and its important roles in inflammation, protease production and apoptosis, the role of CCR5 in the pathogenesis of IFN-γ-induced inflammation and tissue remodeling has not been formally investigated.

Because of the critical role chemokines play in various immune and inflammatory diseases, there is ongoing in the art a substantial investigation of different classes of modulators of CCR5. A representative disclosure is Mills et al. WO 98/25617 relating to substituted aryl piperazines as modulators of chemokine receptor activity. Further disclosures are: WO 98/025605; WO 98/025604; WO 98/002151; WO 98/004554; WO 97/024325, WO 00/38680, WO 00/39125, U.S. Pat. No. 6,689,783 (aryl oxime-piperazine derivatives), U.S. Pat. No. 6,689,765 (piperazine derivatives), U.S. Pat. No. 6,602,885 (piperidine derivatives), (U.S. Pat. No. 6,562,859 (pyrrole derivatives), U.S. Pat. No. 6,531,484 (pyrrolidine derivatives), U.S. Pat. No. 6,235,771 (anilide derivatives), U.S. Pat. No. 6,242,459 (bis-acridines), U.S. Pat. No. 6,515,027 (benzanilides), U.S. Pat. No. 6,528,625 (anti-CCR5 antibodies), U.S. Pat. No. 6,100,087 (Ribozymes). However, no attempts have been made to examine in vivo the potential therapeutic effects of CCR5 antagonists in Th1 and Th2 mediated diseases.

BRIEF SUMMARY OF THE INVENTION

The present invention is based on the discovery that CCR5 signaling plays an important role in the pathogenesis of IFN-γ- or IL-13 induced inflammation and tissue alterations in vivo. The invention involves expression of CCR5 and its chemokine ligands in transgenic mice in which IFN-γ or IL-13 was overexpressed in a lung-specific fashion and defined the effects of CCR5 neutralization and a null mutation of CCR5 on IFN-γ or IL-13 inflammation and remodeling in these animals. These studies demonstrate that IFN-γ or IL-13 is a potent stimulator of CCR5 and its chemokine ligands (MIP-1α/CCL-3, MIP-1β/CCL-4 and RANTES/CCL-5). They also demonstrate that CCR5 neutralization and a deficiency of CCR5 markedly ameliorate IFN-γ or IL-13 induced inflammation and remodeling. Lastly, they provide mechanistic insight by demonstrating that IFN-γ or IL-13 induces the chemokines MCP-1, MCP-5, MIP-1α/CCL-3, MIP-1β/CCL-4 and IP-10, the matrix metalloproteinase (MMP)-9 and lung cell DNA injury and apoptosis via CCR5 dependent mechanisms.

The present invention provides methods of treating or preventing Th1 or Th2 mediated diseases in a subject by administering an effective amount of chemokine receptor 5 (CCR5) antagonist to the subject. In particular, the present invention provides methods of treating COPD in smokers with such CCR5 antagonist as a chemical compound, an antibody, a ribozyme, a nucleic acid, and/or an antisense nucleic acid molecule.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A-1B, shows the effect of IFN-γ and IL-13 on CCR5 expression. FIG. 1B is an image depicting double labeled lung tissue of mice treated with control IgG and anti-CCR5 antibody.

FIG. 2, comprising

FIG. 3, comprising FIGS. 3A-3B, demonstrates the role of CCR5 in IFN-γ induced inflammation.

FIG. 4, comprising FIGS. 4A-4F, shows the role of CCR5 in IFN-γ induced alveolar remodeling and destruction. FIG. 4A shows the lung volume change of IFN-γ mice treated with and without anti-CCR5 antibody. FIG. 4B shows the lung volume change of IFN-γ mice with null mutation of CCR5. FIGS. 4C-4F show blocking and null mutation of CCR5 in CC10-IFN-γ mouse lungs.

FIG. 5, comprising

FIG. 6, comprising FIGS. 6A-6G, shows the effect of CCR5 in IFN-γ induced chemokine elaboration.

FIG. 7, comprising

FIG. 8, comprising FIGS. 8A-8G, shows the role of CCR5 in IFN-γ induced DNA injury and cell death. FIGS. 8A and 8C show TUNEL staining of the lung tissue of IFN-γ mice treated with anti-CCR5 antibody. FIGS. 8B and 8D show TUNEL staining of the lung tissue of IFN-γ mice with null mutation of CCR5.

FIG. 9, comprising FIGS. 9A-9G, shows the mechanisms of CCR5 regulation of apoptosis in IFN-γ induced inflammation. FIG. 9A shows the levels of mRNA encoding Fas, Fas-L, TNF, caspase-3, caspase-8, caspase-9, Bid and Bax.

FIG. 10, comprising FIGS. 10A-10D, shows the role of CCR5 in cigarette-smoking induced inflammation and alveolar remodeling. FIG. 10A shows BAL total cell count of IFN-γ mice either exposed or not exposed to smoking and treated with and without anti-CCR5 antibody. FIG. 10B illustrates histologic tissue from mice after two-month smoking exposure. FIG. 10C is an image of TUNEL staining of apoptosis after two-month smoking exposure. FIG. 10D shows quantitative apoptosis.

FIG. 13 shows the role of CCR5 in IL-13 induced alveolar remodeling and destruction.

FIG. 19A shows the level of mRNA encoding Fas, Fas-L, TNF, caspase-3, caspase-8, caspase-9, Bid and Bax in IL-13 mice treated with and without anti-CCR5 antibody. FIG. 19B shows the level of mRNA encoding Fas, Fas-L, TNF, capases-3, capases-8, capases-9, Bid and Bax in IL-13 mice with null mutation of CCR5.

FIG. 22 depicts immunohistochemistry of lung tissue from CC10-IL-13 mice treated with control IgG and anti-CCR5 antibody.

FIG. 27 shows DC cells in the lungs of CC10-IFN-γ mice.

DETAILED DESCRIPTION OF THE INVENTION

Figure 1B:
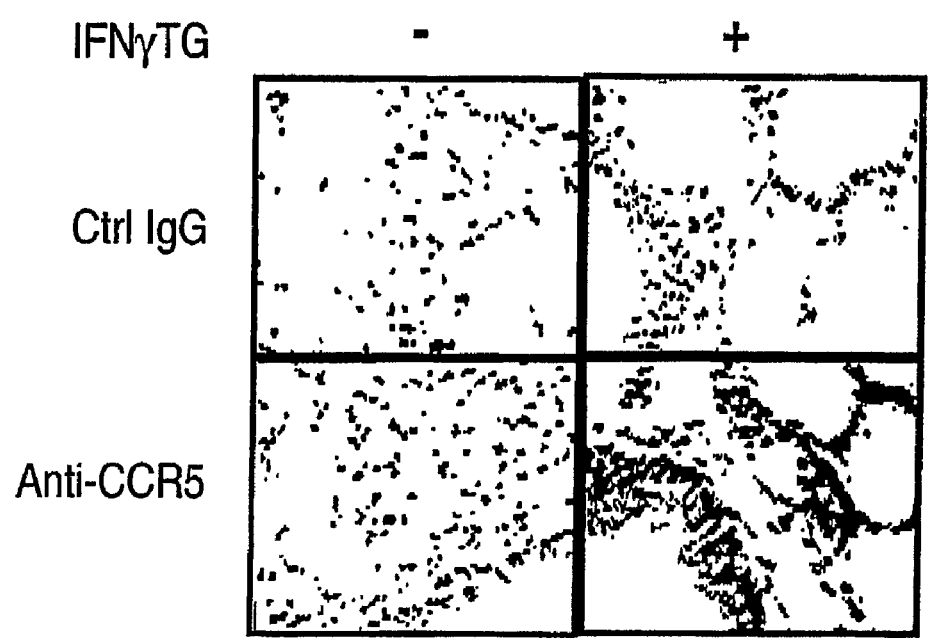

The invention includes a method of treating or preventing a Th1 and Th2 mediated disease in a mammal where the disease is associated with, or mediated by increased levels of IFN-γ and IL-13, which in turn enhance the expression level of CCR5. The method comprises administering CCR5 antagonist to the mammal. As the data disclosed elsewhere herein demonstrate, increased level of IFN-γ and IL-13, is associated with, and/or mediates an inflammatory disease including, but not limited to, asthma, COPD, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, emphysema, and the like.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

By the term "applicator" as the term is used herein, is meant any device including, but not limited to, a hypodermic syringe, a pipette, an intravenous infusion, topical cream and the like, for administering the CCR5 antagonist chemical compound, an antibody, nucleic acid, protein, and/or composition of the invention to a mammal.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand, used as the template for transcription of a gene or cDNA, can be referred to as encoding the protein or other product of that gene or cDNA.

As used herein, the term "fragment" as applied to a nucleic acid, may ordinarily be at least about 20 nucleotides in length, typically, at least about 50 nucleotides, more typically, from about 50 to about 200 nucleotides, preferably, at least about 200 to about 300 nucleotides, even more preferably, at least about 300 nucleotides to about 400 nucleotides, yet even more preferably, at least about 400 to about 500, even more preferably, at least about 500 nucleotides to about 600 nucleotides, yet even more preferably, at least about 600 to about 700, even more preferably, at least about 700 nucleotides to about 800 nucleotides, yet even more preferably, at least about 800 to about 900, even more preferably, at least about 900 nucleotides to about 1000 nucleotides, yet even more preferably, at least about 1000 to about 1100, even more preferably, at least about 1100 nucleotides to about 1200 nucleotides, yet even more preferably, at least about 1200 to about 1300, even more preferably, at least about 1300 nucleotides to about 1400 nucleotides, yet even more preferably, at least about 1400 to about 1500, at least about 1500 to about 1550, even more preferably, at least about 1550 nucleotides to about 1600 nucleotides, yet even more preferably, at least about 1600 to about 1620 and most preferably, the nucleic acid fragment will be greater than about 1625 nucleotides in length.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

An "inflammatory disease" is used herein to refer to a state in which there is a response to tissue damage, cell injury, an antigen, and/or an infectious disease. In some cases, causation will not be able to be established. The symptoms of inflammation may include, but are not limited to cell infiltration and tissue swelling. Disease states contemplated under the definition of inflammatory disease include asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids, which have been substantially purified from other components, which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

"Inducible" expression is a state in which a gene product is produced in a living cell in response to the presence of a signal in the cell.

A "recombinant polypeptide" is one, which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

As used herein, the term "transgenic mammal" means a mammal, the germ cells of which, comprise an exogenous nucleic acid.

As used herein, to "treat" means reducing the frequency with which symptoms of the inflammatory disease, are experienced by a patient, or altering the natural history and/or progression of the disease in a patient.

As used herein, the term "antisense oligonucleotide" means a nucleic acid polymer, at least a portion of which is complementary to a nucleic acid which is present in a normal cell or in an affected cell. Most preferably, the antisense oligonucleotides comprise between about fifteen and about fifty nucleotides. The antisense oligonucleotides of the invention include, but are not limited to, phosphorothioate oligonucleotides and other modifications of oligonucleotides.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "portion" of a polynucleotide means at least at least about fifteen to about fifty sequential nucleotide residues of the polynucleotide. It is understood that a portion of a polynucleotide may include every nucleotide residue of the polynucleotide.

By the term "specifically binds," as used herein, is meant an antibody which recognizes and binds CCR5, but does not substantially recognize or bind other molecules in a sample.

A "prophylactic" treatment is a treatment administered to a subject who does not exhibit signs of a disease or exhibits only early signs of the disease for the purpose of decreasing the risk of developing pathology associated with the disease.

"Preventing" a disease, as the term is used herein, means that the onset of the disease is delayed, and/or that the symptoms of the disease will be decreased in intensity and/or frequency, when CCR5 is administered compared with the onset and/or symptoms in the absence of the antagonist.

A "therapeutic" treatment is a treatment administered to a subject who exhibits signs of pathology for the purpose of diminishing or eliminating those signs.

The term "CCR5 antagonists" as used herein mean any chemical compound, antibody, ribozyme, nucleic acid, and antisense nucleic acid molecule and the like that interferes with the interaction between CCR5 and its chemokine ligands or inhibiting the expression, activity, or function of CCR5.

The term "apoptosis," as used herein, means an active process, involving the activation of a preexisting cellular pathway, induced by an extracellular or intracellular signal, causing the death of the cell. In particular, the cell death involves nuclear fragmentation, chromatin condensation, and the like, in a cell with an intact membrane.

I. Methods

A. Methods of Treating an Inflammatory Disease

The present invention includes a method of treating an inflammatory disease wherein the disease is associated with and/or induced by an increased level of IFN-γ and IL-13. Contemplated in the present invention are methods of treating an inflammatory disease in a subject, preferably a human, using CCR5 antagonist. This is because, as would be appreciated by one skilled in the art when provided with the disclosure herein, antagonism of CCR5 serves as a treatment for inflammatory diseases, including diseases mediated by IFN-γ and IL-13. That is, the data disclosed herein demonstrate that administration of CCR5 antagonist in a model of inflammatory disease associated with, or mediated by, expression of IFN-γ and IL-13, treats the disease, before, during, or after it has become established. Further, the present invention relates to the discovery that CCR5 mRNA are present in increased levels with IFN-γ and IL-13 stimulation. Thus, the present invention relates to treating of such diseases using CCR5 antagonists, including, but not limited to, CCR5 antagonist (e.g., anti-CCR5 antibody).

It would be understood by one skilled in the art, based upon the disclosure provided herein, that antagonism of CCR5 encompasses partial or complete inhibition of CCR5 expression, such as that mediated by, among other things, a ribozyme and/or antisense molecule that inhibits expression of a nucleic acid encoding CCR5. Additionally, the skilled artisan would appreciate, once armed with the teachings of the present invention, that inhibition of CCR5 includes inhibition of CCR5 activity in a cell. Such inhibition of CCR5 activity can be effected using antagonists of CCR5, including, inter alia, aryl oxime-piperazine derivatives, piperazine derivatives, piperidine derivatives, pyrrole derivatives, pyrrolidine derivatives, anilide derivatives, bis-acridines, and the like. Further, antagonists of CCR5 include an antibody that specifically binds with CCR5 thereby preventing the receptor from functioning. Thus, CCR5 antagonist includes, but is not limited to, inhibiting transcription, translation, or both, of a nucleic acid encoding CCR5.

The present invention includes a method of treating or preventing an inflammatory disease in a mammal. The method comprises administering CCR5 antagonist to a mammal in need of such treatment. This is because, as would be appreciated by one skilled in the art armed with the teachings of the present invention, inhibiting CCR5 is useful for treating or preventing an inflammatory disease. Inhibition of CCR5 prevents, in turn, the pathology associated with an inflammatory disease, as amply demonstrated by the data disclosed herein.

More specifically, the invention relates to inhibiting CCR5 using various antagonists. That is, one skilled in the art would understand, based upon the disclosure provided herein, that compounds that inhibit the expression, activity, and/or function of CCR5 encompass, but are not limited to, an antibody, an antisense nucleic acid, a ribozyme, a small molecule, a peptidomimetic and a chemical compound, either known or to be developed, which inhibits CCR5, and thereby an inflammatory disease.

One skilled in the art would appreciate, based on the disclosure provided herein, that an antagonist of the invention includes molecules and compounds that prevent or inhibit the expression, activity or function of CCR5 in a mammal. That is, the invention contemplates that an antisense and/or antisense molecule that inhibits, decreases, and/or abolishes expression of CCR5 such that CCR5 is not detectable in the cell or tissue is an antagonist of the invention.

Inhibition of CCR5 can be assessed using a wide variety of methods, including those disclosed herein, as well as methods well-known in the art or to be developed in the future. That is, the routineer would appreciate, based upon the disclosure provided herein, that inhibition of CCR5 expression can be readily assessed using methods that assess the level of a nucleic acid encoding CCR5 (e.g., mRNA) and/or the level of CCR5 present in a cell or fluid.

One skilled in the art, based upon the disclosure provided herein, would understand that the invention encompasses treatment of a variety of Th1 and Th2 inflammatory diseases, including, but not limited to, asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema, and the like. As disclosed herein, these diseases involve and/or are mediated by, increased CCR5 in tissues where increased CCR5, and is not limited to, increased CCR5 expression, increased CCR5 activity, or both.

Further, the skilled artisan would further appreciate, based upon the teachings provided herein, that the diseases to be treated encompass any disease comprising increased CCR5 expression in a tissue including, among others, a disease mediated by increased IL-13 and/or increased IFN-γ production. This is because, as more fully set forth elsewhere herein, the data disclosed herein demonstrate that increased IL-13 and/or increased IFN-γ mediates an increase in CCR5 expression which, in turns, mediates and/or is associated with a variety of changes associated with inflammatory disease including, but not limited to, tissue inflammation, increased lung volume, increased eosinophils in bronchioalveolar lavage (BAL) fluid, increased lymphocytes in BAL fluid, increased total cells in BAL fluid, increased alveolus size, increased airway resistance, increased mucus metaplasia, increased mucin expression, increased parenchymal fibrosis, increased airway remodeling, increased subepithelial fibrosis, increased collagen deposition in airway tissue, epithelial hypertrophy in the lung tissue, focal organization of crystalline material into Masson body-like fibrotic foci, and the like.

Therefore, the data disclosed herein demonstrate that partial or complete inhibition of CCR5 in a mammal afflicted with an inflammatory disease, wherein the disease is mediated or associated with increased expression of IL-13 and/or IFN-γ, will treat the disease by mediating a decrease in the level of CCR5 which, in turn, treats the disease. For instance, such data include, but are not limited to, the inhibition of various tissue pathology by administering CCR5 antagonist (e.g., anti-CCR5 antibody) to a mammal where increased expression of IL-13 and/or IFN-γ mediates increased CCR5 expression.

The present invention further comprises a method for treating an inflammatory disease mediated by and/or associated with a Th1 or Th2 inflammatory response in a mammal. The skilled artisan, when armed with the present disclosure and the teachings provided herein, would understand that an inflammatory disease mediated by and/or associated with a Th1 or Th2 inflammatory response encompasses a variety of inflammatory diseases, including, but not limited to, asthma, chronic obstructive pulmonary disease, interstitial lung disease, chronic obstructive lung disease, chronic bronchitis, eosinophilic bronchitis, eosinophilic pneumonia, pneumonia, inflammatory bowel disease, atopic dermatitis, atopy, allergy, allergic rhinitis, idiopathic pulmonary fibrosis, scleroderma, and emphysema, and the like. As disclosed herein, these diseases are mediated by a Th1 or Th2 inflammatory response in an mammal, and result in, among other things, increased IFN-γ or IL-13 production and/or expression, increased CCR5 expression.

Further, the skilled artisan would appreciate, based upon the teachings provided herein, that the diseases encompass any disease comprising increased CCR5 expression in a tissue including, among others, a disease mediated by increased Th1 or Th2 inflammatory response. This is because, as more fully set forth elsewhere herein, the data disclosed herein demonstrate that increased Th1 inflammatory responses result in, inter alia, increased IFN-γ activity and/or expression and increased Th2 inflammatory responses result in, inter alia, increased IL-13 activity and/or expression. Both events lead to an increase in CCR5 expression which, in turns, mediates and/or is associated with a variety of changes associated with inflammatory disease including, but not limited to, increased total cells in BAL fluid, increased alveolus size, increased airway resistance, increased mucus metaplasia, increased mucin expression, increased parenchymal fibrosis, increased airway remodeling, increased subepithelial fibrosis, increased eosinophils in bronchioalveolar lavage (BAL) fluid, increased lymphocytes in BAL fluid, and the like.

Therefore, the data disclosed herein demonstrate that partial or complete inhibition of CCR5 in a mammal afflicted with an inflammatory disease, wherein the disease is mediated by and/or associated with an increased Th1 or Th2 inflammatory response, will treat the disease by mediating a decrease in the level of CCR5 which, in turn, treats the disease. For instance, such data include, but are not limited to, the inhibition of various tissue pathology by administering CCR5 antagonist (e.g., anti-CCR5 antibody) to a mammal where a Th2 inflammatory response mediates increased CCR5 expression.

The present invention further comprises a method for reducing or inhibiting apoptosis implicated in the pathogenesis of alveolar remodeling in emphysema. Apoptosis, or programmed cell death, involves a wide variety of molecules. For example, the tumor necrosis family of cytokines which include such members as TNF-α, TNF-β, CD30 ligand, 4-1BB ligand, Fas ligand, and Apo-2 ligand (TRAIL) have been reported to be involved in apoptotic cell death. Caspases are another family of cysteine protease enzymes that are key mediators in the signaling pathways for apoptosis and cell disassembly (Thornberry, Chem. Biol., 1998, 5, R97-R103).

It would be understood by one skilled in the art, based upon the disclosure provided herein, that IFN-γ is a potent stimulator of apoptotic molecules such as Fas, Fas-L, TNF, caspases-3, -8, -9, Bid and Bax. Administration of a CCR5 antagonist decreases the levels of mRNA encoding Fas, Fas-L, TNF, caspases-3, -8, -9, Bid and Bax. Therefore, the skilled artisan would appreciate, once armed with the teachings of the present invention, that CCR5 antagonists may be used to inhibit or block chemokine ligands or chemokine ligands induced activities, such as chemokine ligands induced apoptosis or chemokine ligands induced lymphocyte activity, as well as suppress the proliferation of lymphocytes in response to antigenic stimulation. Based upon the mixed cytokine and chemokine assay data discussed in the Examples, it is believed that the induced immune response need not be exclusively mediated by one particular apoptotic ligand.

This inhibition or antagonist activity of CCR5 antagonist therefore has applications in diseases which are immune mediated and involve, at least as a component of their induction and mechanism, the activation of T lymphocytes which subsequently orchestrate a variety of intra- and inter-cellular events which in these diseases is deleterious to the mammal. Such immune mediated diseases which are believed to involve or rely upon T lymphocyte activation include but are not limited to asthma and other allergic diseases including for example, COPD, atopic diseases, rheumatoid arthritis and transplant related diseases including graft rejection and graft-versus-host disease.

CCR5 antagonist can include, but should not be construed as being limited to a chemical compound, a protein, a peptidomimetic, an antibody, a ribozyme, and an antisense nucleic acid molecule.

One of skill in the art would readily appreciate, based on the disclosure provided herein, that CCR5 antagonist encompasses a chemical compound that inhibits the activity of CCR5. CCR5 antagonists are well known in the art. Additionally, CCR5 antagonist encompasses a chemically modified compound, and derivatives, as is well known to one of skill in the chemical arts.

The skilled artisan would appreciate that CCR5 antagonist encompasses an already known CCR5 antagonist such as, but not limited to, aryl oxime-piperazine derivatives (see, e.g., U.S. Pat. No. 6,689,783), piperazine derivatives (see, e.g., U.S. Pat. No. 6,689,765), piperidine derivatives (see, e.g., U.S. Pat. No. 6,602,885), pyrrole derivatives (see, e.g., U.S. Pat. No. 6,562,859), pyrrolidine derivatives (see, e.g., U.S. Pat. No. 6,531,484), anilide derivatives (see, e.g., U.S. Pat. No. 6,235,771), bis-acridines (see, e.g., U.S. Pat. No. 6,242,459), and azabicycloalkanes derivatives, such as maraviroc, (International Publication No. WO 00/38680).

Further, one of skill in the art would, when equipped with this disclosure and the methods exemplified herein, appreciate that CCR5 antagonist includes such antagonists as discovered in the future, as can be identified by well-known criteria in the art of pharmacology, such as the physiological results of inhibition of CCR5 as described in detail herein and/or as known in the art. Therefore, the present invention is not limited in any way to any particular CCR5 antagonist as exemplified or disclosed herein; rather, the invention encompasses those antagonists that would be understood by the routineer to be useful as are known in the art and as are discovered in the future.

Further methods of identifying and producing CCR5 antagonist are well known to those of ordinary skill in the art, including, but not limited, obtaining an antagonist from a naturally occurring source (i.e., *Streptomyces* sp., *Pseudomonas* sp., *Stylotella aurantium*). Alternatively, CCR5 antagonist can be synthesized chemically. Further, the routineer would appreciate, based upon the teachings provided herein, that CCR5 antagonist can be obtained from a recombinant organism. Compositions and methods for chemically synthesizing CCR5 antagonists and for obtaining them from natural sources are well known in the art.

The skilled artisan would also appreciate, based on the disclosure provided herein, that CCR5 antagonist encompasses an antibody that specifically binds with CCR5 thereby blocking the interaction between CCR5 and its ligands. For instance, antibodies that specifically bind to CCR5 are well known to those of ordinary skill in the art (see, e.g., U.S. Pat. No. 6,528,625). Similarly, antibodies to CCR5 can be produced using standard methods disclosed herein or well known to those of ordinary skill in the art (Harlow et al., 1988, Antibodies: A Laboratory Manual, Cold Spring Harbor, N.Y.). Thus, the present invention is not limited in any way to any particular antibody; instead, the invention includes any antibody that specifically binds with CCR5 either known in the art and/or identified in the future.

One of skill in the art will appreciate that an antibody can be administered as a protein, a nucleic acid construct encoding a protein, or both. Numerous vectors and other compositions and methods are well known for administering a protein or a nucleic acid construct encoding a protein to cells or tissues. Therefore, the invention includes a method of administering an antibody or nucleic acid encoding an antibody (e.g., synthetic antibody) that is specific for CCR5. (Sambrook et al., 1989, Molecular Cloning: A Laboratory Manual, Cold Spring Harbor Laboratory, New York; Ausubel et al., 1997, Current Protocols in Molecular Biology, John Wiley & Sons, New York).

The skilled artisan would understand, based upon the disclosure provided herein, that the invention encompasses administering an antibody that specifically binds with CCR5 of interest, or a nucleic acid encoding the antibody, wherein the antibody molecule further comprises an intracellular retention sequence such that the antibody binds with CCR5 and prevents its expression at the cell surface and/or its export from a cell. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11-17). Thus, the invention encompasses methods comprising blocking the binding of CCR5 ligands to CCR5 or inhibiting expression of CCR5 on a cell, where the skilled artisan would understand such inhibition would provide a benefit based upon the disclosure provided herein.

The present invention is not limited to chemical compounds and antibodies against CCR5. One of skill in the art would appreciate that inhibiting the expression of a polypeptide is likewise an effective method of inhibiting the activity and function of the polypeptide. Thus, a method is provided for the inhibition of CCR5 by inhibiting the expression of a nucleic acid encoding CCR5. Methods to inhibit the expression of a gene are well known to those of ordinary skill in the art, and include the use of ribozymes or antisense oligonucleotide.

Antisense oligonucleotides are DNA or RNA molecules that are complementary to some portion of an mRNA molecule. When present in a cell, antisense oligonucleotides hybridize to an existing mRNA molecule and inhibit translation into a gene product Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931).

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, reduction or inhibition of a gene expressing CCR5 can be accomplished through the use of a RNA interference (RNAi). As is well known to those skilled in the art, this is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., Nature (1998) 391(19):306-311; Timmons et al., Nature (1998) 395:854; Montgomery et al., TIG (1998) 14(7):255-258; David R. Engelke, Ed., RNA Interference (RNAi) Nuts & Bolts of RNAi Technology, DNA Press (2003); and Gregory J. Hannon, Ed., RNAi A Guide to Gene Silencing, Cold Spring Harbor Laboratory Press (2003). Therefore, the present invention also includes methods of silencing the gene encoding CCR5 by using RNAi technology.

Alternatively, reduction or inhibition of a gene expressing CCR5 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). In addition, ribozymes that are targeted to human CCR5 mRNA have been shown in the art (see, e.g., U.S. Pat. No. 6,100,087).

One of skill in the art will appreciate that antagonists of CCR5 gene expression can be administered singly or in any combination thereof. Further, CCR5 antagonists can be administered singly or in any combination thereof in a temporal sense, in that they may be administered simultaneously, before, and/or after each other. One of ordinary skill in the art will appreciate, based on the disclosure provided herein, that CCR5 antagonists to reduce or inhibit gene expression can be used to treat asthma, COPD, and other inflammatory diseases and that an antagonist can be used alone or in any combination with another antagonist to effect a therapeutic result.

B. Method of Preventing an Inflammatory Disease

It will be appreciated by one of skill in the art, when armed with the present disclosure including the methods detailed herein, that the invention is not limited to treatment of an inflammatory disease once the disease is established. Particularly, the symptoms of the disease need not have manifested to the point of detriment to the mammal; indeed, the disease need not be detected in a mammal before treatment is administered. That is, significant pathology from an inflammatory disease does not have to occur before the present invention may provide benefit. Therefore, the present invention, as described more fully herein, includes a method for reducing or preventing an inflammatory disease in a mammal, in that CCR5 antagonist, as discussed previously elsewhere herein, can be administered to a mammal prior to the onset of an inflammatory disease, thereby preventing the disease as demonstrated by the data disclosed herein.

One of skill in the art, when armed with the disclosure herein, would appreciate that the reduction or prevention of inflammatory disease encompasses administering to a mammal CCR5 antagonist as a preventative measure against inflammatory disease. As detailed herein, the symptoms and etiologies of IL-13 and IFN-γ associated inflammatory disease include tissue inflammation, increased lung volume, increased eosinophils in bronchioalveolar lavage (BAL) fluid, increased lymphocytes in BAL fluid, increased total cells in BAL fluid, increased alveolus size, increased airway resistance, increased mucus metaplasia, increased mucin expression, increased parenchymal fibrosis, increased airway remodeling, increased subepithelial fibrosis, increased collagen deposition in airway tissue, epithelial hypertrophy in the lung tissue, focal organization of crystalline material into Masson body-like fibrotic foci, and the like. Given these etiologies and the methods disclosed elsewhere herein, the skilled artisan can recognize and reduce or prevent an inflammatory disease in a mammal using CCR5 antagonist before the disease pathology can be detected. This is because the data disclosed herein demonstrate that administration of CCR5 antagonist prevented onset of an inflammatory disease in a mammal, whether the disease was induced by an allergen (e.g. ovalbumin sensitization) or whether the mammal was genetically predisposed to the disease (e.g., transgenic mice constitutively or inducibly overproducing IL-13 and/or IFN-γ). Accordingly, the skilled artisan would appreciate, based on the disclosure provided elsewhere herein, that the present invention includes a method of preventing disease comprising inhibiting CCR5 using CCR5 antagonist. Further, as more fully discussed elsewhere herein, methods of inhibiting CCR5 encompass a wide plethora of techniques for inhibiting not only CCR5 activity, but also for inhibiting expression of a nucleic acid encoding CCR5. Additionally, as disclosed elsewhere herein, one skilled in the art would understand, once armed with the teaching provided herein, that the present invention encompasses a method of preventing a wide variety of diseases where expression and/or activity of CCR5 mediates the disease. Methods for assessing whether a disease relates to over expression or increased activity of CCR5 are disclosed elsewhere herein and/or are well-known in the art. Further, the invention encompasses treatment or prevention of such diseases discovered in the future.

The invention further encompasses methods for treating an IFN-γ and/or IL-13 mediated inflammatory disease. This is because, as the data disclosed herein demonstrate, IFN-γ and IL-13 overexpression in the lungs, among other tissues, whether inducible or constitutive, mediates or is associated with the increased expression of CCR5 in respiratory tissues, leading to, among other things, the pathologies described elsewhere herein. Thereby, the present invention includes methods of treating an IFN-γ and/or IL-13 mediated inflammatory disease using the methods of the present invention.

The invention encompasses administration of CCR5 antagonist to practice the methods of the invention; the skilled artisan would understand, based on the disclosure provided herein, how to formulate and administer the appropriate CCR5 antagonist to a mammal. Indeed, the successful administration of CCR5 antagonists have been extensively reduced to practice as exemplified herein. However, the present invention is not limited to any particular method of administration or treatment regimen. This is especially true where it would be appreciated by one skilled in the art, equipped with the disclosure provided herein, including the extensive reduction to practice using an art-recognized model of inflammatory disease, that methods of administering CCR5 antagonist can be readily determined by one of skill in the pharmacological arts.

More specifically, the data disclosed herein demonstrate that increased expression of IFN-γ and IL-13 mediates or is correlated with increased level of CCR5 and its chemokine ligands and that blocking CCR5 using, among other things, an antibody that specifically binds with CCR5, prevents, ameliorates, and/or treats inflammatory disease. That is, for instance, CCR5 is expressed at a greater level in inflammatory disease cells and/or tissues and administration of antibody that specifically binds with CCR5 treats the disease in an art-recognized animal model of inflammatory disease. Further, the data disclosed herein demonstrate similar results relating to expression of CCR5 and inhibition of CCR5 using an anti-CCR5 antibody.

C. Pharmaceutical Compositions

As used herein, the term "pharmaceutically-acceptable carrier" means a chemical composition with which an appropriate CCR5 molecule antagonist may be combined and which, following the combination, can be used to administer the appropriate CCR5 antagonist to a mammal.

The pharmaceutical compositions useful for practicing the invention may be administered to deliver a dose of between about 0.1 ng/kg/day and 100 mg/kg/day.

Pharmaceutical compositions that are useful in the methods of the invention may be administered systemically in oral solid formulations, ophthalmic, suppository, aerosol, topical or other similar formulations. In addition to the appropriate CCR5 antagonist, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate CCR5 antagonist according to the methods of the invention.

Compounds which are identified using any method described herein as potential useful compounds for treatment and/or prevention of a disease of interest can be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats and dogs, and birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXPERIMENTAL EXAMPLES

The invention is now described with reference to the following examples. These examples are provided for the purpose of illustration only and the invention should in no way be construed as being limited to these examples but rather should be construed to encompass any and all variations which become evident as a result of the teaching provided herein.

The materials and methods used in the experiments presented in this Example are now described.

General Methods

Generation of Transgenic Mice

Transgenic mice (CC10-rtTA-IL-13 and CC10-rtTA-IFN-γ) that had been generated and reported by the present inventors were used in the studies. These are dual transgene positive animals in which the reverse tetracycline transactivator (rtTA) drives the expression of the murine IFN-γ gene in a lung-specific and externally regulatable fashion. The transgene in these mice is activated by adding doxycycline (dox) to the animal's drinking water. On a Balb/c background these mice get emphysema after 2 weeks of doxycycline administration. On a C57Bl/6 background these mice get emphysema after 4-6 weeks on doxycycline. Thus, mice bred for at least 10 generations onto a Balb/c or C57Bl/6 background were employed. These mice were maintained as dual transgene (+) heterozygotes (hereinafter "Tg(+)"). The details of both genetic constructs, the methods of microinjection and genotype evaluation, the inducibility and the emphysematous and inflammatory phenotype of CC10-rtTA-IFN-γ mice have been previously described.

CCR5 null mutant (−/−), generated by W. Kuziel and colleagues, were obtained from the Jackson Labs (Bar Harbor, Me.) after breeding for more than 10 generations onto a C57BL/6 background. CC10-rtTA-IFN-γ mice with wild-type (+/+) or null (−/−) CCR5 loci were generated by breeding the IFN-γ overexpressing mice with the CCR5 (−/−) animals. PCR was used to define the transgenic status of all offspring, using primers that detected rtTA and/or the junction region of murine IFN-γ human growth hormone construct. The CCR5 loci were evaluated by PCR using primers; upper; 5'-attctccacaccctgtttcg-3' (SEQ ID NO: 1) and lower; 5'-gttctcctgtggatcgggta-3 (SEQ ID NO: 2) which detects a 388 bp reaction product.

Human Lung Immunohistochemistry

Tissue sections were deparaffinized, subject to microwave treatment in pH 6 antigen retrieval buffer for 20 minutes and then treated with protein block (2% normal horse serum, 1% bovine serum albumin in PBS) for 30 minutes. Two different anti-cathepsin S antibodies were used with identical results. One was a goat anti-cathepsin S described above. The other was a mouse monoclonal antibody (Clone IE3, mouse $IgG_1$). The use and specificity of these antibodies is well accepted. The sections stained with the anti-serum were developed with biotinylated rabbit anti-goat anti-serum (Santa Cruz) followed by streptavidin-alkaline phosphatase and Vector Red (Vector Corp, Burlingham, Calif.). The monoclonal was developed using biotinylated rabbit anti-mouse followed by streptavidin-alkaline phosphatase with Vector Red substrate. In selected experiments, specificity was confirmed by incubating the primary antibody and tissue in the presence and absence of excess unlabeled cathepsin S immunogen.

Sections were scored on a 0-4 scale based on a global assessment of staining by a pathologist blinded to the clinical information associated with each slide with zero being no staining and 4 being strong diffuse staining. Two assessments were done for each patient. In all cases, the scores were either the same or within one point of each other.

Statistics

Normally distributed data are expressed as mean±SEM and were assessed for significance by Student's T test or ANOVA as appropriate. Data that were not normally distributed were assessed for significance using the Wilcoxon rank sum test for groups of two, or the Kruskal-Wallis statistic for groups of three (human tissue results). Statistical analysis was performed using Stata (version 7.0) and Deltagraph. Statistical significance was defined at a level of $p<0.05$.

Example 1

Effect of IFN-γ on CCR5 and its Chemokine Ligands

In this example, CC10-rtTA-IFN-γ mice and littermate controls were maintained on normal water until they were 4-6 weeks old. They were then randomized to normal water or water with dox water as previously described.

mRNA Analysis mRNA levels of the mice were assessed using reverse-transcriptase polymerase chain reaction (RT-PCR). In the RT-PCR assays, gene-specific primers were used to amplify selected regions of each target moiety. The primers for the targeted genes are detailed in Table 1.

In selected experiments ribonuclease protection was also used. These assays were undertaken with mAPO-1, mAPO-2 and mAPO-3 multiprobe kits (BD PharMingen, San Diego, Calif.) as per the manufacturer's instructions.

alkaline phosphatase and Vector Red (Vector Laboratories, Burlingam, Calif.) as substrate. For caspase 3 staining, primary antibody (Cell Signaling, Inc., Tarrytown, N.Y.) was used after microwave antigen retrieval using Dako pH 6 antigen retrieval solution (Dako USA, Inc., Carpenteria, Calif.) followed by Powervision polymerized anti-rabbit peroxidase (ImmunoVision Technologies, Daly City, Calif.) and diaminobenzidine as substrate.

In selected experiments, TUNEL evaluations and immunohistochemistry for surfactant aproprotein-C (SP-C) were

TABLE 1

Primer sequence and RT-PCR conditions used in the experiment

| Gene | S/AS | Primer sequence (5' to 3') | Anneal Tm | Cycles | BP | SEQ ID NO. |
|---|---|---|---|---|---|---|
| KC | S1 | ctgggattcacctcaagaacat | 60 | 30 | 173 | 3 |
|  | AS1 | ttacttgggacaccttttagc |  |  |  | 4 |
| Lix | S1 | ctgcccttcctcagtcata | 60 | 30 | 249 | 5 |
|  | AS1 | gtgcattccgcttagctttc |  |  |  | 6 |
| MIG | S1 | tcttcctggagcagtgtgg | 60 | 30 | 196 | 7 |
|  | AS1 | tccggatctaggcaggttt |  |  |  | 8 |
| IP-10 | S1 | aagtgctgccgtcattttct | 60 | 30 | 186 | 9 |
|  | AS1 | gtggcaatgatctcaacacg |  |  |  | 10 |
| SDF-1 | S1 | gctctgcatcagtgacggta | 60 | 30 | 184 | 11 |
|  | AS1 | taatttcgggtcaatgcaca |  |  |  | 12 |
| I-TAC | S1 | ctgctcaaggcttccttatgtt | 60 | 30 | 167 | 13 |
|  | AS1 | cctttgtcgtttatgagccttc |  |  |  | 14 |
| BLC | S1 | tctggaagcccattacacaa | 60 | 30 | 188 | 15 |
|  | AS1 | tttgtaaccatttggcacga |  |  |  | 16 |
| MIP-2g | S1 | aagctggaaatgaagccaaa | 60 | 30 | 159 | 17 |
|  | AS1 | cttctcgttccaggcattgt |  |  |  | 18 |
| Lungk | S1 | cgtccctgtgacactcaaga | 60 | 30 | 205 | 19 |
|  | AS1 | taattgggccaacagtagcc |  |  |  | 20 |
| SOCS1 | S1 | gagctgctggagcactacg | 60 | 30 | 160 | 21 |
|  | AS1 | cacggagtaccgggttaaga |  |  |  | 22 |
| SOCS3 | S1 | gactgtgtactcaagctggtgc | 60 | 30 | 185 | 23 |
|  | AS1 | ctcagtaccagcggaatcttct |  |  |  | 24 |
| IL-25 | S1 | cggaggagtggctgaagtggag | 60 | 30 | 313 | 25 |
|  | AS1 | ctcagtaccagcggaatcttct |  |  |  | 26 |
| Neo | S2 | acaacaacaatcggctgctctgatg | 65 | 35 | 457 | 27 |
|  | AS2 | tgcgcgccttgagcctggcgaac |  |  |  | 28 |

S = Sense; AS = antisense

Histologic Analysis

Mice were sacrificed by cervical dislocation and a median sternotomy was performed. The right heart was perfused with calcium and magnesium free phosphate buffered saline (PBS). The heart and lungs were removed en bloc, and the lungs were fixed to 25 cm pressure with neutral buffered 10% formalin. They were then fixed overnight in 10% formalin, embedded in paraffin, sectioned at 5 μm, and stained. Hematoxylin and eosin (H & E), Mallory's trichrome, periodic acid-Schiff with diastase (D-PAS), alcian blue at pH 2.5, PAS/alcian blue, modified Congo red, and Papanicolau stains were used for histological analysis.

Mouse Lung Immunohistochemistry

Immunohistochemistry was undertaken using modifications of protocols previously described by the present inventors. CCR5 was detected using CKR5 antibody. It was followed by biotinylated anti-goat antibody, streptavidin-simultaneously undertaken. In these experiments, slides were deparaffinized with xylene and graded ethanol and taken to water. Microwave antigen retrieval was done with Dako pH 6 antigen retrieval solution, slides were treated with Dako protein block and rinsed. TUNEL (Roche) staining was then undertaken as described above and developed with alkaline phosphotase/BCIP/NBT (blue). Afterwards, tissue was counterstained with goat anti-SP-C (Santa Cruz), anti-CD3, anti-CD31 or anti-Mac-1 overnight and developed with biotinylated anti-goat/streptavidin peroxidase/AEC (red).

Results

The experiments demonstrated that IL-13 and IFN-γ are potent stimulators of CCR5 mRNA accumulation. This effect was seen after as little as 3 days of dox administration and continued throughout the 3 month assessment interval (FIG. 1A). In all cases, immunohistochemistry revealed comparable increases in tissue CCR5 protein (FIG. 1B). Double labeling immunohistochemistry demonstrated that this enhanced CCR5 expression could be appreciated on macrophages (Mac-1) (+), endothelial cells (CD31) (+), T cells (CD3+) and CD8 cells. In all cases, this staining was appropriately specific since it was not present when IHC was performed in the absence of primary antibody (data not shown). These studies demonstrate that IL-13 and IFN-γ are potent stimulators of CCR5 on macrophages, endothelial cells, T cells and CD8+ cells in the murine lung.

Figure 2A:
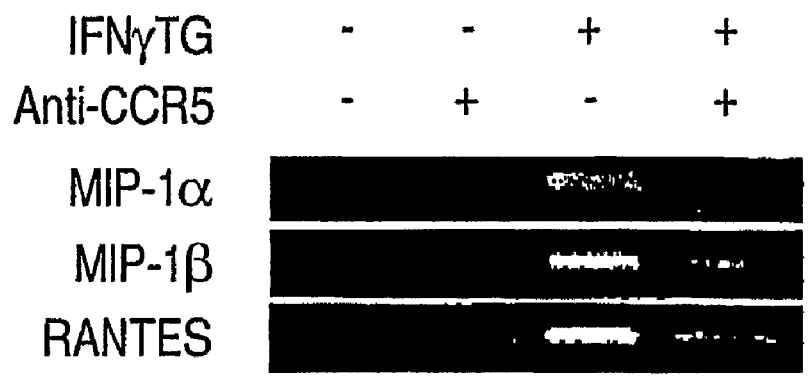
FIGS. 2A-2B, shows the effect of IFN-γ on chemokine ligands expression and the inhibitory effect of anti-CCR5 antibody on IFN-γ induced CCR5 expression.
Figure 2B:
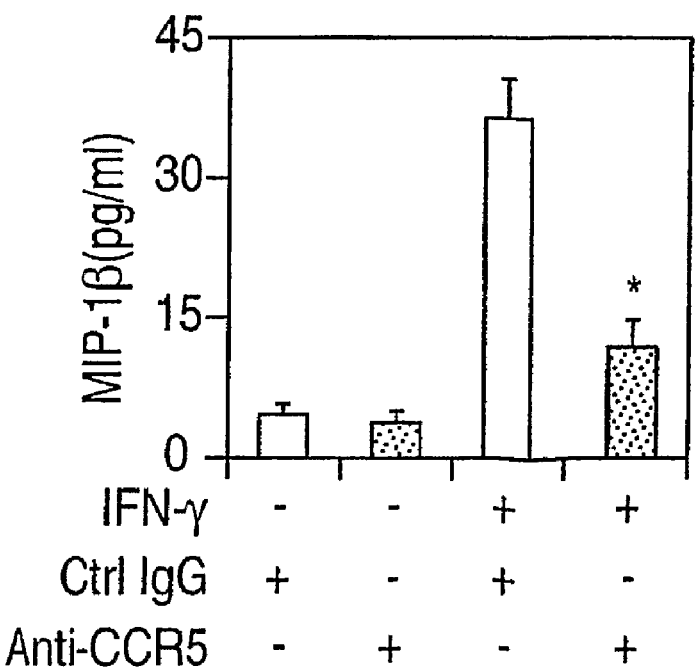

Studies were next undertaken to define the effects of IFN-γ on the chemokine ligands of CCR5. The levels of mRNA encoding MIP-1α/CCL-3, MIP-1β/CCL-4 and RANTES/CCL5 were near or below the limits of detection with our assays. In contrast, the levels of mRNA encoding all three of these chemokines were impressively increased by transgenic IFN-γ. These effects could be appreciated after as little as 3 days of IFN-γ elaboration and persisted throughout the 3 month study interval (FIG. 2). They were also associated with impressive increases in BAL chemokine protein levels at all time points. Taken together, these studies demonstrate that IFN-γ is a potent stimulator of CCR5 and its chemokine ligands in the murine lung.

Example 2

Role of CCR5 in IFN-γ Induced Inflammation

To further determine the role of CCR5 in IFN-γ induced inflammation, four to six week old Balb/c transgene (−) and transgene (+) mice were randomized to receive rat monoclonal anti-CCR5 (Research Diagnostics Inc., Flanders, N.J.) or isotype control (rat IgG2c) immunoglobulin (500 μg IP qod). Two days later they were randomized to normal or dox water and maintained on this regimen for 10 days. At the end of this interval, the animals were sacrificed and pulmonary phenotype was assessed as described below.

Figures 3A, 3B:
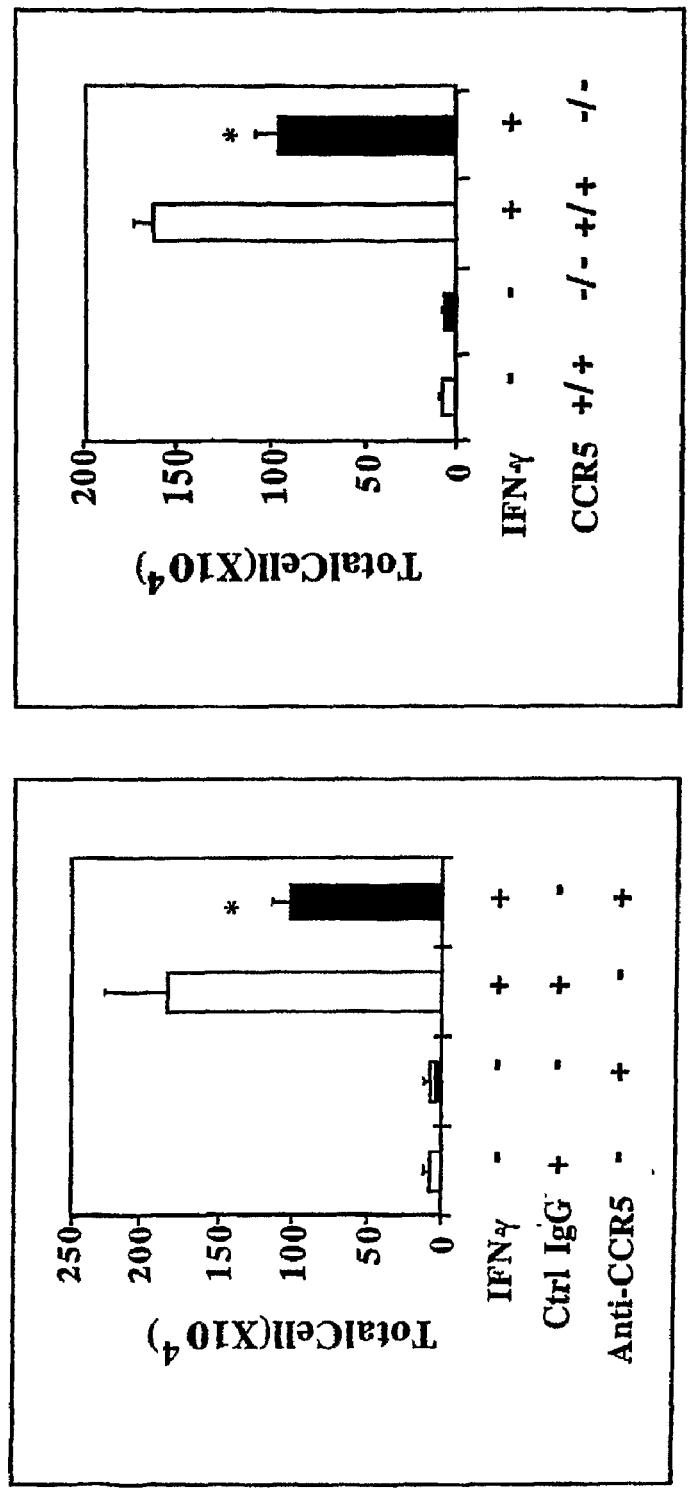
FIG. 3A shows bronchioalveolar lavage (BAL) total cell count of IFN-γ mice treated with and without anti-CCR5 antibody.
FIG. 3B shows BAL total cell count of IFN-γ mice with null mutation of CCR5.

As previously reported, IFN-γ increased BAL cell recovery by approximately 3-fold, increased BAL macrophage and neutrophil recovery and induced a patchy macrophage- and neutrophil-rich inflammatory response (FIG. 3). Treatment with anti-CCR5 did not alter the number or differential of the cells that were recovered in BAL fluids and did not alter the tissue histology of lungs from transgene (−) mice (FIG. 3). In contrast, neutralization of CCR5 significantly decreased the total number of cells that were recovered in BAL fluids from dox-treated Tg (+) mice (FIG. 3A). This anti-CCR5-induced decrease in inflammation was the result of decreases in macrophage and granulocyte recovery and was associated with a decrease in tissue inflammation. Importantly, similar alterations were seen when BAL and tissues from Tg (+) mice with wild type (+/+) or null mutant (−/−) CCR5 loci were compared (FIG. 3B). These studies demonstrate that CCR5 plays a crucial role in the intensity and nature of IFN-γ-induced pulmonary inflammation.

Example 3

Role of CCR5 in IFN-γ-Induced Alveolar Remodeling and Destruction

To define the role of CCR5 in the pathogenesis of IFN-γ-induced alveolar remodeling, alterations in lung size, lung volume, alveolar size and lung compliance in dox-treated Tg (+) mice treated with control antiserum or anti-CCR5 were compared. Lung volume, alveolar size and lung compliance were assessed via volume displacement and morphometric chord length assessments as previously described. In brief, the trachea was cannulated, the lungs were degassed and the lungs and heart were removed en bloc and inflated with PBS at 25 cm of pressure. The size of the lung was evaluated via volume displacement. Compliance was calculated as the change in volume divided by the change in pressure. Alveolar size was estimated from the mean chord length of the airspace.

Dox induction of IFN-γ caused an impressive increase in all of these parameters. Treatment with anti-CCR5 did not alter these parameters in lungs from wild type mice (FIG. 4). In contrast, these effects of IFN-γ were markedly diminished in dox-treated Tg (+) mice treated with anti-CCR5. Lungs from CC10-rtTA-IFN-γ Tg (+) mice treated with anti-CCR5 were significantly smaller and less compliant than lungs from Tg (−) mice treated with control serum (FIG. 4A). Alveolar size was similarly decreased when assessed with light microscopic or morphometric approaches (FIGS. 4C and 4D). Importantly, similar decreases in alveolar remodeling were noted in comparisons of lungs from dox-treated Tg (+) mice with (+/+) and (−/−) CCR5 loci. When viewed in combination, these studies demonstrate that CCR5 plays a critical role in the pathogenesis of IFN-γ-induced alveolar remodeling and destruction in the murine lung.

Example 4

Effect of CCR5 Regulation on IFN-γ Elaboration

A deficiency of CCR5 could modify IFN-γ-induced tissue responses by altering the production of transgenic IFN-γ or modulating its effector response. To determine if alterations in CCR5 regulated the production of IFN-γ, the levels of BAL IFN-γ in Tg (+) and Tg (−) mice with control serum or anti-CCR5 were compared.

To quantify IFN-γ levels, Mice were killed by cervical dislocation and a median sternotomy was performed. The trachea was isolated by blunt dissection and small caliber tubing was inserted and secured in his airway. Three successive volumes of 0.6 ml of PBS were instilled and gently aspirated and pooled. Each BAL sample was centrifuged and the supernatants were stored at −70° C. Cell numbers were assessed with hemocytometer and cellular differential counts were undertaken on cytospin preparations. IFN-γ levels were determined by ELISA using a commercial kit according to the manufacturer's instructions (R&D Systems, Minneapolis, Minn.).

Figures 5A, 5B:
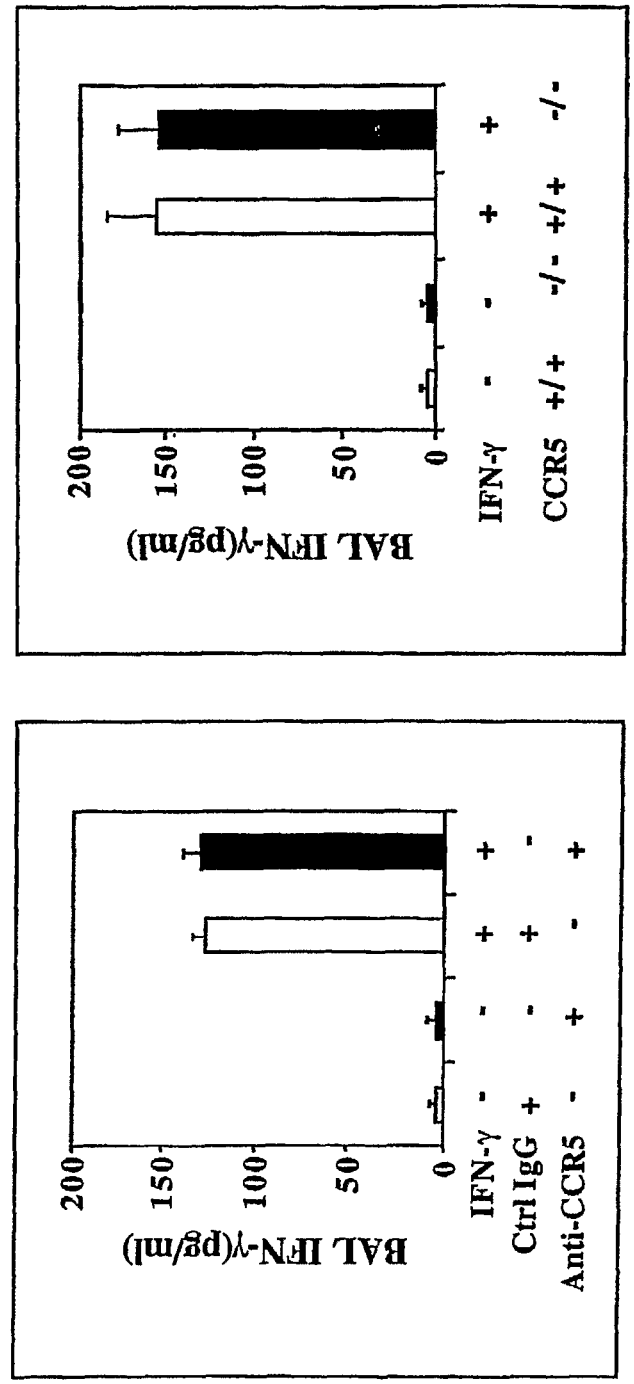
FIGS. 5A-5B, shows the effect of CCR5 regulation on IFN-γ elaboration.

The study shows that IFN-γ was not readily apparent in BAL fluids from Tg (−) mice, regardless of the type of serum that they were exposed to (FIG. 5). In contrast, similar levels of BAL IFN-γ were noted in dox-treated Tg (+) animals. Neutralization to CCR5 with anti-CCR5 did not alter the levels of BAL IFN-γ (FIG. 5A). A null mutation of CCR5 also did not alter the levels of transgenic IFN-γ that were produced since similar levels of BAL IFN-γ were noted in BAL fluid from Tg (+) mice with (+/+) and (−/−) CCR5 loci (FIG. 5B). These studies demonstrate that CCR5 neutralization or null mutation alters the phenotype induced by IFN-γ by modifying IFN-γ-induced effector pathway activation.

Example 5

Role of CCR5 in IFN-γ-Induced Chemokine Elaboration

Figure 6F:
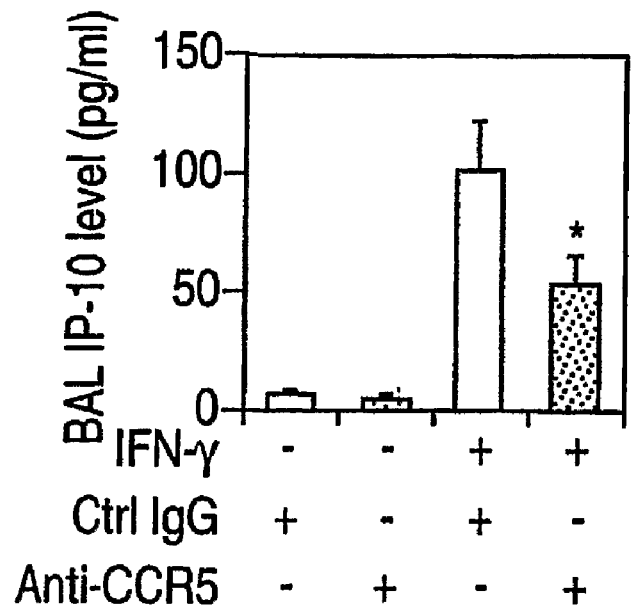
Figure 6G:
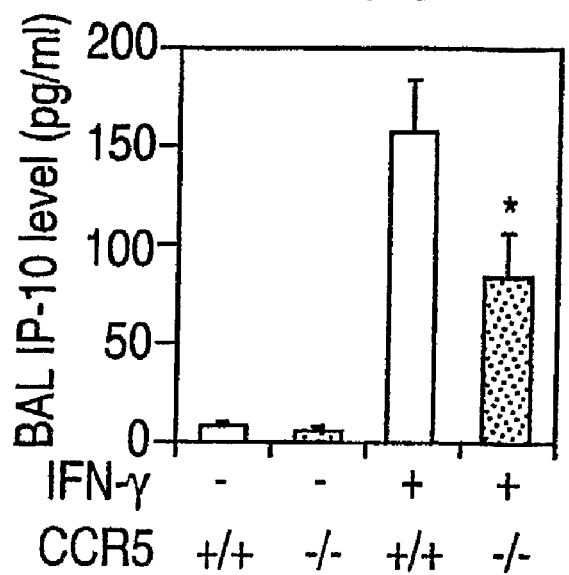

To investigate the mechanism by which CCR5 deficiency inhibited IFN-γ-induced inflammation, we compared the expression of selected chemokines, Tg (+) mice treated with control serum or anti-CCR5. In Tg (−) mice treated with control serum or anti-CCR5, the levels of mRNA encoding monocyte chemotactic protein (MCP)-1/CCL-2, MCP-2/CCL-8, MCP-3/CCL-7, MCP-5/CCL-12, MIP-1α/CCL-3, MIP-2/CXCL-2/3, MIP-1β/CCL-4, RANTES/CCL-5, KC/CXCL-1, Mig/CXCL-9, IP-10/CXCL-10, lungkine/CXCL-15 and SDF-1/CXCL-12 were comparable and, in most cases, were near or below the limits of detection of our assays. In contrast, IFN-γ caused marked increases in the levels of mRNA encoding these chemokine moieties in dox-treated Tg (+) mice. CCR5 neutralization markedly diminished the ability of IFN-γ to stimulate the accumulation of MCP-1/CCL-2, MCP-3/CCL-7, MCP-5/CCL-12, MIP-1α/CCL-3, MIP-2/CXCL-2/3, RANTES/CCL-5, KC/CXCL-1 and IP-10 (CXCL-10) mRNA. In all cases, comparable decreases in BAL chemokine protein levels were also noted. In contrast, CCR5 neutralization did not alter the ability of IFN-γ to stimulate the accumulation of mRNA encoding MCP-2/CCL-8, MIP-2/CCL-2/3, Mig/CXCL-9, SDF-1/CXCL, lungkine/CXCL-15 or I-TAC/CXCL-11 (FIG. 6A). Importantly, similar alterations in the levels of mRNA and the levels of protein for these chemokines were noted in comparisons of dox-treated Tg (+) mice with (+/+) and (−/−) CCR5 loci. When viewed in combination, these studies demonstrate that IFN-γ stimulates a wide variety of CC and CXC chemokines in the lung. They also demonstrate that these inductive responses are mediated via CCR5-dependent and -independent pathways with MCP-1/CCL-2, MCP-3/CCL-7, MCP-5/CCL-12, MIP-1α/CCL-3, MIP-1β/CCL-4, MIP-2/CXCL-2/3, RANTES/CCL-3, KC/CXCL-1 and IP-10/CXCL being induced by the former and MCP-2/CCL-8, MIP-2/CXCL-2/3, Mig/CXCL-9, SDF-1/CXCL-12, lungkine/CXCL-15 and I-TAC/CXCL-11 being induced by the latter.

Example 6

Role of CCR5 in IFN-γ-Induced Protease and Antiprotease Alterations

Figures 7A, 7B:
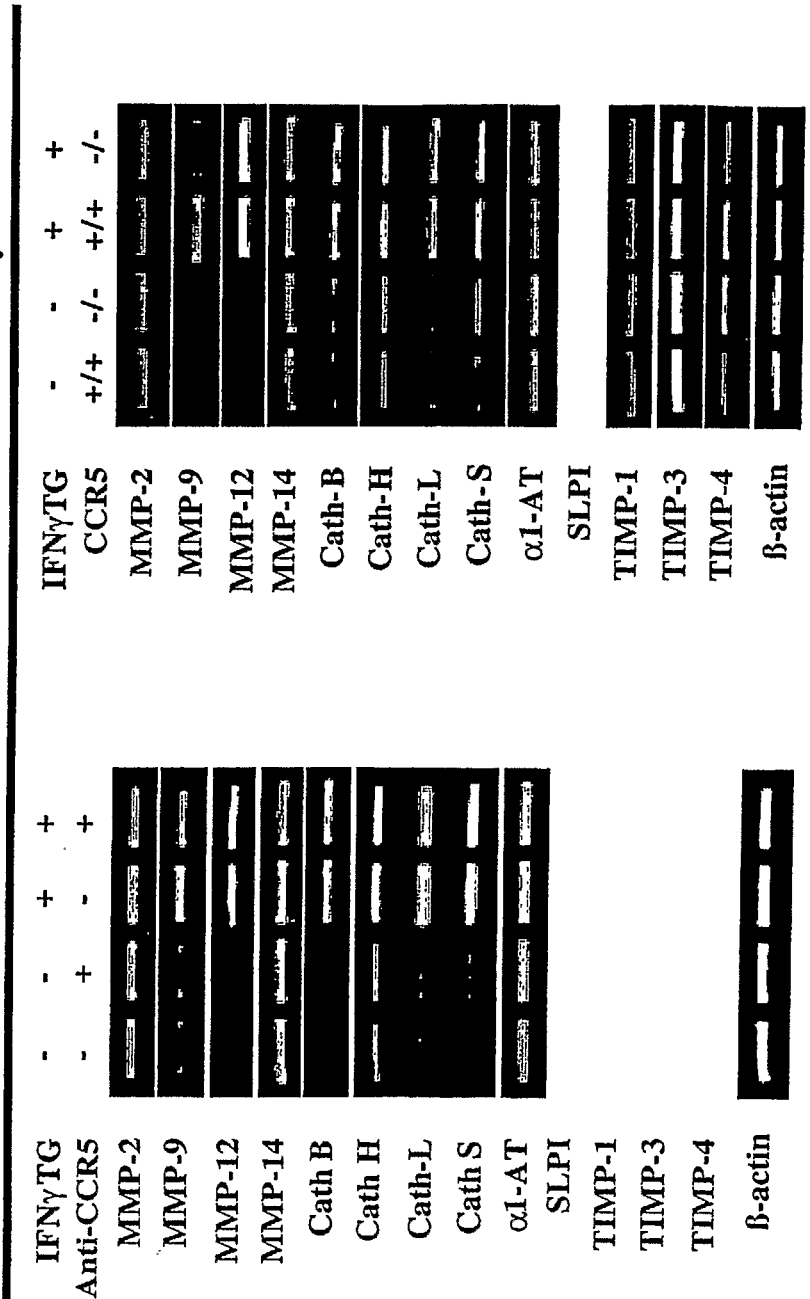
FIGS. 7A-7B, shows the role of CCR5 in IFN-γ induced protease and antiprotease alterations.

This example shows that a deficiency of CCR5 can modulate the IFN-γ-induced inflammatory and alveolar phenotypes by decreasing the production of respiratory proteases and or antiproteases. In the experiment, levels of mRNA encoding lung-relevant MMPs and cathepsins in Tg (−) and Tg (+) mice treated with control serum or anti-CCR5 were compared. Comparable levels of mRNA encoding MMP-2, MMP-9, MMP-12, MMP-14, cathepsin B, cathepsin H, cathepsin L, cathepsin S, α1-AT and TIMPs 1-4 were noted in lungs from Tg (−) mice treated with pre-immune serum or anti-CCR5 (FIG. 7A). In these mice, the levels of mRNA encoding many of these moieties were near or below the limits of detection of our assays. In accord with previous studies from the present inventors, dox induction of IFN-γ increased the levels of expression of MMPs-9, -12 and -14 and cathepsins B, H, L and S while inhibiting the expression of SLPI and not altering the expression of IFN-γ or the TIMPs (FIG. 7). Interestingly, CCR5 neutralization decreased the ability of IFN-γ to stimulate the accumulation of mRNA encoding MMP-9 and inhibit the expression of SLPI (FIG. 7B). It did not, however, alter the levels of expression of the other MMPs, cathepsins and TIMPs. When viewed in combination, these studies demonstrate that IFN-γ selectively stimulates MMP-9 and inhibits SLPI via a CCR5-dependent activation pathway.

Example 7

Role of CCR5 in IFN-γ-Induced DNA Injury and Cell Death

In keeping with the proposed role of apoptosis in the pathogenesis of the alveolar remodeling in emphysema, studies were also undertaken to determine if IFN-γ induced DNA injury and apoptosis and if CCR5 played an important role in their genesis. In these experiments, Tg (−) and Tg (+) mice received either anti-CCR5 or control Ig and DNA injury and cell death were evaluated with TUNEL evaluations and dual propidium iodide and annexin-5 staining.

Type II cells were isolated from WT and IFN-γ transgenic mice using the methods developed by Corti et al. After anesthesia, the trachea was cannulated with 20-gauge tubing, the lungs were filled with 2 ml Dispase (Roche Diagnostic) followed by 0.5 ml of 1% low-melting-point agarose and the agarose was allowed to harden under crushed ice. The lungs were then placed in 2 ml of Dispase (1 hour, room temperature) and transferred to Dulbecco's modified Eagle's medium (DMEM) with 25 mM HEPES with 0.01% DNAse I (Sigma, St Louis, Mo.). After teasing apart the digested tissue, the resulting cell suspension was sequentially filtered through nylon mesh filters and collected after centrifugation (8 minutes, 130×g). Contaminating cells were removed by incubating the cell suspension in 100-mm tissue culture plates coated with a mixture of anti-CD16/CD32 and anti-CD45 monoclonal antibodies (PharMingen, San Diego, Calif.) overnight at 4° and washing the non-adherent cell population. The resulting cells were >97% type II cells and were resuspended in 1× binding buffer at $1 \times 10^6$ cells/ml for subsequent FACS analysis. Annexin V and propidium iodine (PI) staining were undertaken with the annexin V-FITC apoptosis detection kit (BD Biosciences, Franklin Lakes, N.J.) as described by the manufacturer. Analysis was undertaken by flow cytometry (Becton Dickinson).

The TUNEL evaluations involves the end labeling of exposed 3'-OH ends of DNA fragments in paraffin embedded tissue using the TUNEL in situ cell death detection kit AP (Roche Diagnostics, Indianapolis, Ind.) following the instructions provided by the manufacturer. Staining specificity was assessed by comparing the signal that was seen when terminal transferase was included and excluded from the reaction. After staining, 20 fields of alveoli were randomly chosen and 2000 nuclei were counted per lung. The labeled cells were expressed as a percentage of total nuclei.

Figure 8E:
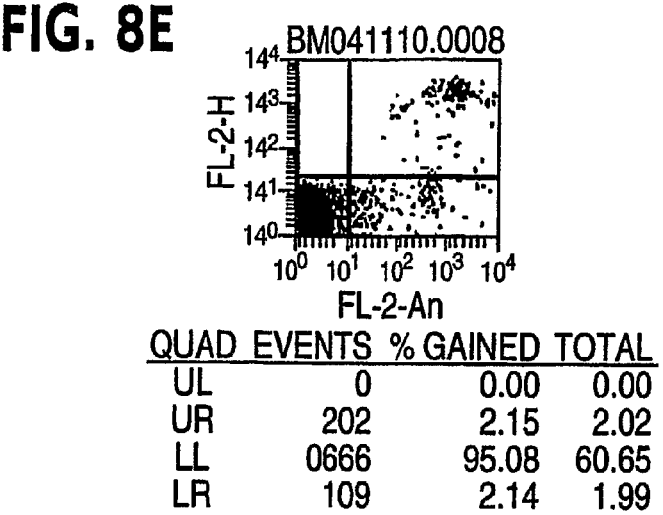
Figure 8F:
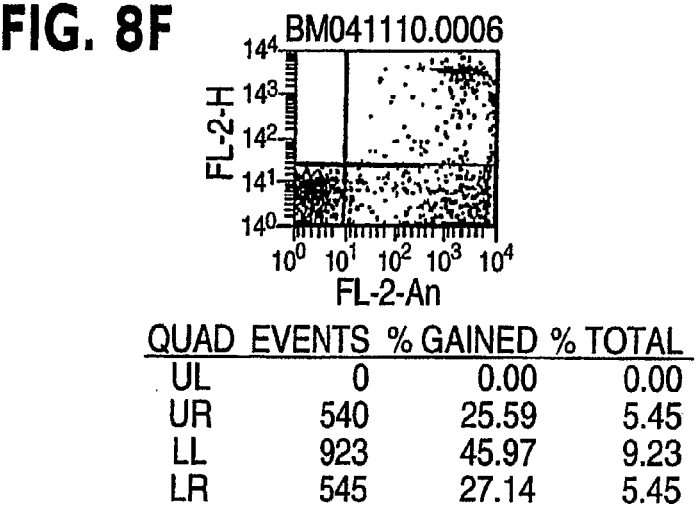
Figure 8G:
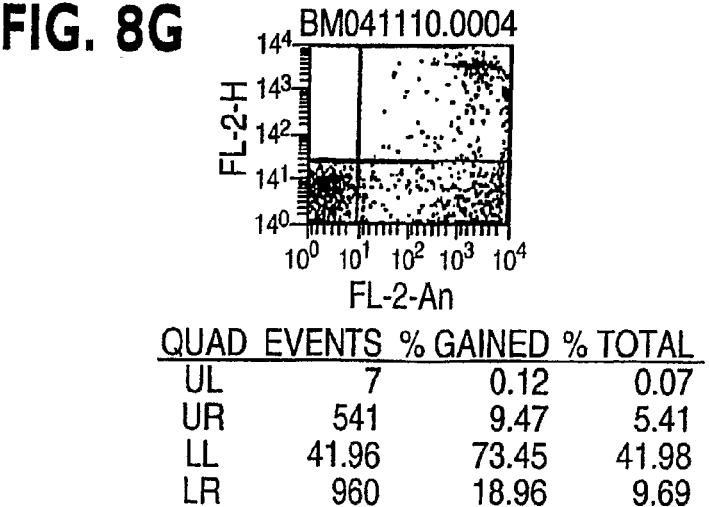

In Tg (−) mice, <2% of cells were TUNEL (+) and treated with anti-CCR5 did not alter this level of DNA injury (FIG. 8). In contrast, dox induction of IFN-γ caused an impressive increase in TUNEL staining in lungs from Tg (+) mice (FIG. 8). This response was seen predominantly in alveolar epithelial cells with occasional endothelial cells and macrophages showing a nuclear staining. Double annexin-5 and propidium iodine staining with FACS analysis demonstrated that many (but not all) of the TUNEL (+) cells were undergoing apoptosis with only a small number undergoing pure necrosis or both responses (FIGS. 8C and 8D). Importantly, treatment with anti-CCR5 caused an impressive decrease in TUNEL staining and an impressive decrease in the percent of cells undergoing apoptosis. Similar results were seen with TUNEL and dual propidium iodide/annexin-5 staining of lungs from dox-treated Tg (+) mice with (+/+) and (−/−) CCR5 loci (FIGS. 8E, 8F, and 8G). This response was maximal after 2 days of dox administration at which time approximately 15% of lung cells were TUNEL (+). When viewed in combination, these studies demonstrate that IFN-γ is a potent inducer of DNA injury and apoptosis and that this response is mediated, in part, via a CCR5-dependent mechanism.

Example 8

Mechanism of CCR5 Regulation of Apoptosis

Figure 9A:
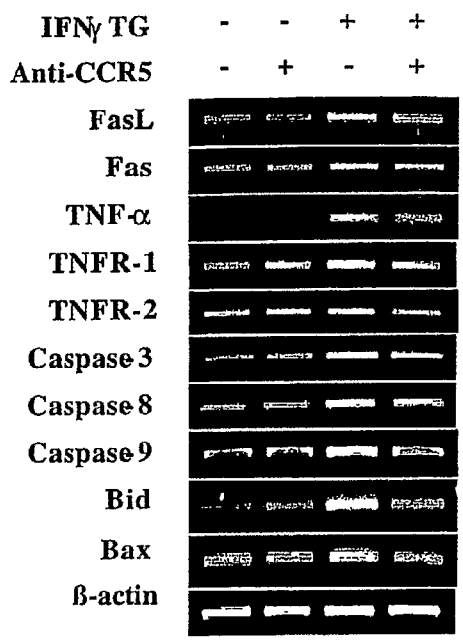
Figure 9D:
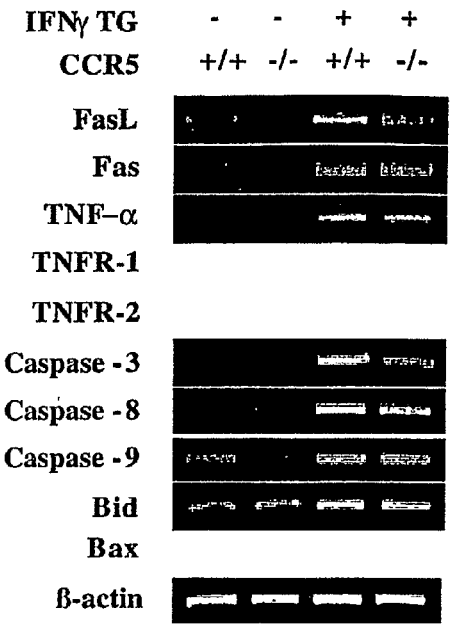
Figure 9B:
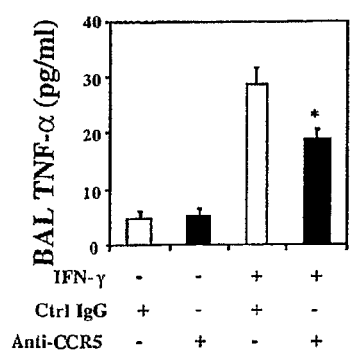
Figure 9E:
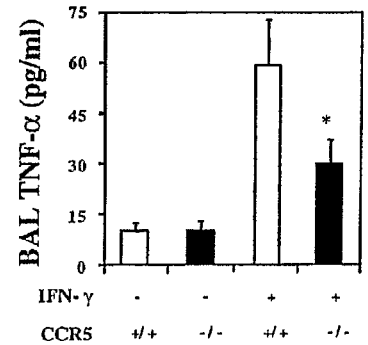
Figure 9F:
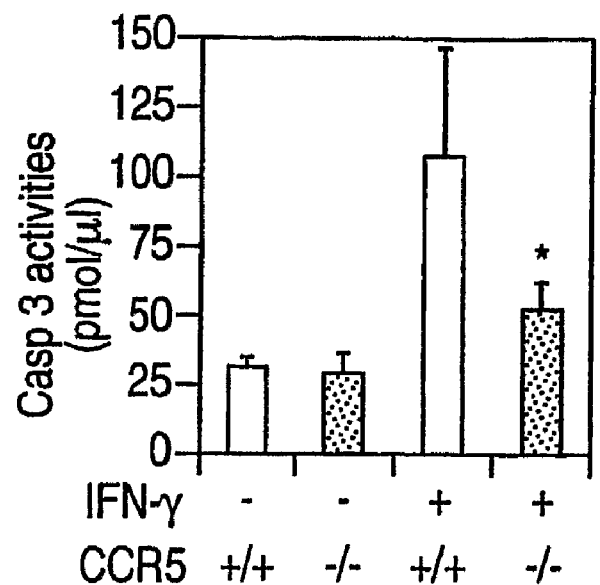
Figure 9G:
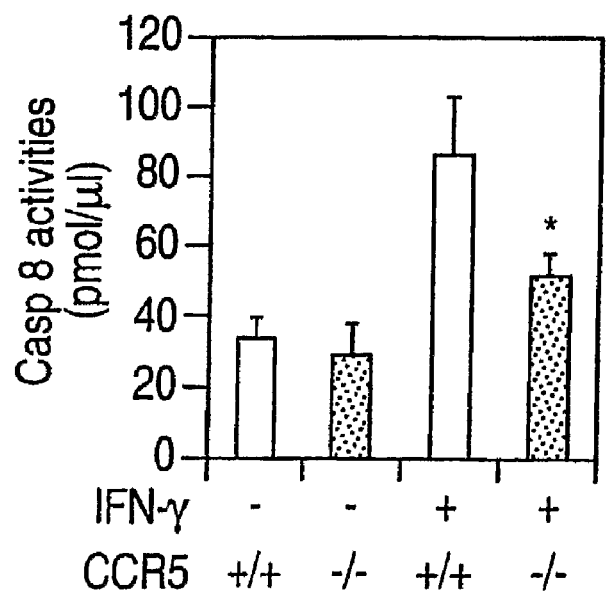
Figure 11:
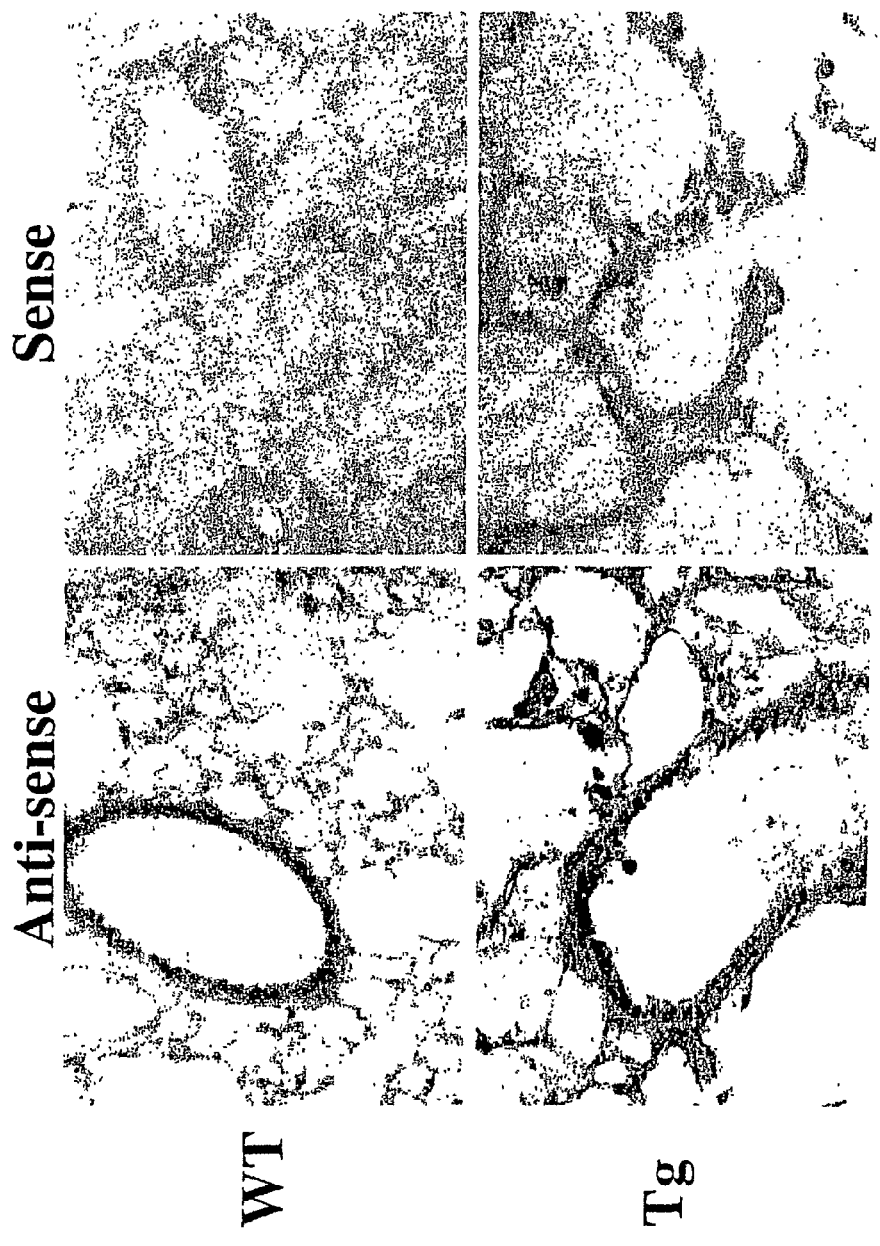
FIG. 11 depicts in situ hybridization of lung tissue from CC10-IFN-γ mice treated with sense and antisense CCR5.
Figure 12:
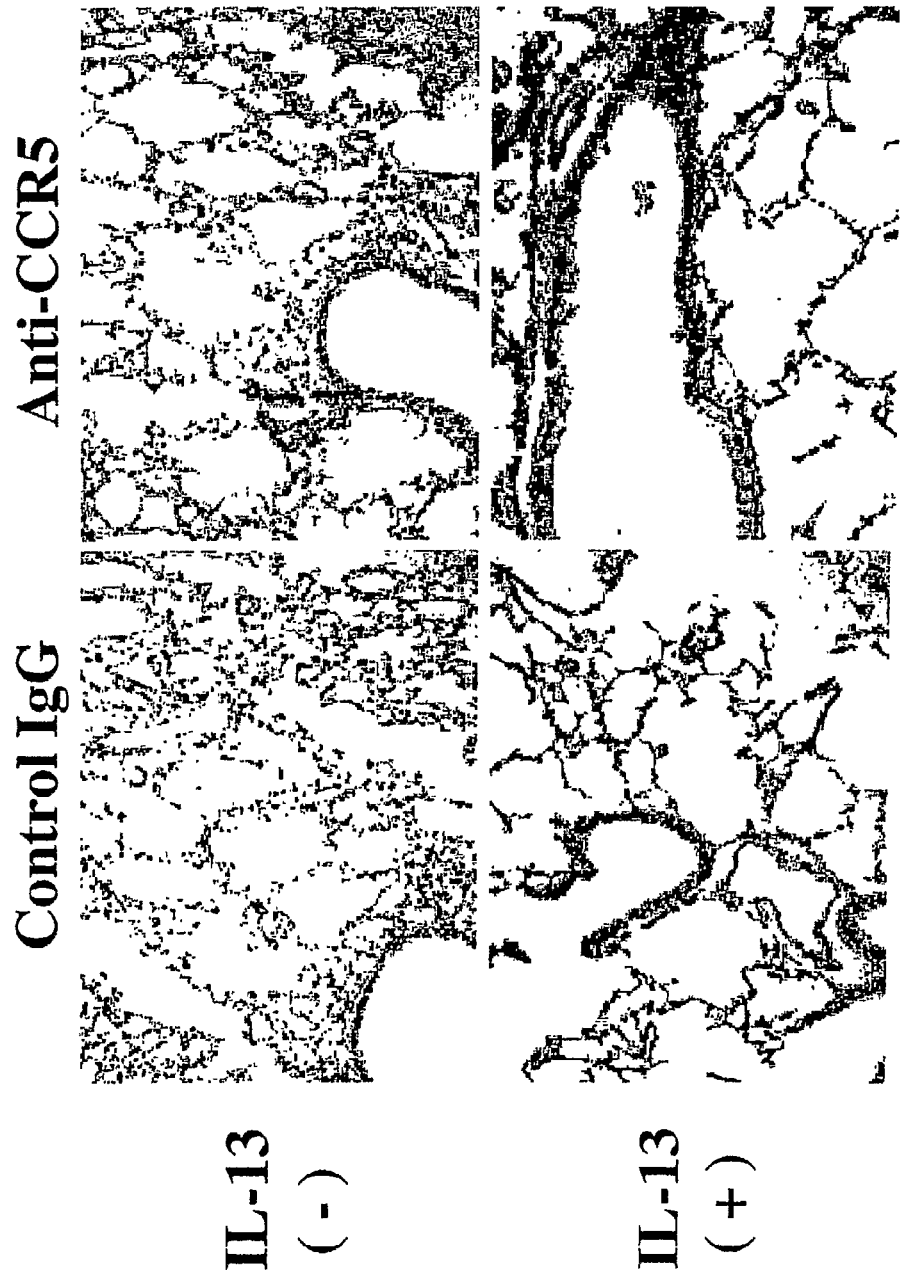
FIG. 12 depicts immunohistochemistry of lung tissue from CC10-IFN-γ mice treated with control IgG and anti-CCR5 antibody.
Figure 14B:
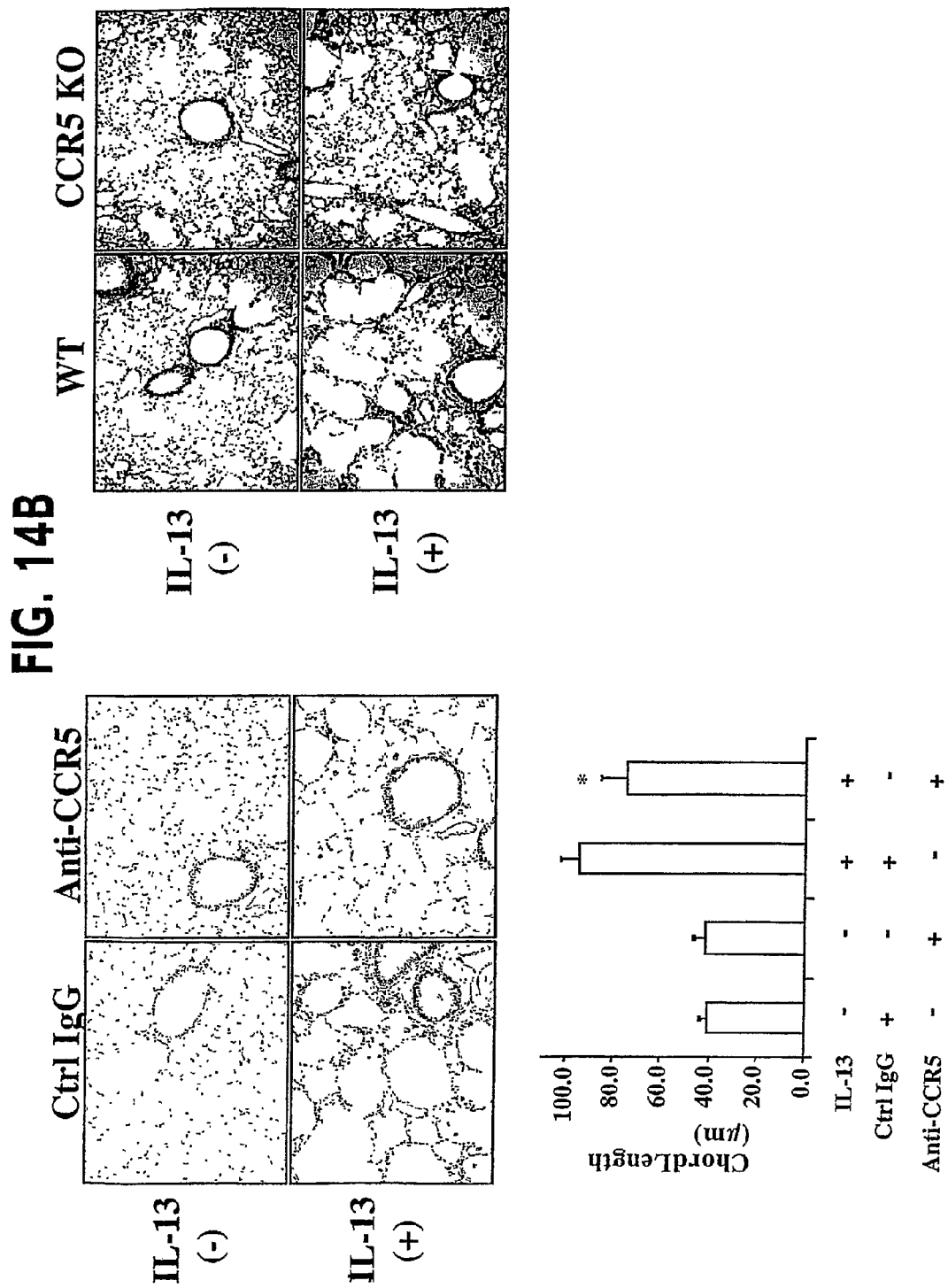
FIG. 14, comprising FIGS. 14A-14B demonstrates the role of CCR5 in IL-13 induced inflammation in IL-13 mice or IL-13 mice with null mutation of CCR5.
Figure 15:
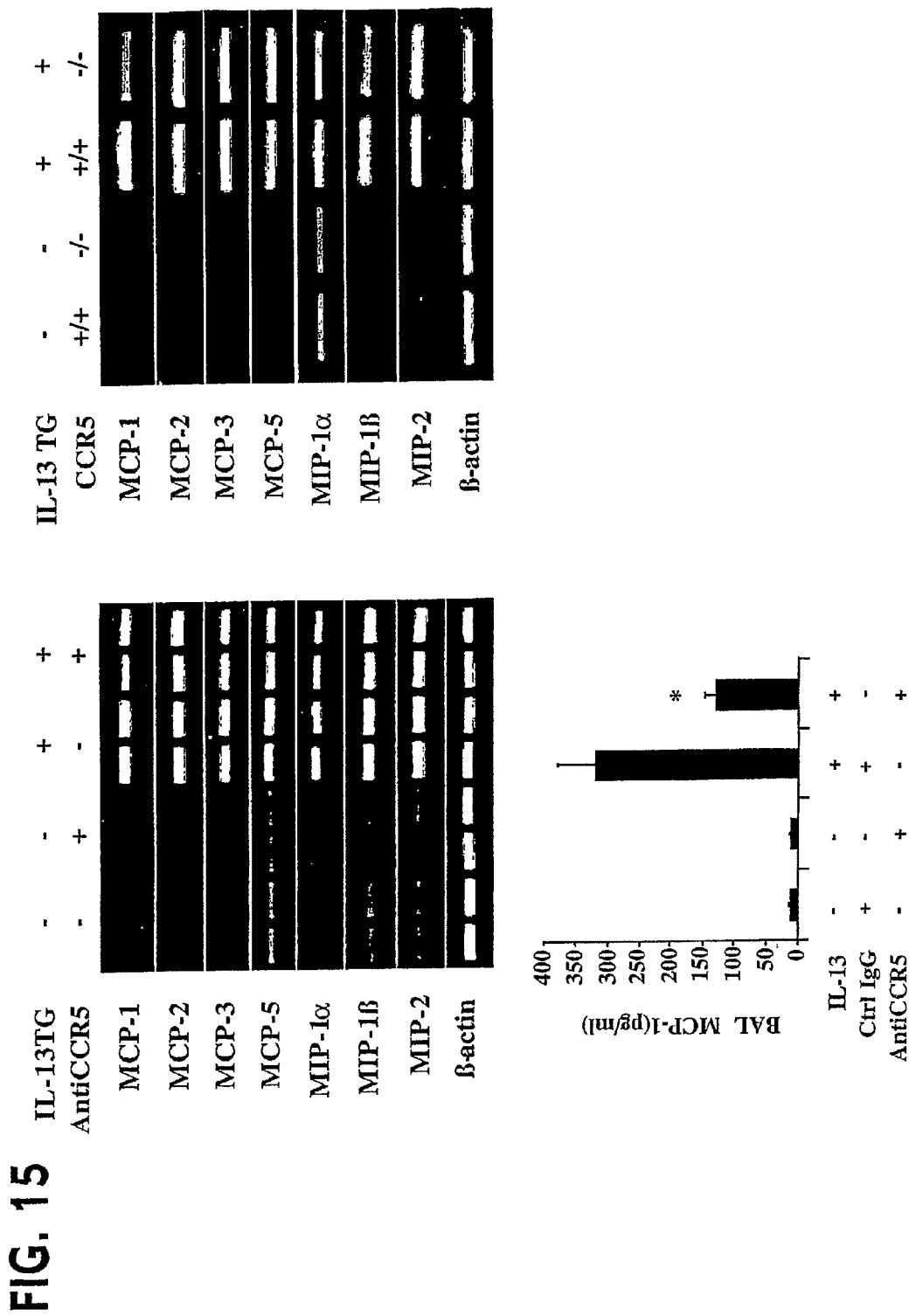
FIG. 15 shows the effect of CCR5 in IL-13 induced chemokine elaboration
Figure 16:
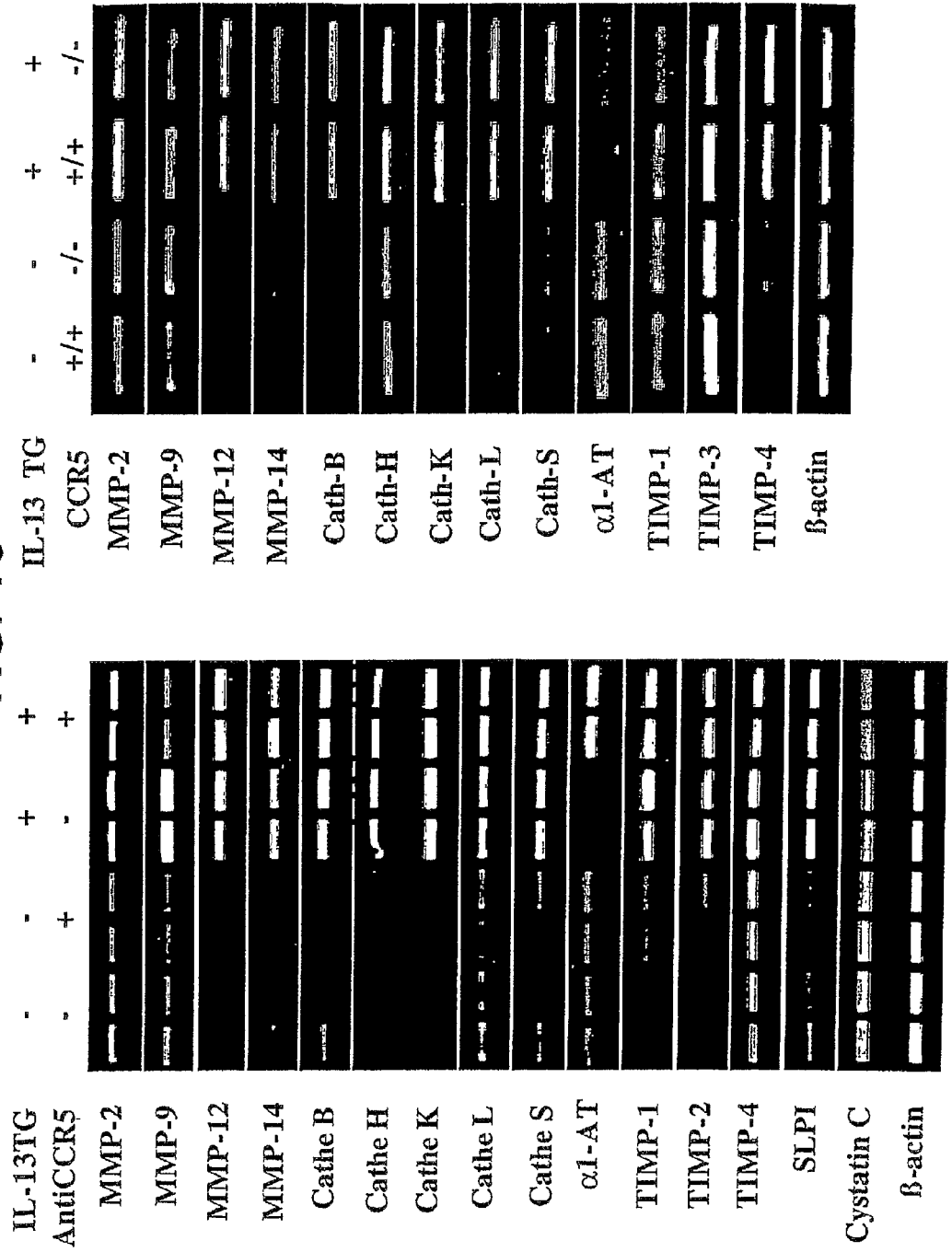
FIG. 16 shows the role of CCR5 in IL-13 induced protease and antiprotease alterations.
Figure 17:
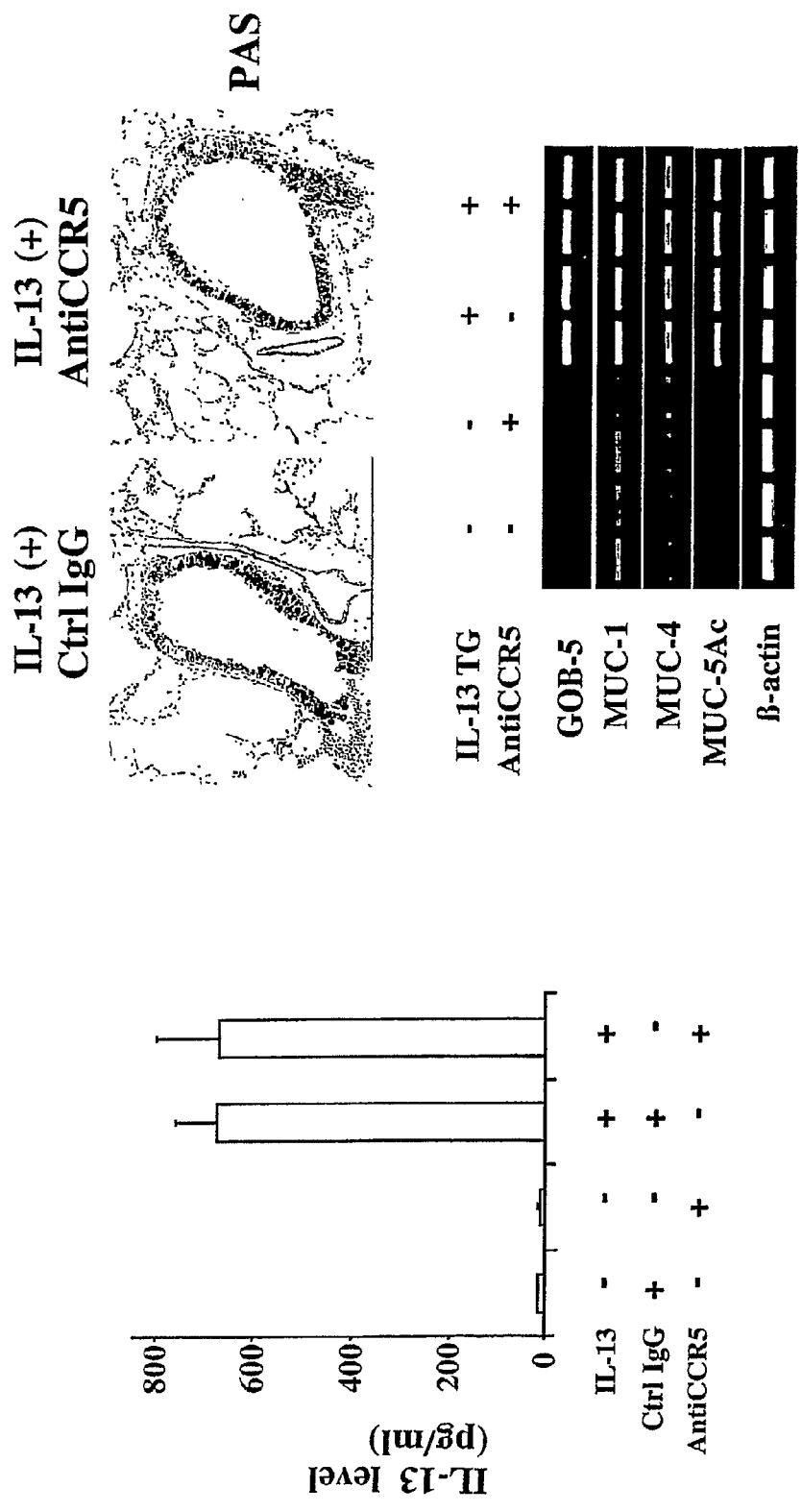
FIG. 17 shows the BAL IL-13 level of IL-13 mice treated with anti-CCR5 antibody.
Figure 18:
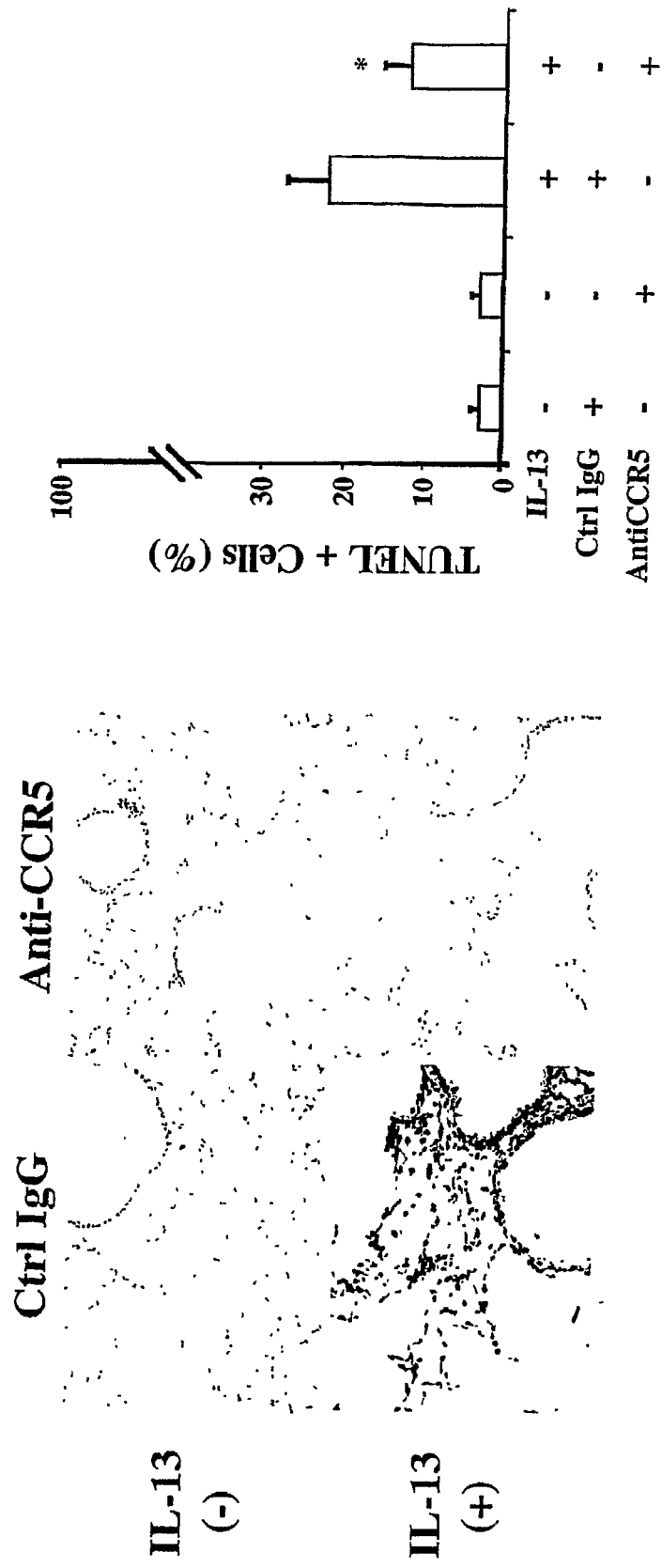
FIG. 18 is an image depicting TUNEL staining of the lung tissue of an IL-13 mouse.
Figure 19:
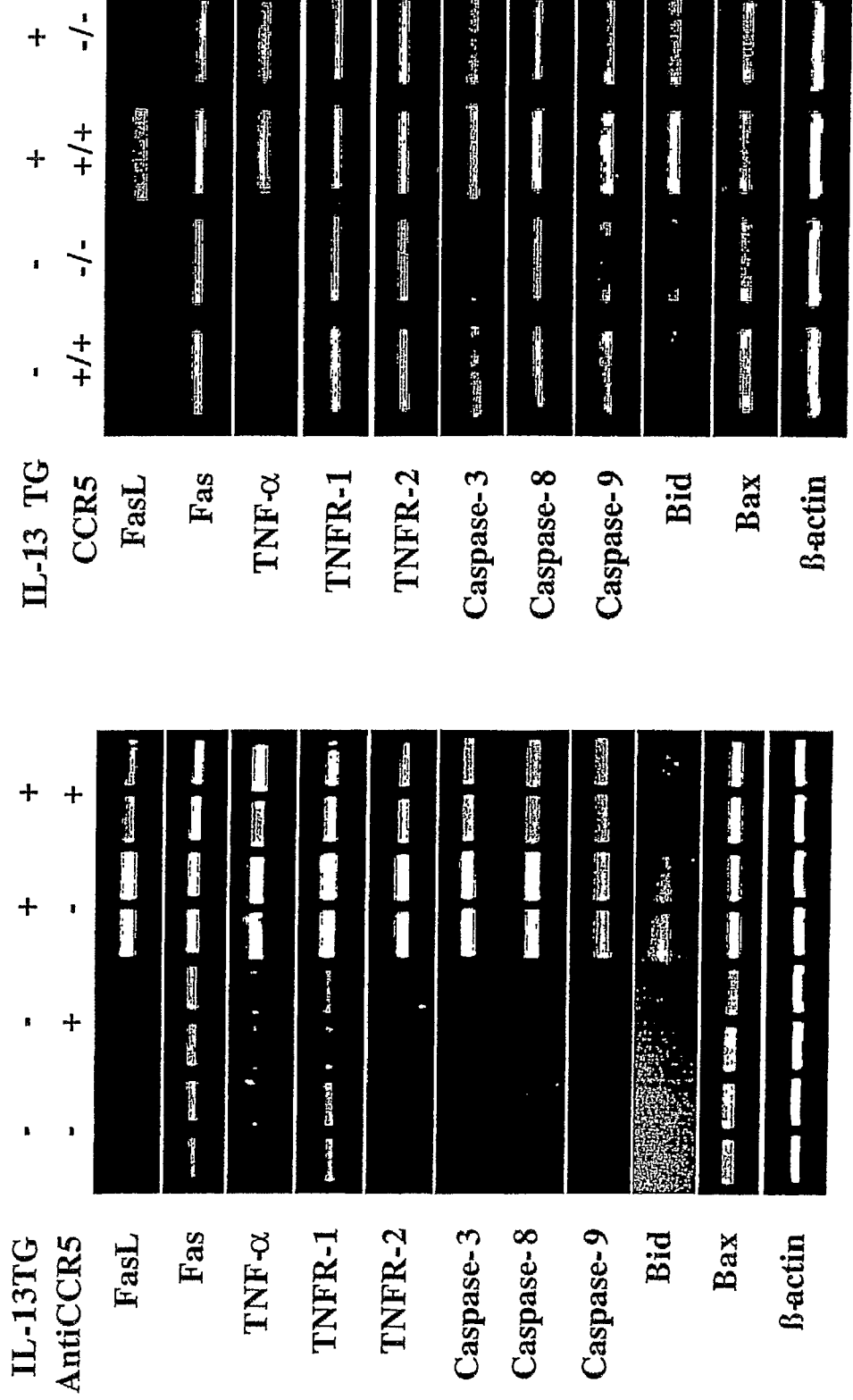
FIG. 19, shows the mechanism of CCR5 regulation of apoptosis in IL-13 induced inflammation.
Figure 20:
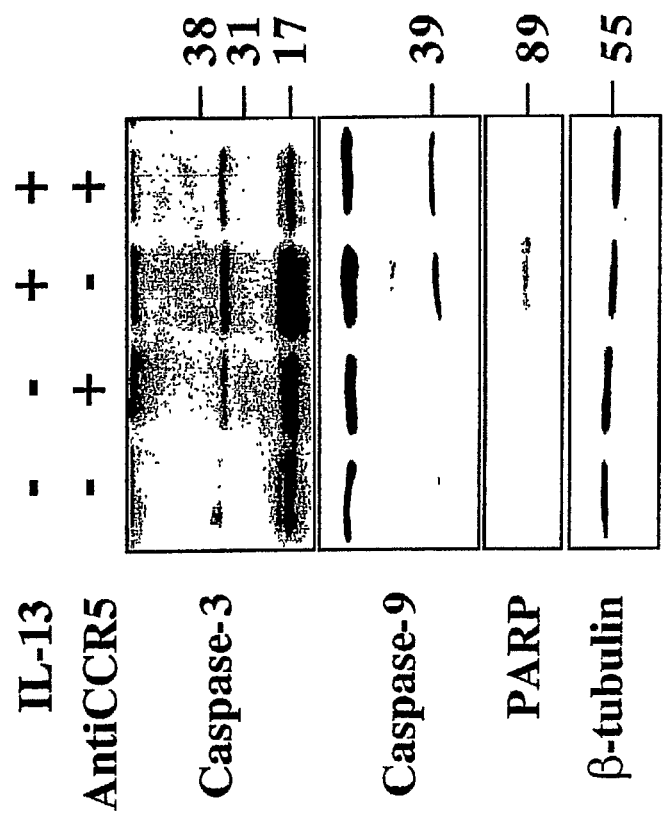
FIG. 20 depicts a Western blot detecting apoptotic factors in the lung of IL-13 transgenic mice.
Figure 21:
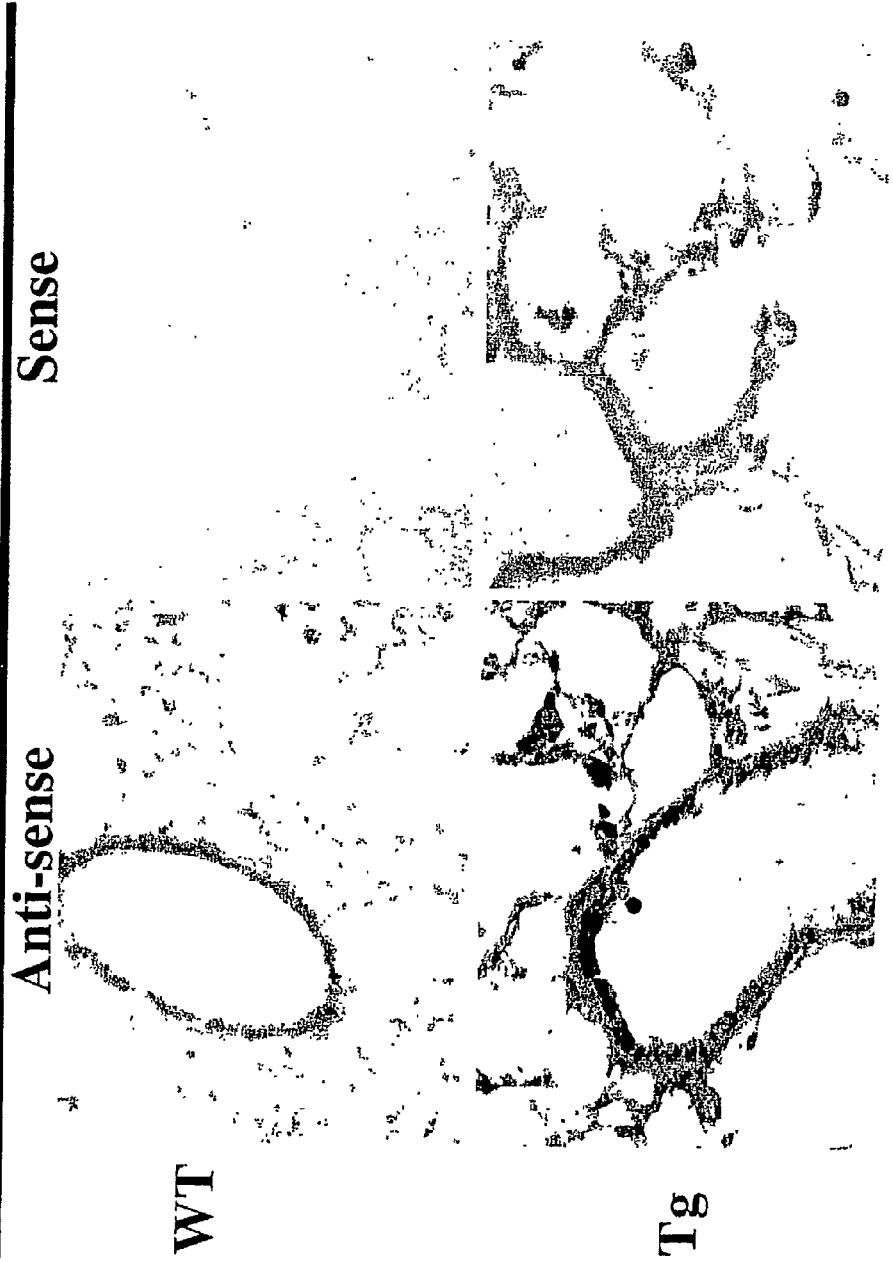
FIG. 21 depicts in situ hybridization of lung tissue from CC10-IL-13 mice treated with sense and antisense CCR5.
Figure 23:
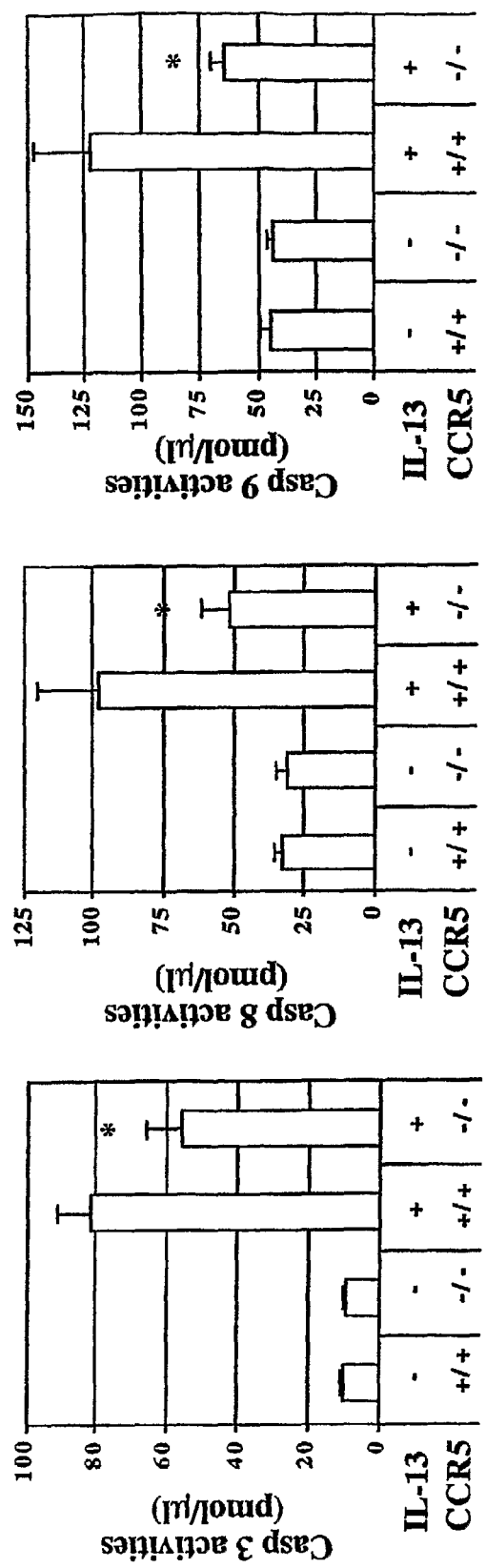
FIG. 23 shows caspase activities in the CCR5Ko/IL-13 mice.
Figure 24:
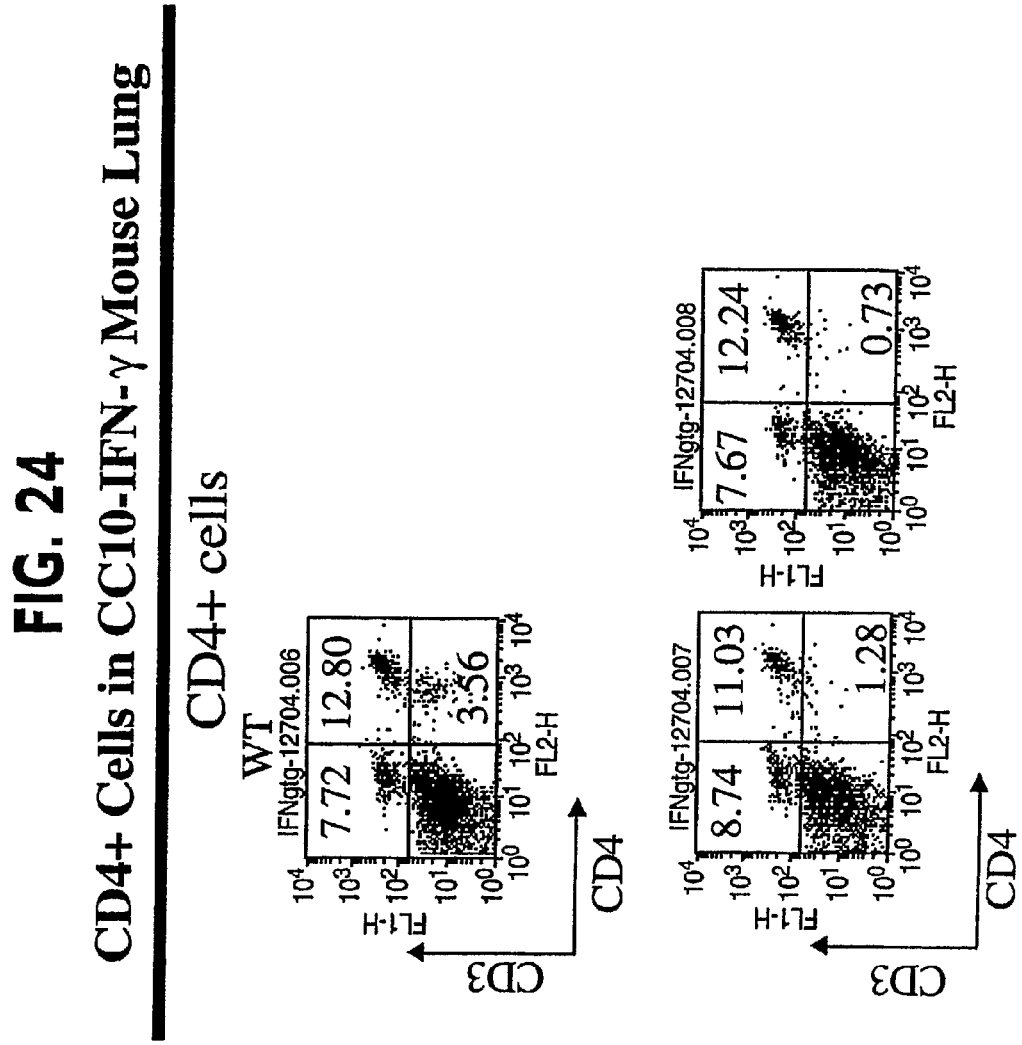
FIG. 24 shows CD+4 cells in the lungs of CC10-IFN-γ mice.
Figure 25:
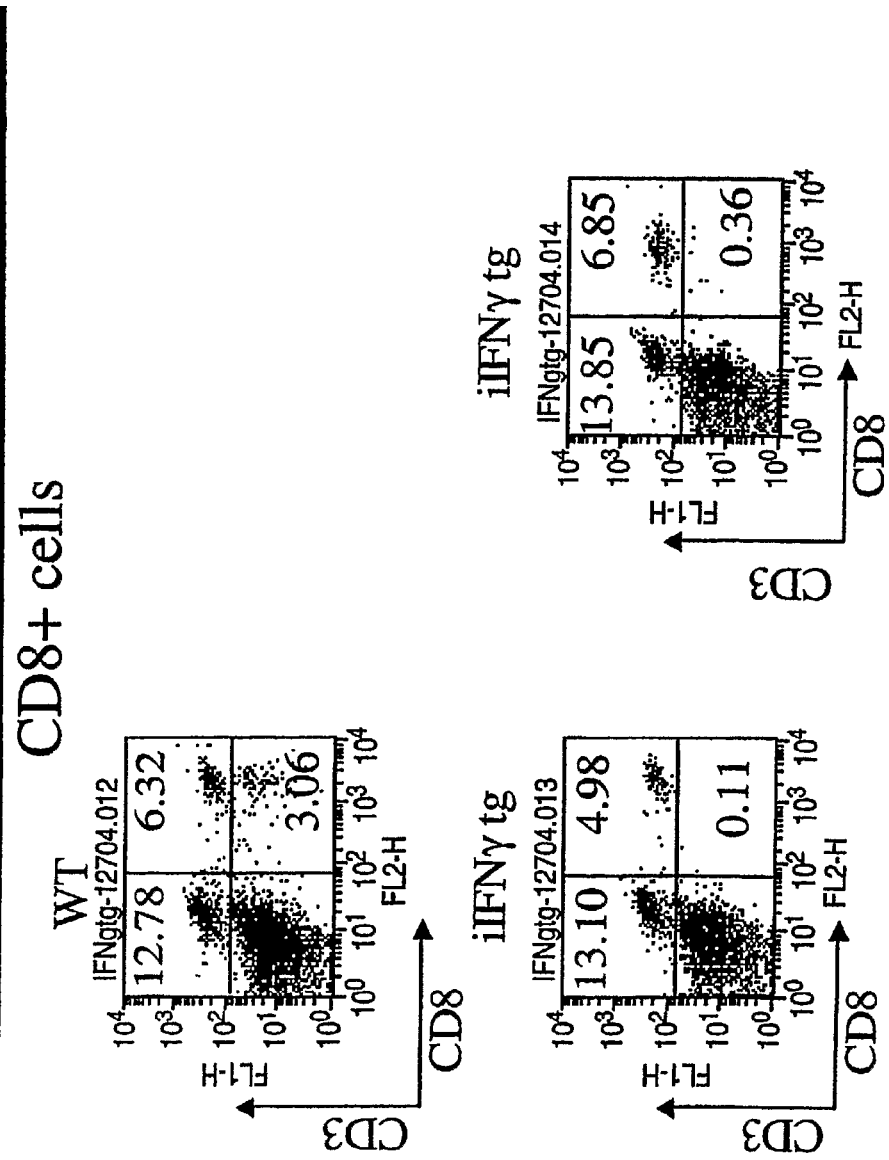
FIG. 25 shows CD84 cells in the lungs of CC10-IFN-γ mice.
Figure 26:
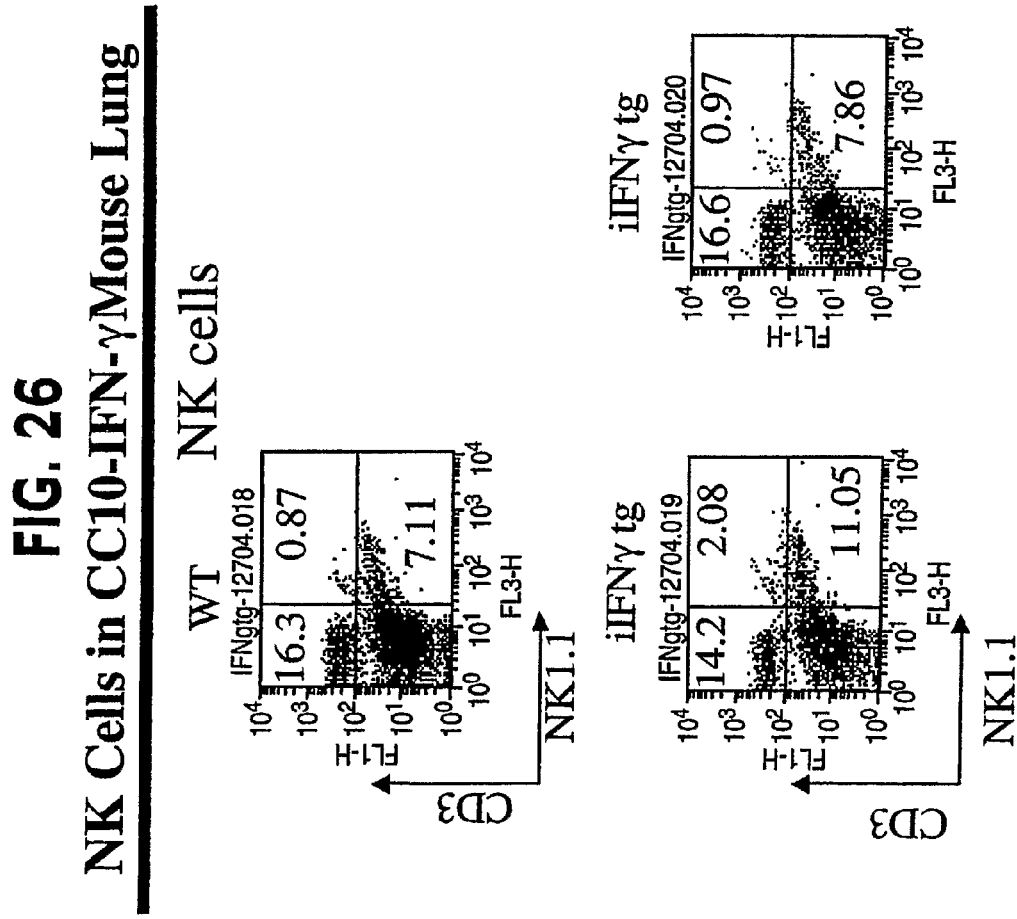
FIG. 26 shows NK cells in the lungs of CC10-IFN-γ mice.

To further understand the mechanism by which CCR5 regulated apoptosis, the expression and activity of caspases and key apoptosis regulators were evaluated in mice that were sufficient and deficient in CCR5. The levels of mRNA encoding Fas, Fas-L, TNF, caspases-3, -8, -9, Bid and Bax in Tg (−) mice were at or near the limits of detection in our assays and were not significantly altered by treatment with anti-CCR5 (FIG. 9A). IFN-γ was a potent stimulator of these moieties that increased the levels of Fas, Fas-L, TNF, caspases-3, -8, -9, Bid and Bax mRNA and the levels of TNF in caspases-3, -8 and -9 and Bid and Bid protein. IFN-γ also activated caspases-3, -8 and -9 causing readily detectable increases in their bioactivities and activated Bid causing increases in tBid accumulation. In all cases, these events were CCR5-dependent with anti-CCR5 treatment decreasing the levels of mRNA encoding Fas, Fas-L, TNF, caspases-3, -8 and -9, Bid and Bax, the levels of TNF and caspase protein, the activation of caspases-3, -8 and -9, caspases-3, -8 and -9 bioactivity and tBid accumulation (FIG. 9). Similar results were seen with null mutations of CCR5 because the ability of IFN-γ to stimulate and/or activate Fas, Fas-L, TNF, -3, -8 and -9, Bid and Bax were all decreased in Tg (+) mice with null CCR5 loci. When viewed in combination, these studies demonstrate that IFN-γ is a potent activator of the cell death and mitochondrial apoptosis pathways and that these activation events are mediated, in part, via CCR5-dependent pathways.

Example 9

Role of CCR5 in Cigarette-Smoke-Induced Inflammation and Alveolar Remodeling

The studies noted above demonstrate that CCR5 plays a key role in the pathogenesis of IFN-γ-induced inflammation and emphysema. Since the majority of pulmonary emphysema in the Western world is caused by cigarette smoke exposure (Senior), studies were undertaken to define the role of CCR5 in similar cigarette smoke-induced lesions.

In these studies, Female C57Bl/6 wild type (WT) mice and IFN-γ (−/−) mice were purchased from Jackson laboratory (Bar Harbor, Me.) and cathepsin-S (−/−) mice were generated in our laboratories. Starting at 10 weeks of age, they were exposed twice a day, 5 days a week, to room air or the smoke from two non-filtered standard research cigarettes (2R4, University of Kentucky) using the smoking apparatus described by Hautamaki et al. After 6 months the mice were anaesthetized and sacrificed, and the trachea was cannulated. After ligation of the right main bronchus, the left lung was inflated with 0.5% low temperature-melting agarose in 10% PBS-buffered formalin at a constant pressure of 25 cm. This allowed for homogenous expansion of lung parenchyma as described by Halbower et al. The lungs were then fixed in 10% PBS-buffered formalin for 24 hours, sectioned and evaluated using histologic, immunohistologic and morphologic methods as described above.

In these studies, chronic cigarette smoke exposure caused a modest macrophage- and neutrophil-rich BAL and tissue inflammatory response and modest emphysema that can be appreciated by morphometric evaluation techniques and light microscopy. It also caused DNA injury/apoptosis that could be appreciated with TUNEL evaluations (FIG. 10C). In all cases, these responses were CCR5-dependent because tissue and BAL inflammation, emphysema and TUNEL staining were all decreased in cigarette smoke exposed mice with (−/−) versus (+/+) CCR5 loci. These studies demonstrate that CCR5 plays a critical role in cigarette-smoke-induced inflammation, alveolar remodeling and DNA injury and apoptosis.

The data presented herein is by no means limited to studies of CCR5 antagonism of IFN-γ induced inflammation in transgenic mice inducibly overexpressing IFN-γ. Similar experiments have been performed in transgenic mice that inducibly overexpress IL-13. It has been observed that CCR5 antagonists are equally effective in reducing and inhibiting IL-13 induced inflammation in these mice. See the Figures set forth in the present invention.

All publications and patent applications cited in this specification are herein incorporated by reference as if each individual publication or patent application were specifically and individually indicated to be incorporated by reference.

REFERENCES

Abreu, M. T. (2002). "The pathogenesis of inflammatory bowel disease: translational implications for clinicians." *Curr Gastroenterol Rep* 4(6): 481-9.

Ahr, B., V. Robert-Hebmann, et al. (2004). "Apoptosis of uninfected cells induced by HIV envelope glycoproteins." *Retrovirology* 1(1): 12.

Algeciras-Schimnich, A., S. R. Vlahakis, et al. (2002). "CCR5 mediates Fas- and caspase-8 dependent apoptosis of both uninfected and HIV infected primary human CD4 T cells." *Aids* 16(11): 1467-78.

Algood, H. M. and J. L. Flynn (2004). "CCR5-deficient mice control *Mycobacterium tuberculosis* infection despite increased pulmonary lymphocytic infiltration." *J Immunol* 173(5): 3287-96.

Aliberti, J., C. Reis e Sousa, et al. (2000). "CCR5 provides a signal for microbial induced production of IL-12 by CD8 alpha+dendritic cells." *Nat Immunol* 1(1): 83-7.

Bagaeva, L. V., L. P. Williams, et al. (2003). "IL-12 dependent/IFN gamma independent expression of CCR5 by myelin-reactive T cells correlates with encephalitogenicity." *J Neuroimmunol* 137(1-2): 109-16.

Belperio, J. A., M. D. Burdick, et al. (2000). "The role of the CC chemokine, RANTES, in acute lung allograft rejection." *J Immunol* 165(1): 461-72.

Ben Ahmed, M., H. Houman, et al. (2003). "Cytokine expression within mucocutaneous lesions of Behcet's disease: involvement of proinflammatory and Th1 cytokines." *Adv Exp Med Biol* 528: 343-6.

Ben Ahmed, M., H. Houman, et al. (2004). "Involvement of chemokines and Th1 cytokines in the pathogenesis of mucocutaneous lesions of Behcet's disease." *Arthritis Rheum* 50(7): 2291-5.

Borra, R. C., P. M. Andrade, et al. (2004). "The Th1/Th2 immune-type response of the recurrent aphthous ulceration analyzed by cDNA microarray." *J Oral Pathol Med* 33(3): 140-6.

Bouma, G. and W. Strober (2003). "The immunological and genetic basis of inflammatory bowel disease." *Nat Rev Immunol* 3(7): 521-33.

Buono, C., C. E. Come, et al. (2003). "Influence of interferon-gamma on the extent and phenotype of diet-induced atherosclerosis in the LDLR-deficient mouse." *Arterioscler Thromb Vasc Biol* 23(3): 454-60.

Campbell, J. D., V. Gangur, et al. (2004). "Allergic humans are hyporesponsive to a CXCR3 ligand-mediated Th1 immunity-promoting loop." *Faseb J* 18(2): 329-31.

Cartier, L., M. Dubois-Dauphin, et al. (2003). "Chemokine-induced cell death in CCR5-expressing neuroblastoma cells." *J Neuroimmunol* 145(1-2): 27-39.

Castedo, M., J. L. Perfettini, et al. (2003). "Mitochondrial apoptosis induced by the HIV-1 envelope." *Ann N Y Acad Sci* 1010: 19-28.

Chae, S. C., Y. R. Park, et al. (2004). "The polymorphisms of Th1 cell surface gene Tim-3 are associated in a Korean population with rheumatoid arthritis." *Immunol Lett* 95(1): 91-5.

Chakravorty, S. J., A. J. Howie, et al. (2001). "Potential role for monocyte chemotactic protein-4 (MCP-4) in monocyte/macrophage recruitment in acute renal inflammation." *J. Pathol.* 194((2)): 239-46.

Chung, H. K., I. K. Lee, et al. (2002). "Statin inhibits interferon-gamma-induced expression of intercellular adhesion molecule-1 (ICAM-1) in vascular endothelial and smooth muscle cells." *Exp Mol Med* 34(6): 451-61.

Creery, D., W. Weiss, et al. (2004). "Down-regulation of CXCR-4 and CCR-5 expression by interferon-gamma is associated with inhibition of chemotaxis and human immunodeficiency virus (HIV) replication but not HIV entry into human monocytes." *Clin Exp Immunol* 137(1): 156-65.

Csaszar, A. and T. Abel (2001). "Receptor polymorphisms and diseases." *Eur J Pharmacol* 414(1): 9-22.

Dawson, T. C., M. A. Beck, et al. (2000). "Contrasting effects of CCR5 and CCR2 deficiency in the pulmonary inflammatory response to influenza A virus." *Am J Pathol* 156(6): 1951-9.

Denkers, E. Y. (2003). "From cells to signaling cascades: manipulation of innate immunity by *Toxoplasma gondii*." *FEMS Immunol Med Microbiol* 39(3): 193-203.

Di Stefano, A., A. Capelli, et al. (2001). "Decreased T lymphocyte infiltration in bronchial biopsies of subjects with severe chronic obstructive pulmonary disease." *Clin Exp Allergy* 31(6): 893-902.

Dickson, B. C. and A. I. Gotlieb (2003). "Towards understanding acute destabilization of vulnerable atherosclerotic plaques." *Cardiovasc Pathol* 12(5): 237-48.

Dohi, T., K. Fujihashi, et al. (2000). "Mice deficient in Th1- and Th2-type cytokines develop distinct forms of hapten-induced colitis." *Gastroenterology* 119(3): 724-33.

Elhage, R., J. Jawien, et al. (2003). "Reduced atherosclerosis in interleukin-18 deficient apolipoprotein E-knockout mice." *Cardiovasc Res* 59(1): 234-40.

Fahmy, N. M., M. H. Yamani, et al. (2003). "Chemokine and receptor-gene expression during early and late acute rejection episodes in human cardiac allografts." *Transplantation* 75(12): 2044-7.

Foxman, E. F., M. Zhang, et al. (2002). "Inflammatory mediators in uveitis: differential induction of cytokines and chemokines in Th1-versus Th2-mediated ocular inflammation." *J Immunol* 168(5): 2483-92.

Fraziano, M., G. Cappelli, et al. (1999). "Expression of CCR5 is increased in human monocyte-derived macrophages and alveolar macrophages in the course of in vivo and in vitro *Mycobacterium tuberculosis* infection." *AIDS Res Hum Retroviruses* 15(10): 869-74.

Gallardo, E., I. de Andres, et al. (2001). "Cathepsins are upregulated by IFN-gamma/STAT1 in human muscle culture: a possible active factor in dermatomyositis." *J Neuropathol Exp Neurol* 60(9): 847-55.

Garlet, G. P., W. Martins, Jr., et al. (2003). "Patterns of chemokines and chemokine receptors expression in different forms of human periodontal disease." *J Periodontal Res* 38(2): 210-7.

Gazzinelli, R. T., M. Wysocka, et al. (1996). "In the absence of endogenous IL-10, mice acutely infected with *Toxoplasma gondii* succumb to a lethal immune response dependent on CD4+ T cells and accompanied by overproduction of IL-12, IFN-gamma and TNF-alpha." *J Immunol* 157(2): 798-805.

Gerdes, N., G. K. Sukhova, et al. (2002). "Expression of interleukin (IL)-18 and functional IL-18 receptor on human vascular endothelial cells, smooth muscle cells, and macrophages: implications for atherogenesis." *J Exp Med* 195(2): 245-57.

Glass, W. G. and T. E. Lane (2003). "Functional analysis of the CC chemokine receptor 5 (CCR5) on virus-specific CD8+ T cells following coronavirus infection of the central nervous system." *Virology* 312(2): 407-14.

Hardaker, E. L., A. M. Bacon, et al. (2004). "Regulation of TNF-alpha- and IFN-gamma-induced CXCL10 expression: participation of the airway smooth muscle in the pulmonary inflammatory response in chronic obstructive pulmonary disease." *Faseb J* 18(1): 191-3.

Hayashi, T., L. Beck, et al. (2004). "Inhibition of experimental asthma by indoleamine 2,3-dioxygenase." *J Clin Invest* 114(2): 270-9.

Hillyer, P., E. Mordelet, et al. (2003). "Chemokines, chemokine receptors and adhesion molecules on different human endothelia: discriminating the tissue-specific functions that affect leucocyte migration." *Clin Exp Immunol* 134(3): 431-41.

Hoffmann, K. F., T. C. McCarty, et al. (2001). "Disease fingerprinting with cDNA microarrays reveals distinct gene expression profiles in lethal type 1 and type 2 cytokine-mediated inflammatory reactions." *Faseb J* 15(13): 2545-7.

Huffnagle, G. B., L. K. McNeil, et al. (1999). "Cutting edge: Role of C-C chemokine receptor 5 in organ-specific and innate immunity to *Cryptococcus neoformans*." *J Immunol* 163(9): 4642-6.

Inagaki, Y., S. Yamagishi, et al. (2002). "Interferon-gamma-induced apoptosis and activation of THP-1 macrophages." *Life Sci* 71(21): 2499-508.

Johnston, C. J., J. P. Williams, et al. (2002). "Radiation-induced pulmonary fibrosis: examination of chemokine and chemokine receptor families." *Radiat Res* 157(3): 256-65.

Kashiwamura, S., H. Ueda, et al. (2002). "Roles of interleukin-18 in tissue destruction and compensatory reactions." *J Immunother* 25 Suppl 1: S4-11.

Katakai, T., T. Hara, et al. (2003). "Th1-biased tertiary lymphoid tissue supported by CXC chemokine ligand 13-producing stromal network in chronic lesions of autoimmune gastritis." *J Immunol* 171(8): 4359-68.

Katchar, K., A. Eklund, et al. (2003). "Expression of Th1 markers by lung accumulated T cells in pulmonary sarcoidosis." *J Intern Med* 254(6): 564-71.

Kaufman, J., P. J. Sime, et al. (2004). "Expression of CD154 (CD40 ligand) by human lung fibroblasts: differential regulation by IFN-gamma and IL-13, and implications for fibrosis." *J Immunol* 172(3): 1862-71.

Kelsen, S. G., M. O. Aksoy, et al. (2004). "The chemokine receptor CXCR3 and its splice variant are expressed in human airway epithelial cells." *Am J Physiol Lung Cell Mol Physiol* 287(3): L584-91.

Kimura-Shimmyo, A., S. Kashiwamura, et al. (2002). "Cytokine-induced injury of the lacrimal and salivary glands." *J Immunother* 25 Suppl 1: S42-51.

Kunkel, E. J., J. Boisvert, et al. (2002). "Expression of the chemokine receptors CCR4, CCR5, and CXCR3 by human tissue-infiltrating lymphocytes." *Am J Pathol* 160(1): 347-55.

Kuziel, W. A., T. C. Dawson, et al. (2003). "CCR5 deficiency is not protective in the early stages of atherogenesis in apoE knockout mice." *Atherosclerosis* 167(1): 25-32.

Kwak, B. R., S. Myit, et al. (2002). "PPARgamma but not PPARalpha ligands are potent repressors of major histocompatibility complex class II induction in atheroma-associated cells." *Circ Res* 90(3): 356-62.

Larousserie, F., S. Pflanz, et al. (2004). "Expression of IL-27 in human Th1-associated granulomatous diseases." *J Pathol* 202(2): 164-71.

Laurat, E., B. Poirier, et al. (2001). "In vivo downregulation of T helper cell 1 immune responses reduces atherogenesis in apolipoprotein E-knockout mice." *Circulation* 104(2): 197-202.

Lavigne, L. M., L. R. Schopf, et al. (1998). "The role of recombinant murine IL-12 and IFN-in the pathogenesis of a murine systemic *Candida albicans* infection." *J. Immunol.* 160: 284-92.

Le Page, C., P. Genin, et al. (2000). "Interferon activation and innate immunity." *Rev Immunogenet* 2(3): 374-86.

Leckie, M. J., G. R. Jenkins, et al. (2003). "Sputum T lymphocytes in asthma, COPD and healthy subjects have the phenotype of activated intraepithelial T cells (CD69+ CD103+)." *Thorax* 58(1): 23-9.

Lindell, D. M., T. J. Standiford, et al. (2001). "Macrophage inflammatory protein 1alpha/CCL3 is required for clearance of an acute *Klebsiella pneumoniae* pulmonary infection." *Infect Immun* 69(10): 6364-9.

Littlewood, T. D. and M. R. Bennett (2003). "Apoptotic cell death in atherosclerosis." *Curr Opin Lipidol* 14(5): 469-75.

Luckow, B., J. Joergensen, et al. (2004). "Reduced intragraft mRNA expression of matrix metalloproteinases Mmp3, Mmp12, Mmp13 and Adam8, and diminished transplant arteriosclerosis in Ccr5-deficient mice." *Eur J Immunol* 34(9): 2568-78.

Lundin, K. E., E. M. Nilsen, et al. (2003). "Oats induced villous atrophy in coeliac disease." *Gut* 52(11): 1649-52.

Mack, M., J. Cihak, et al. (2001). "Expression and characterization of the chemokine receptors CCR2 and CCR5 in mice." *J Immunol* 166(7): 4697-704.

Maiuri, L., C. Ciacci, et al. (2000). "Interleukin 15 mediates epithelial changes in celiac disease." *Gastroenterology* 119(4): 996-1006.

Mallat, Z., A. Gojova, et al. (2003). "Induction of a regulatory T cell type 1 response reduces the development of atherosclerosis in apolipoprotein E-knockout mice." *Circulation* 108(10): 1232-7.

Marshall, T. G. and F. E. Marshall (2004). "Sarcoidosis succumbs to antibiotics—implications for autoimmune disease." *Autoimmun Rev* 3(4): 295-300.

Martinet, W. and M. M. Kockx (2004). "Apoptosis in atheroclerosis: implications for plaque destabilization." *Verh K Acad Geneeskd Belg* 66(1): 61-79.

Marx, N., B. Kehrle, et al. (2002). "PPAR activators as anti-inflammatory mediators in human T lymphocytes: implications for atherosclerosis and transplantation-associated arteriosclerosis." *Circ Res* 90(6): 703-10.

Masutani, K., M. Tokumoto, et al. (2003). "Strong polarization toward Th1 immune response in ANCA-associated glomerulonephritis." *Clin Nephrol* 59(6): 395-405.

Mention, J. J., B. M. Ahmed, et al. (2003). "Interleukin 15: a key to disrupted intraepithelial lymphocyte homeostasis and lymphomagenesis in celiac disease." *Gasteroenterology* 126((4)): 1217-8.

Michel, J. B. (2003). "Anoikis in the cardiovascular system: known and unknown extracellular mediators." *Arterioscler Thromb Vasc Biol* 23(12): 2146-54.

Miotto, D., M. P. Ruggieri, et al. (2003). "Interleukin-13 and -4 expression in the central airways of smokers with chronic bronchitis." *Eur Respir J* 22(4): 602-8.

Monteleone, G., S. L. Pender, et al. (2001). "Role of interferon alpha in promoting T helper cell type I responses in the small intestine in coeliac disease." *Gut* 48((3)): 425-9.

Monteleone, G., S. L. Pender, et al. (2001). "Interferon-alpha drives T cell-mediated immunopathology in the intestine." *Eur J Immunol* 31(8): 2247-55.

Nansen, A., O. Marker, et al. (2000). "CCR2+ and CCR5+ CD8+ T cells increase during viral infection and migrate to sites of infection." *Eur J Immunol* 30(7): 1797-806.

Nissinen, R., M. Leirisalo-Repo, et al. (2003). "CCR3, CCR5, interleukin 4, and interferon-gamma expression on synovial and peripheral T cells and monocytes in patients with rheumatoid arthritis." *J Rheumatol* 30(9): 1928-34.

Oppermann, M. (2004). "Chemokine receptor CCR5: insights into structure, function, and regulation." *Cell Signal* 16(11): 1201-10.

Page, G., G. Chevrel, et al. (2004). "Anatomic localization of immature and mature dendritic cell subsets in dermatomyositis and polymyositis: Interaction with chemokines and Th1 cytokine-producing cells." *Arthritis Rheum* 50(1): 199-208.

Peters, W. and I. F. Charo (2001). "Involvement of chemokine receptor 2 and its ligand, monocyte chemoattractant protein-1, in the development of atherosclerosis: lessons from knockout mice." *Curr Opin Lipidol* 12(2): 175-80.

Profumo, E., A. Siracusano, et al. (2003). "Cytokine expression in circulating T lymphocytes from patients undergoing carotid endarterectomy." *J Cardiovasc Surg (Torino)* 44(2): 237-42.

Qin, Z., J. Schwartzkopff, et al. (2003). "A critical requirement of interferon gamma-mediated angiostasis for tumor rejection by CD8+ T cells." *Cancer Res* 63(14): 4095-100.

Rodriguez-Sosa, M., A. R. Satoskar, et al. (2002). "Chronic helminth infection induces alternatively activated macrophages expressing high levels of CCR5 with low interleukin-12 production and Th2-biasing ability." *Infect Immun* 70(7): 3656-64.

Rosloniec, E. F., K. Latham, et al. (2002). "Paradoxical roles of IFN-gamma in models of Th1-mediated autoimmunity." *Arthritis Res* 4(6): 333-6.

Rottenberg, M. E., A. Gigliotti-Rothfuchs, et al. (2002). "The role of IFN-gamma in the outcome of chlamydial infection." *Curr Opin Immunol* 14(4): 444-51.

Sakash, J. B., G. I. Byrne, et al. (2002). "Cytokines induce indoleamine 2,3-dioxygenase expression in human atheroma-associated cells: implications for persistent *Chlamydophila pneumoniae* infection." *Infect Immun* 70(7): 3959-61.

Sandler, N. G., M. M. Mentink-Kane, et al. (2003). "Global gene expression profiles during acute pathogen-induced pulmonary inflammation reveal divergent roles for Th1 and Th2 responses in tissue repair." *J. Immunol.* 171: 3655-3667.

Santucci, M. B., M. Bocchino, et al. (2004). "Expansion of CCR5+ CD4+ T-lymphocytes in the course of active pulmonary tuberculosis." *Eur Respir J* 24(4): 638-43.

Schmidt, C., T. Marth, et al. (2002-2003). "Interleukin-12 antagonists as new therapeutic agents in inflammatory bowel disease." *Pathobiology* 70((3)): 177-83.

Schroder, K., P. J. Hertzog, et al. (2004). "Interferon-gamma: an overview of signals, mechanisms and functions." *J Leukoc Biol* 75(2): 163-89.

Schuh, J. M., K. Blease, et al. (2002). "The role of CC chemokine receptor 5 (CCR5) and RANTES/CCL5 during chronic fungal asthma in mice." *Faseb J* 16(2): 228-30.

Shapshak, P., R. Duncan, et al. (2004). "Elevated expression of IFN-gamma in the HIV-1 infected brain." *Front. Biosci.* 9: 1073-81.

Sollid, L. M. (2002). "Coeliac disease: dissecting a complex inflammatory disorder." *Nat Rev Immunol* 2(9): 647-55.

Song, H. K., H. Noorchashm, et al. (2003). "Specialized CC-chemokine secretion by Th1 cells in destructive autoimmune myocarditis." *J Autoimmun* 21(4): 295-303.

Souto, J. T., J. C. Aliberti, et al. (2003). "Chemokine production and leukocyte recruitment to the lungs of *Paracoccidioides brasiliensis*-infected mice is modulated by interferon-gamma" *Am J Pathol* 163(2): 583-90.

Sredni-Kenigsbuch, D. (2002). "TH!/TH2 cytokines in the central nervous system." *Int. J. Neurosci.* 112((6)): 665-703.

Steinbrecher, U. P., A. Gomez-Munoz, et al. (2004). "Acid sphingomyelinase in macrophage apoptosis." *Curr Opin Lipidol* 15(5): 531-7.

Stoneman, V. E. and M. R. Bennett (2004). "Role of apoptosis in atherosclerosis and its therapeutic implications." *Clin Sci (Lond)* 107(4): 343-54.

Storm van's Gravesande, K., M. D. Layne, et al. (2002). "IFN regulatory factor-1 regulates IFN-gamma-dependent cathepsin S expression." *J Immunol* 168(9): 4488-94.

Szabo, S. J., B. M. Sullivan, et al. (2003). "Molecular mechanisms regulating Th1 immune responses." *Annu Rev Immunol* 21: 713-58.

Teng, Y. T. (2003). "The role of acquired immunity and periodontal disease progression." *Crit. Rev Oral Biol Med* 14(4): 237-52.

Tsiavou, A., D. Degiannis, et al. (2004). "Intracellular IFN-gamma production and IL-12 serum levels in latent autoimmune diabetes of adults (LADA) and in type 2 diabetes." *J Interferon Cytokine Res* 24(7): 381-7.

Tsoumakidou, M., N. Tzanakis, et al. (2004). "Inflammatory cell profiles and T-lymphocyte subsets in chronic obstructive pulmonary disease and severe persistent asthma." *Clin Exp Allergy* 34(2): 234-40.

Ueland, T., L. I. Sikkeland, et al. (2003). "Myocardial gene expression of inflammatory cytokines after heart transplantation in relation to the development of transplant coronary artery disease." *Am J Cardiol* 92(6): 715-7.

Van Den Blink, B., T. Ten Hove, et al. (2002). "From extracellular to intracellular targets, inhibiting MAP kinases in treatment of Crohn's disease." *Ann N Y Acad Sci* 973: 349-58.

Veitch, A. M., L. M. Higgins, et al. (2003). "Impaired rejection and mucosal injury of small intestinal allografts lacking the interferon-gamma receptor." *Int J Exp Pathol* 84(3): 107-13.

Vervoordeldonk, M. J. and P. P. Tak (2002). "Cytokines in rheumatoid arthritis." *Curr Rheumatol Rep* 4(3): 208-17.

Viles-Gonzalez, J. F., S. X. Anand, et al. (2004). "Update in atherothrombotic disease." *Mt Sinai J Med* 71(3): 197-208.

Wagner, A. H., M. Gebauer, et al. (2002). "Cytokine-inducible CD40 expression in human endothelial cells is mediated by interferon regulatory factor-1." *Blood* 99(2): 520-5.

Wagner, D. H., Jr., G. Vaitaitis, et al. (2002). "Expression of CD40 identifies a unique pathogenic T cell population in type 1 diabetes." *Proc Natl Acad Sci USA* 99(6): 3782-7.

Whitman, S. C., P. Ravisankar, et al. (2002). "IFN-gamma deficiency exerts gender-specific effects on atherogenesis in apolipoprotein E-/- mice." *J Interferon Cytokine Res* 22(6): 661-70.

Whitman, S. C., P. Ravisankar, et al. (2002). "Interleukin-18 enhances atherosclerosis in apolipoprotein E(-/-) mice through release of interferon-gamma" *Circ Res* 90((2)): E34-8.

Whitman, S. C., P. Ravisankar, et al. (2000). "Exogenous interferon-gamma enhances atherosclerosis in apolipoprotein E-/- mice." *Am J Pathol* 157(6): 1819-24.

Widner, B., M. Ledochowski, et al. (2000). "Interferon-gamma-induced tryptophan degradation: neuropsychiatric and immunological consequences." *Curr Drug Metab* 1(2): 193-204.

Wu, J., B. Z. Alizadeh, et al. (2004). "Association of FAS (TNFRSF6)-670 gene polymorphism with villous atrophy in coeliac disease." *World J Gastroenterol* 10(5): 717-20.

Wu, L., G. LaRosa, et al. (1997). "Interaction of chemokine receptor CCR5 with its ligands: multiple domains for HIV-1 gp120 binding and a single domain for chemokine binding." *J Exp Med* 186(8): 1373-81.

Wuttge, D. M., X. Zhou, et al. (2004). "CXCL16/SR-PSOX is an interferon-gamma-regulated chemokine and scavenger receptor expressed in atherosclerotic lesions." *Arterioscler. Thromb. Vasc. Biol.* 24((5)): 750-5.

Wynn, T. A., M. Hesse, et al. (2004). "P-selectin suppresses hepatic inflammation and fibrosis in mice by regulating interferon gamma and the IL-13 decoy receptor." *Hepatology* 39(3): 676-87.

Yamazaki, K., H. Yoshie, et al. (2003). "T cell regulation of the immune response to infection in periodontal diseases." *Histol Histopathol* 18(3): 889-96.

Zaitseva, M., L. R. King, et al. (2001). "Human peripheral blood T cells, monocytes, and macrophages secrete macrophage inflammatory proteins 1alpha and 1beta following stimulation with heat-inactivated *Brucella abortus*." *Infect Immun* 69(6): 3817-26.

Zhong, M. X., W. A. Kuziel, et al. (2004). "Chemokine receptor 5 is dispensable for innate and adaptive immune responses to *Listeria monocytogenes* infection." *Infect Immun* 72(2): 1057-64.

Zhou, Y., D. Huang, et al. (2003). "Relative importance of CCR5 and antineutrophil cytoplasmic antibodies in patients with Wegener's granulomatosis." *J Rheumatol* 30(7): 1541-7.

What is claimed:

1. A method of treating chronic obstructive pulmonary disease (COPD) in a subject, comprising detecting an elevated level of IFN-γ and/or IL-13 and administering an effective amount of chemokine receptor 5 (CCR5) antagonist maraviroc to a subject with elevated levels of IFN-γ and/or IL-13 as compared to normal levels, thereby treating said COPD.

2. The method of claim 1, wherein said subject is a smoker with COPD.

3. The method of claim 1, wherein said antagonist specifically binds to CCR5.

4. The method of claim 1, wherein said antagonist binds to a mammalian CCR5.

5. The method of claim 4, wherein the mammalian CCR5 is a human CCR5.

6. The method of claim 1, wherein said antagonist inhibits binding of one or more chemokines selected from the group consisting of MIP-1α, MIP1β, and RANTES to the receptor.

7. The method of claim 1, wherein said antagonist inhibits one or more functions associated with binding of said one or more chemokines to the receptor.

8. The method of claim 1, wherein said COPD is chronic bronchitis.

9. The method of claim 1, wherein said COPD is emphysema.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
attctccaca ccctgtttcg                                                        20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gttctcctgt ggatcgggta                                                        20

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ctgggattca cctcaagaac at                                                     22

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ttacttggga cacctttag c                                                       21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ctgccccttc ctcagtcata                                                        20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gtgcattccg cttagctttc                                                        20

<210> SEQ ID NO 7
<211> LENGTH: 19
<212> TYPE: DNA

```
<213> ORGANISM: Artificial Sequence
<220> FEATURE:
<223> OTHER INFORMATION: Primer

<400> SEQUENCE: 7
tcttcctgga gcagtgtgg                                                  19

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tccggatcta ggcaggttt                                                  19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
aagtgctgcc gtcattttct                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gtggcaatga tctcaacacg                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gctctgcatc agtgacggta                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
taatttcggg tcaatgcaca                                                 20

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ctgctcaagg cttccttatg tt                                              22
```

```
<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
cctttgtcgt ttatgagcct tc                                              22

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tctggaagcc cattacacaa                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tttgtaacca tttggcacga                                                 20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
aagctggaaa tgaagccaaa                                                 20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cttctcgttc caggcattgt                                                 20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cgtccctgtg acactcaaga                                                 20

<210> SEQ ID NO 20
<211> LENGTH: 20
<212> TYPE: DNA
<213> ORGANISM: Artificial Sequence
<220> FEATURE:
<223> OTHER INFORMATION: Primer
```

```
<400> SEQUENCE: 20
taattgggcc aacagtagcc                                                    20

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
gagctgctgg agcactacg                                                     19

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cacggagtac cgggttaaga                                                    20

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gactgtgtac tcaagctggt gc                                                 22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
ctcagtacca gcggaatctt ct                                                 22

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
cggaggagtg gctgaagtgg ag                                                 22

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
ctcagtacca gcggaatctt ct                                                 22

<210> SEQ ID NO 27
<211> LENGTH: 25
<212> TYPE: DNA
```

```
<213> ORGANISM: Artificial Sequence
<220> FEATURE:
<223> OTHER INFORMATION: Primer

<400> SEQUENCE: 27
acaacaacaa tcggctgctc tgatg                                              25

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
tgcgcgcctt gagcctggcg aac                                                23
```